(12) United States Patent
Horwitz et al.

(10) Patent No.: US 8,481,024 B2
(45) Date of Patent: Jul. 9, 2013

(54) VACCINES AGAINST TULAREMIA

(75) Inventors: Marcus A. Horwitz, Los Angeles, CA (US); Qingmei Jia, Los Angeles, CA (US); Bai-Yu L. Clemens, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/319,024

(22) PCT Filed: May 3, 2010

(86) PCT No.: PCT/US2010/033352
§ 371 (c)(1),
(2), (4) Date: Nov. 4, 2011

(87) PCT Pub. No.: WO2010/129457
PCT Pub. Date: Nov. 11, 2010

(65) Prior Publication Data
US 2012/0052085 A1    Mar. 1, 2012

Related U.S. Application Data

(60) Provisional application No. 61/175,436, filed on May 4, 2009.

(51) Int. Cl.
*A61K 39/02* (2006.01)

(52) U.S. Cl.
USPC .... 424/93.2; 424/93.4; 424/200.1; 424/184.1

(58) Field of Classification Search
None
See application file for complete search history.

(56) References Cited

U.S. PATENT DOCUMENTS 8,206,700 B2 * 6/2012 Horwitz et al. .............. 424/93.1
2010/0215679 A1 8/2010 Horwitz et al.

FOREIGN PATENT DOCUMENTS

WO 2008012538 A2 1/2008

OTHER PUBLICATIONS

Janovska, S. et al., "Identification of immunoreactive antigens in membrane proteins enriched fraction from *Francisella tularensis* LVS", Immunology letters, 2007, vol. 108, pp. 151-159.
Jia, Q. et al., "Recombinant attenuated Listeria monocytogenes vaccine expressing *Francisella tularensis* IglC induces protection in mice against aerosolized Type A *F tularensis*", Vaccine, Jan. 4, 2009, vol. 27, pp. 1216-1229.
Lee, Soo-Jung, International Search Report and Written Opinion, date of mailing of report: Feb. 25, 2011, International Application No. PCT/US2010/033352.

* cited by examiner

*Primary Examiner* — Padma V Baskar
(74) *Attorney, Agent, or Firm* — Joseph R. Baker, Jr.; Gavrilovich, Dodd & Lindsey LLP

(57) ABSTRACT

The disclosure relates generally to an antigenic composition useful for immunization against tularemia. The disclosure is a method for producing a vaccine for preventing tularemia in humans and animals, a new vaccine against tularemia in humans and animals, and a new approach to producing vaccines against tularemia.

12 Claims, 19 Drawing Sheets

FIGURE 5

| Vaccine Group | % Survival | Mean Survival Time [a] | P vs Sham (Log-rank test) | P vs LVS (Log-rank test) |
|---|---|---|---|---|
| Sham | 0 | 5 | - | <0.0001 |
| LVS | 62.5 | 16 | <0.0001 | - |
| LVSΔcapB | 0 | 10 | <0.0001 | 0.003 |
| rLVSΔcapB/IglA | 50 | 16 | <0.0001 | ns |
| rLVSΔcapB/IglC | 37.5 | 14 | <0.0001 | ns |

Vaccines administered i.d.

SEQUENCE LISTING

<160> NUMBER OF SEQ ID NOS: 24

<210> SEQ ID NO 1
<211> LENGTH: 1545
<212> TYPE: DNA
<213> ORGANISM: Francisella tularensis
<220> FEATURE:
<221> NAME/KEY: CDS
<222> LOCATION: (1)..(1545)

<400> SEQUENCE: 1

| | | | | | | | | | | | | | | | | |
|---|---|---|---|---|---|---|---|---|---|---|---|---|---|---|---|---|
| atg | aag | ctc | aat | aaa | att | act | tta | gga | att | tta | agt | cta | agt | atc | gca | 48 |
| Met | Lys | Leu | Asn | Lys | Ile | Thr | Leu | Gly | Ile | Leu | Ser | Leu | Ser | Ile | Ala | |
| 1 | | | | 5 | | | | | 10 | | | | | 15 | | |

| aca | acg | act | ttt | gcc | aca | gat | gtg | aat | aat | agc | aaa | cca | aat | gat | tat | 96 |
|---|---|---|---|---|---|---|---|---|---|---|---|---|---|---|---|---|
| Thr | Thr | Thr | Phe | Ala | Thr | Asp | Val | Asn | Asn | Ser | Lys | Pro | Asn | Asp | Tyr | |
| | | | 20 | | | | | 25 | | | | | 30 | | | |

| gga | act | ctt | gta | aaa | ata | aaa | caa | aaa | tta | ttt | aat | aat | gcg | aat | act | 144 |
|---|---|---|---|---|---|---|---|---|---|---|---|---|---|---|---|---|
| Gly | Thr | Leu | Val | Lys | Ile | Lys | Gln | Lys | Leu | Phe | Asn | Asn | Ala | Asn | Thr | |
| | 35 | | | | | 40 | | | | | 45 | | | | | |

| cta | aaa | act | aca | act | cca | ata | aag | cac | gta | gta | ata | ata | ttc | caa | gag | 192 |
|---|---|---|---|---|---|---|---|---|---|---|---|---|---|---|---|---|
| Leu | Lys | Thr | Thr | Thr | Pro | Ile | Lys | His | Val | Val | Ile | Ile | Phe | Gln | Glu | |
| 50 | | | | | 55 | | | | | 60 | | | | | | |

| aat | aac | tct | ttt | gat | aga | tac | ttt | gga | atg | tac | ccc | aat | gcc | aaa | aac | 240 |
|---|---|---|---|---|---|---|---|---|---|---|---|---|---|---|---|---|
| Asn | Asn | Ser | Phe | Asp | Arg | Tyr | Phe | Gly | Met | Tyr | Pro | Asn | Ala | Lys | Asn | |
| 65 | | | | 70 | | | | | 75 | | | | | 80 | | |

| cca | gag | ggt | gag | cca | aaa | ttt | gta | gcc | aaa | gaa | aat | act | cca | aat | gtt | 288 |
|---|---|---|---|---|---|---|---|---|---|---|---|---|---|---|---|---|
| Pro | Glu | Gly | Glu | Pro | Lys | Phe | Val | Ala | Lys | Glu | Asn | Thr | Pro | Asn | Val | |
| | | | | 85 | | | | | 90 | | | | | 95 | | |

| aat | ggt | ctg | aca | aaa | caa | tta | tta | gag | aat | aat | cca | aat | aca | aaa | aat | 336 |
|---|---|---|---|---|---|---|---|---|---|---|---|---|---|---|---|---|
| Asn | Gly | Leu | Thr | Lys | Gln | Leu | Leu | Glu | Asn | Asn | Pro | Asn | Thr | Lys | Asn | |
| | | | 100 | | | | | 105 | | | | | 110 | | | |

| cct | tat | cgt | tta | gat | aga | aat | ttc | caa | cct | tgc | tca | caa | aat | cat | gag | 384 |
|---|---|---|---|---|---|---|---|---|---|---|---|---|---|---|---|---|
| Pro | Tyr | Arg | Leu | Asp | Arg | Asn | Phe | Gln | Pro | Cys | Ser | Gln | Asn | His | Glu | |
| | | 115 | | | | | 120 | | | | | 125 | | | | |

| tac | cat | caa | gaa | att | tct | tct | ttt | aat | ggt | gga | tta | atg | aac | aaa | ttt | 432 |
|---|---|---|---|---|---|---|---|---|---|---|---|---|---|---|---|---|
| Tyr | His | Gln | Glu | Ile | Ser | Ser | Phe | Asn | Gly | Gly | Leu | Met | Asn | Lys | Phe | |
| | 130 | | | | | 135 | | | | | 140 | | | | | |

| gtt | gaa | cat | ggt | ggt | cat | gat | aat | gac | acc | tat | aaa | caa | aac | tgt | gat | 480 |
|---|---|---|---|---|---|---|---|---|---|---|---|---|---|---|---|---|
| Val | Glu | His | Gly | Gly | His | Asp | Asn | Asp | Thr | Tyr | Lys | Gln | Asn | Cys | Asp | |
| 145 | | | | 150 | | | | | 155 | | | | | 160 | | |

| ggt | caa | gtc | atg | gga | tat | tat | gat | ggt | aat | act | gtc | aca | gca | tta | tgg | 528 |
|---|---|---|---|---|---|---|---|---|---|---|---|---|---|---|---|---|
| Gly | Gln | Val | Met | Gly | Tyr | Tyr | Asp | Gly | Asn | Thr | Val | Thr | Ala | Leu | Trp | |
| | | | | 165 | | | | | 170 | | | | | 175 | | |

| aat | tac | gca | caa | aat | ttc | gct | cta | aat | gat | aat | acg | ttt | ggt | aca | act | 576 |
|---|---|---|---|---|---|---|---|---|---|---|---|---|---|---|---|---|
| Asn | Tyr | Ala | Gln | Asn | Phe | Ala | Leu | Asn | Asp | Asn | Thr | Phe | Gly | Thr | Thr | |
| | | | 180 | | | | | 185 | | | | | 190 | | | |

| ttt | ggt | cca | tca | aca | cct | ggt | gcc | ctt | aac | cta | gtg | gct | ggt | gca | aat | 624 |
|---|---|---|---|---|---|---|---|---|---|---|---|---|---|---|---|---|
| Phe | Gly | Pro | Ser | Thr | Pro | Gly | Ala | Leu | Asn | Leu | Val | Ala | Gly | Ala | Asn | |
| | | 195 | | | | | 200 | | | | | 205 | | | | |

| ggt | cca | gca | atg | agt | cca | agt | ggt | aat | tta | gaa | aat | att | gaa | aac | agc | 672 |
|---|---|---|---|---|---|---|---|---|---|---|---|---|---|---|---|---|
| Gly | Pro | Ala | Met | Ser | Pro | Ser | Gly | Asn | Leu | Glu | Asn | Ile | Glu | Asn | Ser | |
| | 210 | | | | | 215 | | | | | 220 | | | | | |

| tat | atc | att | gat | gat | cct | aac | cca | tac | tac | gat | gat | tgc | tct | tat | ggt | 720 |
|---|---|---|---|---|---|---|---|---|---|---|---|---|---|---|---|---|
| Tyr | Ile | Ile | Asp | Asp | Pro | Asn | Pro | Tyr | Tyr | Asp | Asp | Cys | Ser | Tyr | Gly | |
| 225 | | | | 230 | | | | | 235 | | | | | 240 | | |

| aca | agt | aaa | tct | ggc | gat | aca | aat | aca | gct | gta | gca | aaa | att | act | gat | 768 |
|---|---|---|---|---|---|---|---|---|---|---|---|---|---|---|---|---|
| Thr | Ser | Lys | Ser | Gly | Asp | Thr | Asn | Thr | Ala | Val | Ala | Lys | Ile | Thr | Asp | |
| | | | | 245 | | | | | 250 | | | | | 255 | | |

| ggt | tat | aat | att | gga | cac | tat | cta | act | caa | aaa | ggt | att | act | tgg | ggt | 816 |

```
                                                                    -continued Gly Tyr Asn Ile Gly His Tyr Leu Thr Gln Lys Gly Ile Thr Trp Gly
                260                 265                 270 tgg ttc caa gga gga ttc aaa cca aca agc tac tct ggt aaa aca gca      864
Trp Phe Gln Gly Gly Phe Lys Pro Thr Ser Tyr Ser Gly Lys Thr Ala
        275                 280                 285 ata tgt gat gct atg agc act aat aag ttc ggt ata aaa tca aga gac      912
Ile Cys Asp Ala Met Ser Thr Asn Lys Phe Gly Ile Lys Ser Arg Asp
290                 295                 300 tat ata cct cat cat gag cct ttt aac tat tgg aaa gag aca tca aac      960
Tyr Ile Pro His His Glu Pro Phe Asn Tyr Trp Lys Glu Thr Ser Asn
305                 310                 315                 320 cct cat cat cta gca cca agt gat gat aag tat ata ggt agt aat gac     1008
Pro His His Leu Ala Pro Ser Asp Asp Lys Tyr Ile Gly Ser Asn Asp
                325                 330                 335 caa gct aac cat cag tac gac ata agt gaa ttt tgg aag gct ctt gat     1056
Gln Ala Asn His Gln Tyr Asp Ile Ser Glu Phe Trp Lys Ala Leu Asp
            340                 345                 350 caa aac acc atg cct gcg gta agt tac tta aaa gct cct gga tat caa     1104
Gln Asn Thr Met Pro Ala Val Ser Tyr Leu Lys Ala Pro Gly Tyr Gln
        355                 360                 365 gat ggt cat gga ggc tac tca aac cct cta gat gaa caa gaa tgg cta     1152
Asp Gly His Gly Gly Tyr Ser Asn Pro Leu Asp Glu Gln Glu Trp Leu
370                 375                 380 gtc aat act att aat aga atc aaa caa tca aaa gac tgg gat agc aca     1200
Val Asn Thr Ile Asn Arg Ile Lys Gln Ser Lys Asp Trp Asp Ser Thr
385                 390                 395                 400 gca att ata att att tat gat gac tct gat ggt gac tat gac cat gtc     1248
Ala Ile Ile Ile Ile Tyr Asp Asp Ser Asp Gly Asp Tyr Asp His Val
                405                 410                 415 tac agt cca aaa tca cag ttt agc gat att aaa gga aga caa ggc tat     1296
Tyr Ser Pro Lys Ser Gln Phe Ser Asp Ile Lys Gly Arg Gln Gly Tyr
            420                 425                 430 gga cca aga tta cca atg ctt gtt att tct cct tat act aaa gca aac     1344
Gly Pro Arg Leu Pro Met Leu Val Ile Ser Pro Tyr Thr Lys Ala Asn
        435                 440                 445 tat att gat cat tca tta ctt aat caa gca tct gta ctt aag ttt ata     1392
Tyr Ile Asp His Ser Leu Leu Asn Gln Ala Ser Val Leu Lys Phe Ile
450                 455                 460 gag tat aac tgg ggc att ggc tca gtt agt aag tat agt aat gat aaa     1440
Glu Tyr Asn Trp Gly Ile Gly Ser Val Ser Lys Tyr Ser Asn Asp Lys
465                 470                 475                 480 tac tca aac aat atc tta aac atg ttt gat ttt aat aaa aaa caa aaa     1488
Tyr Ser Asn Asn Ile Leu Asn Met Phe Asp Phe Asn Lys Lys Gln Lys
                485                 490                 495 aca cca aaa ctg att tta gac cct aag aca gga tta gta gtg gat aaa     1536
Thr Pro Lys Leu Ile Leu Asp Pro Lys Thr Gly Leu Val Val Asp Lys
            500                 505                 510 tta aac taa                                                         1545
Leu Asn <210> SEQ ID NO 2
<211> LENGTH: 514
<212> TYPE: PRT
<213> ORGANISM: Francisella tularensis

<400> SEQUENCE: 2

Met Lys Leu Asn Lys Ile Thr Leu Gly Ile Leu Ser Leu Ser Ile Ala
1               5                   10                  15

Thr Thr Thr Phe Ala Thr Asp Val Asn Asn Ser Lys Pro Asn Asp Tyr
            20                  25                  30
```

-continued

```
Gly Thr Leu Val Lys Ile Lys Gln Lys Leu Phe Asn Asn Ala Asn Thr
         35                  40                  45
Leu Lys Thr Thr Thr Pro Ile Lys His Val Val Ile Ile Phe Gln Glu
 50                  55                  60
Asn Asn Ser Phe Asp Arg Tyr Phe Gly Met Tyr Pro Asn Ala Lys Asn
 65                  70                  75                  80
Pro Glu Gly Glu Pro Lys Phe Val Ala Lys Glu Asn Thr Pro Asn Val
                 85                  90                  95
Asn Gly Leu Thr Lys Gln Leu Leu Glu Asn Asn Pro Asn Thr Lys Asn
                100                 105                 110
Pro Tyr Arg Leu Asp Arg Asn Phe Gln Pro Cys Ser Gln Asn His Glu
            115                 120                 125
Tyr His Gln Glu Ile Ser Ser Phe Asn Gly Gly Leu Met Asn Lys Phe
        130                 135                 140
Val Glu His Gly Gly His Asp Asn Asp Thr Tyr Lys Gln Asn Cys Asp
145                 150                 155                 160
Gly Gln Val Met Gly Tyr Tyr Asp Gly Asn Thr Val Thr Ala Leu Trp
                165                 170                 175
Asn Tyr Ala Gln Asn Phe Ala Leu Asn Asp Asn Thr Phe Gly Thr Thr
            180                 185                 190
Phe Gly Pro Ser Thr Pro Gly Ala Leu Asn Leu Val Ala Gly Ala Asn
        195                 200                 205
Gly Pro Ala Met Ser Pro Ser Gly Asn Leu Glu Asn Ile Glu Asn Ser
210                 215                 220
Tyr Ile Ile Asp Asp Pro Asn Pro Tyr Asp Asp Cys Ser Tyr Gly
225                 230                 235                 240
Thr Ser Lys Ser Gly Asp Thr Asn Thr Ala Val Ala Lys Ile Thr Asp
                245                 250                 255
Gly Tyr Asn Ile Gly His Tyr Leu Thr Gln Lys Gly Ile Thr Trp Gly
            260                 265                 270
Trp Phe Gln Gly Gly Phe Lys Pro Thr Ser Tyr Ser Gly Lys Thr Ala
        275                 280                 285
Ile Cys Asp Ala Met Ser Thr Asn Lys Phe Gly Ile Lys Ser Arg Asp
290                 295                 300
Tyr Ile Pro His His Glu Pro Phe Asn Tyr Trp Lys Glu Thr Ser Asn
305                 310                 315                 320
Pro His His Leu Ala Pro Ser Asp Asp Lys Tyr Ile Gly Ser Asn Asp
                325                 330                 335
Gln Ala Asn His Gln Tyr Asp Ile Ser Glu Phe Trp Lys Ala Leu Asp
            340                 345                 350
Gln Asn Thr Met Pro Ala Val Ser Tyr Leu Lys Ala Pro Gly Tyr Gln
        355                 360                 365
Asp Gly His Gly Gly Tyr Ser Asn Pro Leu Asp Glu Gln Glu Trp Leu
370                 375                 380
Val Asn Thr Ile Asn Arg Ile Lys Gln Ser Lys Asp Trp Asp Ser Thr
385                 390                 395                 400
Ala Ile Ile Ile Ile Tyr Asp Asp Ser Asp Gly Asp Tyr Asp His Val
                405                 410                 415
Tyr Ser Pro Lys Ser Gln Phe Ser Asp Ile Lys Gly Arg Gln Gly Tyr
            420                 425                 430
Gly Pro Arg Leu Pro Met Leu Val Ile Ser Pro Tyr Thr Lys Ala Asn
        435                 440                 445
Tyr Ile Asp His Ser Leu Leu Asn Gln Ala Ser Val Leu Lys Phe Ile
450                 455                 460
```

```
Glu Tyr Asn Trp Gly Ile Gly Ser Val Ser Lys Tyr Ser Asn Asp Lys
465                 470                 475                 480

Tyr Ser Asn Asn Ile Leu Asn Met Phe Asp Phe Asn Lys Lys Gln Lys
                485                 490                 495

Thr Pro Lys Leu Ile Leu Asp Pro Lys Thr Gly Leu Val Val Asp Lys
            500                 505                 510

Leu Asn

<210> SEQ ID NO 3
<211> LENGTH: 486
<212> TYPE: DNA
<213> ORGANISM: Francisella tularensis
<220> FEATURE:
<221> NAME/KEY: CDS
<222> LOCATION: (1)..(486)

<400> SEQUENCE: 3 atg ttg att ata atg att aga gtt tta aat aat gga gat aac aat atg     48
Met Leu Ile Ile Met Ile Arg Val Leu Asn Asn Gly Asp Asn Asn Met
1               5                   10                  15 gaa ctt caa tta gaa aat aaa caa gaa att att gat caa tta aat aaa     96
Glu Leu Gln Leu Glu Asn Lys Gln Glu Ile Ile Asp Gln Leu Asn Lys
                20                  25                  30 atc tta gaa ctc gaa atg tct gga gtt gtg cgt tat act cat tat tct    144
Ile Leu Glu Leu Glu Met Ser Gly Val Val Arg Tyr Thr His Tyr Ser
            35                  40                  45 tta atg att ata ggt cat aat aga att cct ata gtt agt tgg atg caa    192
Leu Met Ile Ile Gly His Asn Arg Ile Pro Ile Val Ser Trp Met Gln
        50                  55                  60 tct caa gca agt gaa agt tta act cat gct act gca gca ggt gaa atg    240
Ser Gln Ala Ser Glu Ser Leu Thr His Ala Thr Ala Ala Gly Glu Met
65                  70                  75                  80 ata act cac ttt ggt gag cat cca tct tta aaa ata gca gat tta aac    288
Ile Thr His Phe Gly Glu His Pro Ser Leu Lys Ile Ala Asp Leu Asn
                85                  90                  95 gaa act tat cag cat aat atc aat gat ata tta atc gaa agt cta gaa    336
Glu Thr Tyr Gln His Asn Ile Asn Asp Ile Leu Ile Glu Ser Leu Glu
                100                 105                 110 cat gag aaa aaa gct gtt tca gca tac tat gaa ctt cta aaa ctt gta    384
His Glu Lys Lys Ala Val Ser Ala Tyr Tyr Glu Leu Leu Lys Leu Val
            115                 120                 125 aat ggc aaa tca ata ata tta gaa gaa tat gca aga aaa ctc ata gtt    432
Asn Gly Lys Ser Ile Ile Leu Glu Glu Tyr Ala Arg Lys Leu Ile Val
        130                 135                 140 gaa gaa gaa acg cac att ggt gaa gta gaa aaa atg tta aga aaa cct    480
Glu Glu Glu Thr His Ile Gly Glu Val Glu Lys Met Leu Arg Lys Pro
145                 150                 155                 160 gca taa                                                            486
Ala

<210> SEQ ID NO 4
<211> LENGTH: 161
<212> TYPE: PRT
<213> ORGANISM: Francisella tularensis

<400> SEQUENCE: 4

Met Leu Ile Ile Met Ile Arg Val Leu Asn Asn Gly Asp Asn Asn Met
1               5                   10                  15

Glu Leu Gln Leu Glu Asn Lys Gln Glu Ile Ile Asp Gln Leu Asn Lys
                20                  25                  30
```

```
Ile Leu Glu Leu Glu Met Ser Gly Val Val Arg Tyr Thr His Tyr Ser
         35                  40                  45

Leu Met Ile Ile Gly His Asn Arg Ile Pro Ile Val Ser Trp Met Gln
 50                  55                  60

Ser Gln Ala Ser Glu Ser Leu Thr His Ala Thr Ala Ala Gly Glu Met
 65                  70                  75                  80

Ile Thr His Phe Gly Glu His Pro Ser Leu Lys Ile Ala Asp Leu Asn
                 85                  90                  95

Glu Thr Tyr Gln His Asn Ile Asn Asp Ile Leu Ile Glu Ser Leu Glu
            100                 105                 110

His Glu Lys Lys Ala Val Ser Ala Tyr Tyr Glu Leu Leu Lys Leu Val
        115                 120                 125

Asn Gly Lys Ser Ile Ile Leu Glu Glu Tyr Ala Arg Lys Leu Ile Val
130                 135                 140

Glu Glu Glu Thr His Ile Gly Glu Val Glu Lys Met Leu Arg Lys Pro
145                 150                 155                 160

Ala
```

<210> SEQ ID NO 5
<211> LENGTH: 1929
<212> TYPE: DNA
<213> ORGANISM: Francisella tularensis
<220> FEATURE:
<221> NAME/KEY: CDS
<222> LOCATION: (1)..(1929)

<400> SEQUENCE: 5

```
atg gga aaa ata ata ggt ata gat tta ggt act act aac tct tgt ctt      48
Met Gly Lys Ile Ile Gly Ile Asp Leu Gly Thr Thr Asn Ser Cys Leu
 1               5                  10                  15 gct att atg gat ggc aag act gct aaa gtt att gag aat gct gaa gga      96
Ala Ile Met Asp Gly Lys Thr Ala Lys Val Ile Glu Asn Ala Glu Gly
                20                  25                  30 cat aga aca aca cct tca gtt gtg gca tat act gat agc ggt gaa ata     144
His Arg Thr Thr Pro Ser Val Val Ala Tyr Thr Asp Ser Gly Glu Ile
            35                  40                  45 tta gta ggt caa gct gct aaa aga caa gct gta act aac cct gat aat     192
Leu Val Gly Gln Ala Ala Lys Arg Gln Ala Val Thr Asn Pro Asp Asn
 50                  55                  60 aca ttc ttt gct atc aag aga ctt ata ggt cgt aag tac gat gat aaa     240
Thr Phe Phe Ala Ile Lys Arg Leu Ile Gly Arg Lys Tyr Asp Asp Lys
 65                  70                  75                  80 gct gta caa gaa gat att aaa aag aaa gta cct tat gcg gta att aaa     288
Ala Val Gln Glu Asp Ile Lys Lys Lys Val Pro Tyr Ala Val Ile Lys
                85                  90                  95 gct gat aat ggt gat gct tgg gtt gct act aaa gaa ggc aaa aaa atg     336
Ala Asp Asn Gly Asp Ala Trp Val Ala Thr Lys Glu Gly Lys Lys Met
                100                 105                 110 gct cca cca caa gtt tct gca gaa gtt cta aga aaa atg aaa aaa aca     384
Ala Pro Pro Gln Val Ser Ala Glu Val Leu Arg Lys Met Lys Lys Thr
        115                 120                 125 gca gaa gac tat cta ggt gaa cca gtt aca gaa gct gta att aca gtg     432
Ala Glu Asp Tyr Leu Gly Glu Pro Val Thr Glu Ala Val Ile Thr Val
130                 135                 140 cca gca tac ttt aac gat agt caa aga caa gct aca aaa gat gct ggt     480
Pro Ala Tyr Phe Asn Asp Ser Gln Arg Gln Ala Thr Lys Asp Ala Gly
145                 150                 155                 160 aaa ata gca ggt ctt gaa gtt aaa aga att atc aac gag cct aca gcg     528
Lys Ile Ala Gly Leu Glu Val Lys Arg Ile Ile Asn Glu Pro Thr Ala
                165                 170                 175
```

```
gca gcg ctg gca tat ggt gta gac tct aag aaa ggt gag caa act gta      576
Ala Ala Leu Ala Tyr Gly Val Asp Ser Lys Lys Gly Glu Gln Thr Val
            180                 185                 190 gcg gtg tat gac cta ggt ggt ggt aca ttc gat atc tca att att gag      624
Ala Val Tyr Asp Leu Gly Gly Gly Thr Phe Asp Ile Ser Ile Ile Glu
                195                 200                 205 att gct gat gtt gat ggc gat aac caa atc gaa gta tta tca acc aat      672
Ile Ala Asp Val Asp Gly Asp Asn Gln Ile Glu Val Leu Ser Thr Asn
    210                 215                 220 ggt gat act ttc tta ggt ggt gaa gac ttc gac ttg gct tta atg aac      720
Gly Asp Thr Phe Leu Gly Gly Glu Asp Phe Asp Leu Ala Leu Met Asn
225                 230                 235                 240 tat cta att gac gag ttc aaa aaa gag caa ggt ata gat ctt cac aat      768
Tyr Leu Ile Asp Glu Phe Lys Lys Glu Gln Gly Ile Asp Leu His Asn
                245                 250                 255 gat aag ctt gct tta caa aga gtt aga gag gct gct gag aaa gct aaa      816
Asp Lys Leu Ala Leu Gln Arg Val Arg Glu Ala Ala Glu Lys Ala Lys
    260                 265                 270 gta gaa tta tct tca gca caa caa act gat gtt aac cta cct tac atc      864
Val Glu Leu Ser Ser Ala Gln Gln Thr Asp Val Asn Leu Pro Tyr Ile
275                 280                 285 aca gca gat gct act gga cct aag cac tta aat atc aaa gta act aga      912
Thr Ala Asp Ala Thr Gly Pro Lys His Leu Asn Ile Lys Val Thr Arg
                290                 295                 300 gct aag ttt gag tct tta gtt tct gat ctt gta atg aga tca ctt gag      960
Ala Lys Phe Glu Ser Leu Val Ser Asp Leu Val Met Arg Ser Leu Glu
305                 310                 315                 320 cct tgt aag aaa gct ctt gaa gat gct ggt tta agt aag tct gat att     1008
Pro Cys Lys Lys Ala Leu Glu Asp Ala Gly Leu Ser Lys Ser Asp Ile
                325                 330                 335 aca gaa gta tta cta gtg ggt gga caa act cgt atg cct cta gta caa     1056
Thr Glu Val Leu Leu Val Gly Gly Gln Thr Arg Met Pro Leu Val Gln
    340                 345                 350 gag aaa gta aaa gag ttt ttt ggt aaa gag cca cgt aaa gat gtg aac     1104
Glu Lys Val Lys Glu Phe Phe Gly Lys Glu Pro Arg Lys Asp Val Asn
355                 360                 365 cct gat gaa gct gtt gca gtt ggt gcg gct att caa ggt ggt gta tta     1152
Pro Asp Glu Ala Val Ala Val Gly Ala Ala Ile Gln Gly Gly Val Leu
                370                 375                 380 gca ggt gat gtt aaa gat att ctt tta ttg gat gta aca ccg ctt tct     1200
Ala Gly Asp Val Lys Asp Ile Leu Leu Leu Asp Val Thr Pro Leu Ser
385                 390                 395                 400 cta ggt att gag act atg gga ggt gtt atg act aag ctt atc gag aga     1248
Leu Gly Ile Glu Thr Met Gly Gly Val Met Thr Lys Leu Ile Glu Arg
                405                 410                 415 aat act acg att cct act aag aag tcg caa gta ttc tca aca gct gaa     1296
Asn Thr Thr Ile Pro Thr Lys Lys Ser Gln Val Phe Ser Thr Ala Glu
            420                 425                 430 gat aac cag cct gcg gta act att cat gta ctt caa ggt gag cgt gaa     1344
Asp Asn Gln Pro Ala Val Thr Ile His Val Leu Gln Gly Glu Arg Glu
                435                 440                 445 atg gct tct gca aac aaa tct tta ggt aga ttt gat ctg gca gat att     1392
Met Ala Ser Ala Asn Lys Ser Leu Gly Arg Phe Asp Leu Ala Asp Ile
450                 455                 460 cca cca gcg cca cgt ggt atg cca caa att gag gtt act ttt gat ata     1440
Pro Pro Ala Pro Arg Gly Met Pro Gln Ile Glu Val Thr Phe Asp Ile
465                 470                 475                 480 gat gct aac ggt ata tta aat gtg tct gct aaa gat aaa gct act ggt     1488
Asp Ala Asn Gly Ile Leu Asn Val Ser Ala Lys Asp Lys Ala Thr Gly
                485                 490                 495
```

-continued

| | | |
|---|---|---|
| aaa gag caa aat att gtg att aag tct tca agt ggt tta tct gaa gag<br>Lys Glu Gln Asn Ile Val Ile Lys Ser Ser Ser Gly Leu Ser Glu Glu<br>500 505 510 | 1536 | |
| gat atc gaa aaa atg gta caa gac gct gaa gct aat gca gaa gca gat<br>Asp Ile Glu Lys Met Val Gln Asp Ala Glu Ala Asn Ala Glu Ala Asp<br>515 520 525 | 1584 | |
| aaa aag ttc cat gat tta gtt act gct aga aat act gct gat aac tta<br>Lys Lys Phe His Asp Leu Val Thr Ala Arg Asn Thr Ala Asp Asn Leu<br>530 535 540 | 1632 | |
| att cat agc tca aga aaa gca att caa gaa ctg ggt gac aaa gta aca<br>Ile His Ser Ser Arg Lys Ala Ile Gln Glu Leu Gly Asp Lys Val Thr<br>545 550 555 560 | 1680 | |
| gca gca gaa aaa gaa aaa atc gaa gaa gct tgt aaa gag ctt gaa gca<br>Ala Ala Glu Lys Glu Lys Ile Glu Glu Ala Cys Lys Glu Leu Glu Ala<br>565 570 575 | 1728 | |
| gca act aaa ggt gat gat aag caa gcg att gaa tct aaa act aag gct<br>Ala Thr Lys Gly Asp Asp Lys Gln Ala Ile Glu Ser Lys Thr Lys Ala<br>580 585 590 | 1776 | |
| cta gaa gaa gca ttt gcg cca ata gct caa aaa gct tat gct gag caa<br>Leu Glu Glu Ala Phe Ala Pro Ile Ala Gln Lys Ala Tyr Ala Glu Gln<br>595 600 605 | 1824 | |
| gct caa gct gct gtt gcc caa ggt ggt gct aaa gct gaa gaa cct aag<br>Ala Gln Ala Ala Val Ala Gln Gly Gly Ala Lys Ala Glu Glu Pro Lys<br>610 615 620 | 1872 | |
| aaa gaa gaa gat gtt gtt gat gct gac ttt gag gat gtt gaa gac gac<br>Lys Glu Glu Asp Val Val Asp Ala Asp Phe Glu Asp Val Glu Asp Asp<br>625 630 635 640 | 1920 | |
| aaa aaa taa<br>Lys Lys | 1929 | |

<210> SEQ ID NO 6
<211> LENGTH: 642
<212> TYPE: PRT
<213> ORGANISM: Francisella tularensis

<400> SEQUENCE: 6

Met Gly Lys Ile Ile Gly Ile Asp Leu Gly Thr Thr Asn Ser Cys Leu
1               5                   10                  15

Ala Ile Met Asp Gly Lys Thr Ala Lys Val Ile Glu Asn Ala Glu Gly
            20                  25                  30

His Arg Thr Thr Pro Ser Val Val Ala Tyr Thr Asp Ser Gly Glu Ile
        35                  40                  45

Leu Val Gly Gln Ala Ala Lys Arg Gln Ala Val Thr Asn Pro Asp Asn
    50                  55                  60

Thr Phe Phe Ala Ile Lys Arg Leu Ile Gly Arg Lys Tyr Asp Asp Lys
65                  70                  75                  80

Ala Val Gln Glu Asp Ile Lys Lys Val Pro Tyr Ala Val Ile Lys
            85                  90                  95

Ala Asp Asn Gly Asp Ala Trp Val Ala Thr Lys Glu Gly Lys Lys Met
            100                 105                 110

Ala Pro Pro Gln Val Ser Ala Glu Val Leu Arg Lys Met Lys Lys Thr
        115                 120                 125

Ala Glu Asp Tyr Leu Gly Glu Pro Val Thr Glu Ala Val Ile Thr Val
    130                 135                 140

Pro Ala Tyr Phe Asn Asp Ser Gln Arg Gln Ala Thr Lys Asp Ala Gly
145                 150                 155                 160

Lys Ile Ala Gly Leu Glu Val Lys Arg Ile Ile Asn Glu Pro Thr Ala
                165                 170                 175

-continued

```
Ala Ala Leu Ala Tyr Gly Val Asp Ser Lys Lys Gly Glu Gln Thr Val
            180                 185                 190
Ala Val Tyr Asp Leu Gly Gly Gly Thr Phe Asp Ile Ser Ile Ile Glu
            195                 200                 205
Ile Ala Asp Val Asp Gly Asp Asn Gln Ile Glu Val Leu Ser Thr Asn
210                 215                 220
Gly Asp Thr Phe Leu Gly Gly Glu Asp Phe Asp Leu Ala Leu Met Asn
225                 230                 235                 240
Tyr Leu Ile Asp Glu Phe Lys Lys Glu Gln Gly Ile Asp Leu His Asn
            245                 250                 255
Asp Lys Leu Ala Leu Gln Arg Val Arg Glu Ala Ala Glu Lys Ala Lys
            260                 265                 270
Val Glu Leu Ser Ser Ala Gln Gln Thr Asp Val Asn Leu Pro Tyr Ile
            275                 280                 285
Thr Ala Asp Ala Thr Gly Pro Lys His Leu Asn Ile Lys Val Thr Arg
            290                 295                 300
Ala Lys Phe Glu Ser Leu Val Ser Asp Leu Val Met Arg Ser Leu Glu
305                 310                 315                 320
Pro Cys Lys Lys Ala Leu Glu Asp Ala Gly Leu Ser Lys Ser Asp Ile
            325                 330                 335
Thr Glu Val Leu Leu Val Gly Gly Gln Thr Arg Met Pro Leu Val Gln
            340                 345                 350
Glu Lys Val Lys Glu Phe Phe Gly Lys Glu Pro Arg Lys Asp Val Asn
            355                 360                 365
Pro Asp Glu Ala Val Ala Val Gly Ala Ala Ile Gln Gly Gly Val Leu
            370                 375                 380
Ala Gly Asp Val Lys Asp Ile Leu Leu Leu Asp Val Thr Pro Leu Ser
385                 390                 395                 400
Leu Gly Ile Glu Thr Met Gly Gly Val Met Thr Lys Leu Ile Glu Arg
            405                 410                 415
Asn Thr Thr Ile Pro Thr Lys Lys Ser Gln Val Phe Ser Thr Ala Glu
            420                 425                 430
Asp Asn Gln Pro Ala Val Thr Ile His Val Leu Gln Gly Glu Arg Glu
            435                 440                 445
Met Ala Ser Ala Asn Lys Ser Leu Gly Arg Phe Asp Leu Ala Asp Ile
450                 455                 460
Pro Pro Ala Pro Arg Gly Met Pro Gln Ile Glu Val Thr Phe Asp Ile
465                 470                 475                 480
Asp Ala Asn Gly Ile Leu Asn Val Ser Ala Lys Asp Lys Ala Thr Gly
            485                 490                 495
Lys Glu Gln Asn Ile Val Ile Lys Ser Ser Gly Leu Ser Glu Glu
            500                 505                 510
Asp Ile Glu Lys Met Val Gln Asp Ala Glu Ala Asn Ala Glu Ala Asp
            515                 520                 525
Lys Lys Phe His Asp Leu Val Thr Ala Arg Asn Thr Ala Asp Asn Leu
            530                 535                 540
Ile His Ser Ser Arg Lys Ala Ile Gln Glu Leu Gly Asp Lys Val Thr
545                 550                 555                 560
Ala Ala Glu Lys Glu Lys Ile Glu Glu Ala Cys Lys Glu Leu Glu Ala
            565                 570                 575
Ala Thr Lys Gly Asp Asp Lys Gln Ala Ile Glu Ser Lys Thr Lys Ala
            580                 585                 590
Leu Glu Glu Ala Phe Ala Pro Ile Ala Gln Lys Ala Tyr Ala Glu Gln
```

```
                    595                 600                 605
Ala Gln Ala Ala Val Ala Gln Gly Gly Ala Lys Ala Glu Pro Lys
                610                 615                 620

Lys Glu Glu Asp Val Val Asp Ala Asp Phe Glu Asp Val Glu Asp
625                 630                 635                 640

Lys Lys

<210> SEQ ID NO 7
<211> LENGTH: 921
<212> TYPE: DNA
<213> ORGANISM: Francisella tularensis
<220> FEATURE:
<221> NAME/KEY: CDS
<222> LOCATION: (1)..(921)

<400> SEQUENCE: 7 atg tca aaa aca gct gta gtt ttt cct ggt caa ggt tca caa aaa cta     48
Met Ser Lys Thr Ala Val Val Phe Pro Gly Gln Gly Ser Gln Lys Leu
1               5                   10                  15 ggg atg ctc caa gat tat tat gaa aat ttt gaa acg ttt aga aat ata     96
Gly Met Leu Gln Asp Tyr Tyr Glu Asn Phe Glu Thr Phe Arg Asn Ile
            20                  25                  30 gtc gat gaa gct aaa gaa cac ctt ggc tac gac tta tgg aat att att    144
Val Asp Glu Ala Lys Glu His Leu Gly Tyr Asp Leu Trp Asn Ile Ile
        35                  40                  45 caa aat gat gaa gaa act cta aat aaa aca gag ttt acc cag cca gca    192
Gln Asn Asp Glu Glu Thr Leu Asn Lys Thr Glu Phe Thr Gln Pro Ala
    50                  55                  60 tta ctt gca act agt tat gca ata tat gaa gtc tta aaa gag caa aag    240
Leu Leu Ala Thr Ser Tyr Ala Ile Tyr Glu Val Leu Lys Glu Gln Lys
65                  70                  75                  80 cca gac tta aaa ata gca tac ttt gca gga cat agt tta ggt gaa tac    288
Pro Asp Leu Lys Ile Ala Tyr Phe Ala Gly His Ser Leu Gly Glu Tyr
                85                  90                  95 act gcc cta ctt gct gct gga tgt att tca tac aaa gat gct tta caa    336
Thr Ala Leu Leu Ala Ala Gly Cys Ile Ser Tyr Lys Asp Ala Leu Gln
            100                 105                 110 ctt gta tct aca cgt ggc aaa tta atg caa aat gct gtt act gac aaa    384
Leu Val Ser Thr Arg Gly Lys Leu Met Gln Asn Ala Val Thr Asp Lys
        115                 120                 125 gaa tgt gct atg agc gca att cta ggt tta tca aat gag gat gta atc    432
Glu Cys Ala Met Ser Ala Ile Leu Gly Leu Ser Asn Glu Asp Val Ile
    130                 135                 140 aaa tct tgt caa gaa gct agt gat gct gga att gtt gaa gct gca aac    480
Lys Ser Cys Gln Glu Ala Ser Asp Ala Gly Ile Val Glu Ala Ala Asn
145                 150                 155                 160 ttt aac tca aca gga caa gtt gtc atc tct ggg gaa aaa gcc gct gtt    528
Phe Asn Ser Thr Gly Gln Val Val Ile Ser Gly Glu Lys Ala Ala Val
                165                 170                 175 gag aaa gct aat aca ata gct aaa gaa aaa ggt gca aaa cgc gcg cag    576
Glu Lys Ala Asn Thr Ile Ala Lys Glu Lys Gly Ala Lys Arg Ala Gln
            180                 185                 190 ata ctt gct gtt agc gta cct tca cat tgt tct tta atg aag gat gct    624
Ile Leu Ala Val Ser Val Pro Ser His Cys Ser Leu Met Lys Asp Ala
        195                 200                 205 gca gat aaa ttt gaa gca gag tta aac aaa gta gaa ttt aaa gag cct    672
Ala Asp Lys Phe Glu Ala Glu Leu Asn Lys Val Glu Phe Lys Glu Pro
    210                 215                 220 act acc gct gtt gta caa aac ttt gac gcc aaa tca cac gca aat cca    720
Thr Thr Ala Val Val Gln Asn Phe Asp Ala Lys Ser His Ala Asn Pro
225                 230                 235                 240
```

```
gct gaa ata aaa act gct gtt att aaa caa cta tac aag cca gta ctt    768
Ala Glu Ile Lys Thr Ala Val Ile Lys Gln Leu Tyr Lys Pro Val Leu
            245                 250                 255 tgg aca caa tct atc gaa gag cta gtc aaa ctt gga gtc aca gaa gtt    816
Trp Thr Gln Ser Ile Glu Glu Leu Val Lys Leu Gly Val Thr Glu Val
        260                 265                 270 atc gaa tgt ggt cct aac aag gtc tta tct gga cta atc aaa aga ata    864
Ile Glu Cys Gly Pro Asn Lys Val Leu Ser Gly Leu Ile Lys Arg Ile
    275                 280                 285 gat aaa tca ata gat ata aaa gat aca aac agt att gat agt tta gaa    912
Asp Lys Ser Ile Asp Ile Lys Asp Thr Asn Ser Ile Asp Ser Leu Glu
290                 295                 300 aat att taa                                                         921
Asn Ile
305
```

<210> SEQ ID NO 8
<211> LENGTH: 306
<212> TYPE: PRT
<213> ORGANISM: Francisella tularensis

<400> SEQUENCE: 8

```
Met Ser Lys Thr Ala Val Val Phe Pro Gly Gln Gly Ser Gln Lys Leu
1               5                   10                  15

Gly Met Leu Gln Asp Tyr Tyr Glu Asn Phe Glu Thr Phe Arg Asn Ile
            20                  25                  30

Val Asp Glu Ala Lys Glu His Leu Gly Tyr Asp Leu Trp Asn Ile Ile
        35                  40                  45

Gln Asn Asp Glu Glu Thr Leu Asn Lys Thr Glu Phe Thr Gln Pro Ala
    50                  55                  60

Leu Leu Ala Thr Ser Tyr Ala Ile Tyr Glu Val Leu Lys Glu Gln Lys
65                  70                  75                  80

Pro Asp Leu Lys Ile Ala Tyr Phe Ala Gly His Ser Leu Gly Glu Tyr
                85                  90                  95

Thr Ala Leu Leu Ala Ala Gly Cys Ile Ser Tyr Lys Asp Ala Leu Gln
            100                 105                 110

Leu Val Ser Thr Arg Gly Lys Leu Met Gln Asn Ala Val Thr Asp Lys
        115                 120                 125

Glu Cys Ala Met Ser Ala Ile Leu Gly Leu Ser Asn Glu Asp Val Ile
    130                 135                 140

Lys Ser Cys Gln Glu Ala Ser Asp Ala Gly Ile Val Glu Ala Ala Asn
145                 150                 155                 160

Phe Asn Ser Thr Gly Gln Val Val Ile Ser Gly Glu Lys Ala Ala Val
                165                 170                 175

Glu Lys Ala Asn Thr Ile Ala Lys Glu Lys Gly Ala Lys Arg Ala Gln
            180                 185                 190

Ile Leu Ala Val Ser Val Pro Ser His Cys Ser Leu Met Lys Asp Ala
        195                 200                 205

Ala Asp Lys Phe Glu Ala Glu Leu Asn Lys Val Glu Phe Lys Glu Pro
    210                 215                 220

Thr Thr Ala Val Val Gln Asn Phe Asp Ala Lys Ser His Ala Asn Pro
225                 230                 235                 240

Ala Glu Ile Lys Thr Ala Val Ile Lys Gln Leu Tyr Lys Pro Val Leu
                245                 250                 255

Trp Thr Gln Ser Ile Glu Glu Leu Val Lys Leu Gly Val Thr Glu Val
            260                 265                 270
```

| | | | | | | | | | | | | |
|---|---|---|---|---|---|---|---|---|---|---|---|---|
|Ile|Glu|Cys|Gly|Pro|Asn|Lys|Val|Leu|Ser|Gly|Leu|Ile|Lys|Arg|Ile|
| | |275| | | |280| | | |285| | | | | |
|Asp|Lys|Ser|Ile|Asp|Ile|Lys|Asp|Thr|Asn|Ser|Ile|Asp|Ser|Leu|Glu|
| |290| | | | |295| | | | |300| | | | |
|Asn|Ile| | | | | | | | | | | | | | |
|305| | | | | | | | | | | | | | | |

<210> SEQ ID NO 9
<211> LENGTH: 1638
<212> TYPE: DNA
<213> ORGANISM: Francisella tularensis
<220> FEATURE:
<221> NAME/KEY: CDS
<222> LOCATION: (1)..(1638)

<400> SEQUENCE: 9

```
atg gct gca aaa caa gtt tta ttt tca gat gaa gct cgt gca aaa atg      48
Met Ala Ala Lys Gln Val Leu Phe Ser Asp Glu Ala Arg Ala Lys Met
1               5                   10                  15 cta gat ggt gtt aac aca cta gca aat gct gta aaa gtt act tta ggt      96
Leu Asp Gly Val Asn Thr Leu Ala Asn Ala Val Lys Val Thr Leu Gly
            20                  25                  30 cca aaa ggt cgt aat gtt gtt tta gat aaa tca ttt ggc acg cct act     144
Pro Lys Gly Arg Asn Val Val Leu Asp Lys Ser Phe Gly Thr Pro Thr
        35                  40                  45 atc act aaa gat ggt gta tct gtt gct aaa gaa att gaa cta gaa gat     192
Ile Thr Lys Asp Gly Val Ser Val Ala Lys Glu Ile Glu Leu Glu Asp
    50                  55                  60 aag ttt gag aat atg ggt gct cag ata gtt aaa gaa gta gct tca aag     240
Lys Phe Glu Asn Met Gly Ala Gln Ile Val Lys Glu Val Ala Ser Lys
65                  70                  75                  80 aca gcg gat gtt gct ggt gat ggt act act aca gcg act gta ctt gct     288
Thr Ala Asp Val Ala Gly Asp Gly Thr Thr Thr Ala Thr Val Leu Ala
                85                  90                  95 cag gca tta ttg aca gag ggt cta aaa gct gtc gct gca ggt atg aat     336
Gln Ala Leu Leu Thr Glu Gly Leu Lys Ala Val Ala Ala Gly Met Asn
            100                 105                 110 cct atg gat cta aaa aga ggt atc gac aaa gca act gct agg tta gtt     384
Pro Met Asp Leu Lys Arg Gly Ile Asp Lys Ala Thr Ala Arg Leu Val
        115                 120                 125 gaa gaa tta aaa gca ctt tct aaa cca tgt tca gat cca aaa tca att     432
Glu Glu Leu Lys Ala Leu Ser Lys Pro Cys Ser Asp Pro Lys Ser Ile
    130                 135                 140 gag caa gtt ggt act atc tct gct aac tct gat gct act gta ggt aag     480
Glu Gln Val Gly Thr Ile Ser Ala Asn Ser Asp Ala Thr Val Gly Lys
145                 150                 155                 160 ctt atc gct gac gca atg gca aaa gtt ggt aaa gaa ggt gtg att aca     528
Leu Ile Ala Asp Ala Met Ala Lys Val Gly Lys Glu Gly Val Ile Thr
                165                 170                 175 gtt gaa gaa ggc aaa ggc ttt gaa gat gag ctt gat gta gtt gaa ggt     576
Val Glu Glu Gly Lys Gly Phe Glu Asp Glu Leu Asp Val Val Glu Gly
            180                 185                 190 atg cag ttt gat aga ggt tat cta tct ccg tat ttt gca aca aat caa     624
Met Gln Phe Asp Arg Gly Tyr Leu Ser Pro Tyr Phe Ala Thr Asn Gln
        195                 200                 205 gag aat atg act act gat tta gag aat cca tat att cta ata gtt gat     672
Glu Asn Met Thr Thr Asp Leu Glu Asn Pro Tyr Ile Leu Ile Val Asp
    210                 215                 220 aag aaa atc tct aat atc cgc gat tta tta ccg ata tta gaa ggt gtt     720
Lys Lys Ile Ser Asn Ile Arg Asp Leu Leu Pro Ile Leu Glu Gly Val
225                 230                 235                 240
```

```
tct aaa tct ggt aga gcg tta cta ata ata gct gaa gat gta gaa agt    768
Ser Lys Ser Gly Arg Ala Leu Leu Ile Ile Ala Glu Asp Val Glu Ser
        245                 250                 255 gaa gct cta gct act tta gtt gta aat aat atg cgt ggt gta gtt aaa    816
Glu Ala Leu Ala Thr Leu Val Val Asn Asn Met Arg Gly Val Val Lys
            260                 265                 270 gta tgt gct gtc aaa gct cct ggc ttt ggt gat aga aga aaa gct atg    864
Val Cys Ala Val Lys Ala Pro Gly Phe Gly Asp Arg Arg Lys Ala Met
        275                 280                 285 cta gaa gat atc gct act cta act gga gct acg ttt gta tca gaa gac    912
Leu Glu Asp Ile Ala Thr Leu Thr Gly Ala Thr Phe Val Ser Glu Asp
    290                 295                 300 cta agc atg aag tta gaa gaa act aac atg gag cat tta ggt acg gct    960
Leu Ser Met Lys Leu Glu Glu Thr Asn Met Glu His Leu Gly Thr Ala
305                 310                 315                 320 agt aga gta caa gta aca aaa gat aat aca aca att att gat ggt gct   1008
Ser Arg Val Gln Val Thr Lys Asp Asn Thr Thr Ile Ile Asp Gly Ala
            325                 330                 335 ggt gaa aaa gaa gct atc gct aaa cga ata aat gta atc aaa gct aat   1056
Gly Glu Lys Glu Ala Ile Ala Lys Arg Ile Asn Val Ile Lys Ala Asn
        340                 345                 350 att gct gaa gct aac tct gat tat gat cgt gag aag ctg caa gaa aga   1104
Ile Ala Glu Ala Asn Ser Asp Tyr Asp Arg Glu Lys Leu Gln Glu Arg
    355                 360                 365 ttg gct aaa ctt tct ggt ggt gtc gcg gtg ata aaa gtt ggt gct gtt   1152
Leu Ala Lys Leu Ser Gly Gly Val Ala Val Ile Lys Val Gly Ala Val
370                 375                 380 aca gaa gct gag atg aaa gag aag aaa gat cgt gtc gat gat gct tta   1200
Thr Glu Ala Glu Met Lys Glu Lys Lys Asp Arg Val Asp Asp Ala Leu
385                 390                 395                 400 cat gct act cgt gcg gct gta gaa gaa ggt att gtt gct ggt ggt ggc   1248
His Ala Thr Arg Ala Ala Val Glu Glu Gly Ile Val Ala Gly Gly Gly
            405                 410                 415 gtt gct tta att aga gca caa aaa gca tta gat ggc tta aca ggt gaa   1296
Val Ala Leu Ile Arg Ala Gln Lys Ala Leu Asp Gly Leu Thr Gly Glu
        420                 425                 430 aat gac gat caa aac tat ggt ata gcg cta ctt aga aaa gca ata gaa   1344
Asn Asp Asp Gln Asn Tyr Gly Ile Ala Leu Leu Arg Lys Ala Ile Glu
    435                 440                 445 gct cct cta aga cag ata gta tca aat gct ggc ggt gag tct tct gta   1392
Ala Pro Leu Arg Gln Ile Val Ser Asn Ala Gly Gly Glu Ser Ser Val
    450                 455                 460 gtt gtt aac caa gtt aaa gct aat caa ggt aac tat ggt tat aat gct   1440
Val Val Asn Gln Val Lys Ala Asn Gln Gly Asn Tyr Gly Tyr Asn Ala
465                 470                 475                 480 gca aat gat act tat ggt gat atg gtt gag atg ggt att tta gat cct   1488
Ala Asn Asp Thr Tyr Gly Asp Met Val Glu Met Gly Ile Leu Asp Pro
            485                 490                 495 act aaa gtt act cgt tca gct cta caa cat gct gct tca att gct gga   1536
Thr Lys Val Thr Arg Ser Ala Leu Gln His Ala Ala Ser Ile Ala Gly
        500                 505                 510 ctt atg atc act aca gag gcg atg atc ggt gag atc aaa gaa gct gct   1584
Leu Met Ile Thr Thr Glu Ala Met Ile Gly Glu Ile Lys Glu Ala Ala
    515                 520                 525 cct gct atg cct atg ggc ggt ggc atg ggc ggt atg cct ggc atg atg   1632
Pro Ala Met Pro Met Gly Gly Gly Met Gly Gly Met Pro Gly Met Met
    530                 535                 540 taa tag                                                           1638
```

<210> SEQ ID NO 10

```
<211> LENGTH: 544
<212> TYPE: PRT
<213> ORGANISM: Francisella tularensis

<400> SEQUENCE: 10

Met Ala Ala Lys Gln Val Leu Phe Ser Asp Glu Ala Arg Ala Lys Met
1               5                   10                  15

Leu Asp Gly Val Asn Thr Leu Ala Asn Ala Val Lys Val Thr Leu Gly
            20                  25                  30

Pro Lys Gly Arg Asn Val Val Leu Asp Lys Ser Phe Gly Thr Pro Thr
        35                  40                  45

Ile Thr Lys Asp Gly Val Ser Val Ala Lys Glu Ile Glu Leu Glu Asp
50                  55                  60

Lys Phe Glu Asn Met Gly Ala Gln Ile Val Lys Glu Val Ala Ser Lys
65                  70                  75                  80

Thr Ala Asp Val Ala Gly Asp Gly Thr Thr Thr Ala Thr Val Leu Ala
                85                  90                  95

Gln Ala Leu Leu Thr Glu Gly Leu Lys Ala Val Ala Ala Gly Met Asn
            100                 105                 110

Pro Met Asp Leu Lys Arg Gly Ile Asp Lys Ala Thr Ala Arg Leu Val
        115                 120                 125

Glu Glu Leu Lys Ala Leu Ser Lys Pro Cys Ser Asp Pro Lys Ser Ile
130                 135                 140

Glu Gln Val Gly Thr Ile Ser Ala Asn Ser Asp Ala Thr Val Gly Lys
145                 150                 155                 160

Leu Ile Ala Asp Ala Met Ala Lys Val Gly Lys Glu Gly Val Ile Thr
                165                 170                 175

Val Glu Glu Gly Lys Gly Phe Glu Asp Glu Leu Asp Val Val Glu Gly
            180                 185                 190

Met Gln Phe Asp Arg Gly Tyr Leu Ser Pro Tyr Phe Ala Thr Asn Gln
        195                 200                 205

Glu Asn Met Thr Thr Asp Leu Glu Asn Pro Tyr Ile Leu Ile Val Asp
210                 215                 220

Lys Lys Ile Ser Asn Ile Arg Asp Leu Leu Pro Ile Leu Glu Gly Val
225                 230                 235                 240

Ser Lys Ser Gly Arg Ala Leu Leu Ile Ile Ala Glu Asp Val Glu Ser
                245                 250                 255

Glu Ala Leu Ala Thr Leu Val Val Asn Asn Met Arg Gly Val Val Lys
            260                 265                 270

Val Cys Ala Val Lys Ala Pro Gly Phe Gly Asp Arg Arg Lys Ala Met
        275                 280                 285

Leu Glu Asp Ile Ala Thr Leu Thr Gly Ala Thr Phe Val Ser Glu Asp
290                 295                 300

Leu Ser Met Lys Leu Glu Glu Thr Asn Met Glu His Leu Gly Thr Ala
305                 310                 315                 320

Ser Arg Val Gln Val Thr Lys Asp Asn Thr Thr Ile Ile Asp Gly Ala
                325                 330                 335

Gly Glu Lys Glu Ala Ile Ala Lys Arg Ile Asn Val Ile Lys Ala Asn
            340                 345                 350

Ile Ala Glu Ala Asn Ser Asp Tyr Asp Arg Glu Lys Leu Gln Glu Arg
        355                 360                 365

Leu Ala Lys Leu Ser Gly Gly Val Ala Val Ile Lys Val Gly Ala Val
370                 375                 380

Thr Glu Ala Glu Met Lys Glu Lys Lys Asp Arg Val Asp Asp Ala Leu
385                 390                 395                 400
```

His Ala Thr Arg Ala Ala Val Glu Glu Gly Ile Val Ala Gly Gly Gly
                405                 410                 415

Val Ala Leu Ile Arg Ala Gln Lys Ala Leu Asp Gly Leu Thr Gly Glu
            420                 425                 430

Asn Asp Asp Gln Asn Tyr Gly Ile Ala Leu Leu Arg Lys Ala Ile Glu
        435                 440                 445

Ala Pro Leu Arg Gln Ile Val Ser Asn Ala Gly Gly Glu Ser Ser Val
    450                 455                 460

Val Val Asn Gln Val Lys Ala Asn Gln Gly Asn Tyr Gly Tyr Asn Ala
465                 470                 475                 480

Ala Asn Asp Thr Tyr Gly Asp Met Val Glu Met Gly Ile Leu Asp Pro
                485                 490                 495

Thr Lys Val Thr Arg Ser Ala Leu Gln His Ala Ala Ser Ile Ala Gly
            500                 505                 510

Leu Met Ile Thr Thr Glu Ala Met Ile Gly Glu Ile Lys Glu Ala Ala
        515                 520                 525

Pro Ala Met Pro Met Gly Gly Met Gly Gly Met Pro Gly Met Met
    530                 535                 540

<210> SEQ ID NO 11
<211> LENGTH: 633
<212> TYPE: DNA
<213> ORGANISM: Francisella tularensis
<220> FEATURE:
<221> NAME/KEY: CDS
<222> LOCATION: (1)..(633)

<400> SEQUENCE: 11

```
atg agt gag atg ata aca aga caa cag gta aca agt ggc gag acc att         48
Met Ser Glu Met Ile Thr Arg Gln Gln Val Thr Ser Gly Glu Thr Ile
1               5                   10                  15 cat gtg aga act gat cct act gca tgt ata gga tct cat cct aat tgt         96
His Val Arg Thr Asp Pro Thr Ala Cys Ile Gly Ser His Pro Asn Cys
            20                  25                  30 aga tta ttt att gat tct tta act ata gct ggg gag aaa ctt gat aaa        144
Arg Leu Phe Ile Asp Ser Leu Thr Ile Ala Gly Glu Lys Leu Asp Lys
        35                  40                  45 aat atc gtt gct ata gat ggt gga gag gat gtc acg aaa gct gat tcg        192
Asn Ile Val Ala Ile Asp Gly Gly Glu Asp Val Thr Lys Ala Asp Ser
    50                  55                  60 gct aca gct gct gct agt gta ata cgt tta tct ata acg cca ggc tct        240
Ala Thr Ala Ala Ala Ser Val Ile Arg Leu Ser Ile Thr Pro Gly Ser
65                  70                  75                  80 ata aat cca aca ata agt att act ctt ggt gtt cta att aaa tca aat        288
Ile Asn Pro Thr Ile Ser Ile Thr Leu Gly Val Leu Ile Lys Ser Asn
                85                  90                  95 gtt aga act aaa att gaa gag aaa gtt tcg agt ata tta caa gca agt        336
Val Arg Thr Lys Ile Glu Glu Lys Val Ser Ser Ile Leu Gln Ala Ser
            100                 105                 110 gct aca gat atg aaa att aag tta ggt aat tct aat aaa aaa caa gag        384
Ala Thr Asp Met Lys Ile Lys Leu Gly Asn Ser Asn Lys Lys Gln Glu
        115                 120                 125 tat aaa act gat gaa gca tgg ggt att atg ata gat cta tct aat tta        432
Tyr Lys Thr Asp Glu Ala Trp Gly Ile Met Ile Asp Leu Ser Asn Leu
    130                 135                 140 gag tta tat cca ata agt gct aag gct ttt agt att agt ata gag cca        480
Glu Leu Tyr Pro Ile Ser Ala Lys Ala Phe Ser Ile Ser Ile Glu Pro
145                 150                 155                 160 aca gaa ctt atg ggt gtt tca aaa gat gga atg aga tat cat att ata        528
Thr Glu Leu Met Gly Val Ser Lys Asp Gly Met Arg Tyr His Ile Ile
```

```
Thr Glu Leu Met Gly Val Ser Lys Asp Gly Met Arg Tyr His Ile Ile
            165                 170                 175 tct ata gat ggt ctt aca aca tct caa gga agt ttg cca gta tgt tgc        576
Ser Ile Asp Gly Leu Thr Thr Ser Gln Gly Ser Leu Pro Val Cys Cys
            180                 185                 190 gca gct agc aca gat aaa gga gtt gct aaa ata gga tat att gca gct        624
Ala Ala Ser Thr Asp Lys Gly Val Ala Lys Ile Gly Tyr Ile Ala Ala
            195                 200                 205 gca tag taa                                                             633
Ala

<210> SEQ ID NO 12
<211> LENGTH: 209
<212> TYPE: PRT
<213> ORGANISM: Francisella tularensis

<400> SEQUENCE: 12

Met Ser Glu Met Ile Thr Arg Gln Gln Val Thr Ser Gly Glu Thr Ile
1               5                   10                  15

His Val Arg Thr Asp Pro Thr Ala Cys Ile Gly Ser His Pro Asn Cys
            20                  25                  30

Arg Leu Phe Ile Asp Ser Leu Thr Ile Ala Gly Glu Lys Leu Asp Lys
        35                  40                  45

Asn Ile Val Ala Ile Asp Gly Gly Glu Asp Val Thr Lys Ala Asp Ser
    50                  55                  60

Ala Thr Ala Ala Ala Ser Val Ile Arg Leu Ser Ile Thr Pro Gly Ser
65                  70                  75                  80

Ile Asn Pro Thr Ile Ser Ile Thr Leu Gly Val Leu Ile Lys Ser Asn
                85                  90                  95

Val Arg Thr Lys Ile Glu Glu Lys Val Ser Ser Ile Leu Gln Ala Ser
            100                 105                 110

Ala Thr Asp Met Lys Ile Lys Leu Gly Asn Ser Asn Lys Lys Gln Glu
        115                 120                 125

Tyr Lys Thr Asp Glu Ala Trp Gly Ile Met Ile Asp Leu Ser Asn Leu
    130                 135                 140

Glu Leu Tyr Pro Ile Ser Ala Lys Ala Phe Ser Ile Ser Ile Glu Pro
145                 150                 155                 160

Thr Glu Leu Met Gly Val Ser Lys Asp Gly Met Arg Tyr His Ile Ile
                165                 170                 175

Ser Ile Asp Gly Leu Thr Thr Ser Gln Gly Ser Leu Pro Val Cys Cys
            180                 185                 190

Ala Ala Ser Thr Asp Lys Gly Val Ala Lys Ile Gly Tyr Ile Ala Ala
        195                 200                 205

Ala

<210> SEQ ID NO 13
<211> LENGTH: 2226
<212> TYPE: DNA
<213> ORGANISM: Francisella tularensis
<220> FEATURE:
<221> NAME/KEY: CDS
<222> LOCATION: (1)..(2226)

<400> SEQUENCE: 13 atg cta aag aaa att gta act gct tta gga atg tct gga atg cta cta        48
Met Leu Lys Lys Ile Val Thr Ala Leu Gly Met Ser Gly Met Leu Leu
1               5                   10                  15 gct tct agc aat gct atc gca gaa gat acc aca acg aaa aat gat aat        96
Ala Ser Ser Asn Ala Ile Ala Glu Asp Thr Thr Thr Lys Asn Asp Asn
```

|     |     |     |     |     |     |     |     |     |     |     |     |     |     |     |     |     |
|---|---|---|---|---|---|---|---|---|---|---|---|---|---|---|---|---|
|     |     |     | 20  |     |     |     | 25  |     |     |     | 30  |     |     |     |     |     |
| ctt | tca | cca | cag | agc | gta | gat | tta | tca | cca | ttg | cgc | aat | tta | aat | aag | 144 |
| Leu | Ser | Pro | Gln | Ser | Val | Asp | Leu | Ser | Pro | Leu | Arg | Asn | Leu | Asn | Lys |     |
|     |     |     | 35  |     |     |     | 40  |     |     |     | 45  |     |     |     |     |     |
| ctt | gat | agc | cca | atg | gat | aaa | gat | tat | aac | tat | cat | caa | gct | ttc | aaa | 192 |
| Leu | Asp | Ser | Pro | Met | Asp | Lys | Asp | Tyr | Asn | Tyr | His | Gln | Ala | Phe | Lys |     |
|     |     | 50  |     |     |     | 55  |     |     |     | 60  |     |     |     |     |     |     |
| aaa | cta | gat | act | gaa | cag | ctt | aaa | aaa | gat | atg | caa | gat | ctt | tta | acc | 240 |
| Lys | Leu | Asp | Thr | Glu | Gln | Leu | Lys | Lys | Asp | Met | Gln | Asp | Leu | Leu | Thr |     |
| 65  |     |     |     | 70  |     |     |     | 75  |     |     |     | 80  |     |     |     |     |
| cag | tca | caa | gac | tgg | tgg | cct | gct | gat | ttt | ggc | aat | tat | ggt | cct | ttc | 288 |
| Gln | Ser | Gln | Asp | Trp | Trp | Pro | Ala | Asp | Phe | Gly | Asn | Tyr | Gly | Pro | Phe |     |
|     |     |     |     | 85  |     |     |     | 90  |     |     |     | 95  |     |     |     |     |
| ttt | att | aga | cta | tcg | tgg | cat | gat | gct | ggt | aca | tac | aga | ata | tat | gat | 336 |
| Phe | Ile | Arg | Leu | Ser | Trp | His | Asp | Ala | Gly | Thr | Tyr | Arg | Ile | Tyr | Asp |     |
|     |     |     | 100 |     |     |     | 105 |     |     |     | 110 |     |     |     |     |     |
| ggc | aga | gga | ggc | gct | aat | cgt | gga | caa | caa | agg | ttc | tcc | cct | tta | aat | 384 |
| Gly | Arg | Gly | Gly | Ala | Asn | Arg | Gly | Gln | Gln | Arg | Phe | Ser | Pro | Leu | Asn |     |
|     |     | 115 |     |     |     | 120 |     |     |     | 125 |     |     |     |     |     |     |
| agc | tgg | cca | gat | aat | gtt | aat | ctt | gac | aaa | gca | agg | caa | ctt | tta | tgg | 432 |
| Ser | Trp | Pro | Asp | Asn | Val | Asn | Leu | Asp | Lys | Ala | Arg | Gln | Leu | Leu | Trp |     |
| 130 |     |     |     | 135 |     |     |     | 140 |     |     |     |     |     |     |     |     |
| cca | atc | aaa | caa | aaa | tat | ggt | gat | gct | gtt | tca | tgg | tct | gat | ttg | att | 480 |
| Pro | Ile | Lys | Gln | Lys | Tyr | Gly | Asp | Ala | Val | Ser | Trp | Ser | Asp | Leu | Ile |     |
| 145 |     |     |     | 150 |     |     |     | 155 |     |     |     | 160 |     |     |     |     |
| gtt | tta | gct | ggt | act | gtt | tct | tta | gaa | tca | atg | gga | atg | aag | cct | ata | 528 |
| Val | Leu | Ala | Gly | Thr | Val | Ser | Leu | Glu | Ser | Met | Gly | Met | Lys | Pro | Ile |     |
|     |     |     | 165 |     |     |     | 170 |     |     |     | 175 |     |     |     |     |     |
| ggg | ttt | gct | ttt | ggt | aga | gaa | gac | gac | tgg | caa | ggt | gat | gat | aca | aac | 576 |
| Gly | Phe | Ala | Phe | Gly | Arg | Glu | Asp | Asp | Trp | Gln | Gly | Asp | Asp | Thr | Asn |     |
|     |     |     | 180 |     |     |     | 185 |     |     |     | 190 |     |     |     |     |     |
| tgg | gga | cta | tca | cct | gaa | gag | ata | atg | tct | agt | aat | gta | aga | gat | ggc | 624 |
| Trp | Gly | Leu | Ser | Pro | Glu | Glu | Ile | Met | Ser | Ser | Asn | Val | Arg | Asp | Gly |     |
|     |     | 195 |     |     |     | 200 |     |     |     | 205 |     |     |     |     |     |     |
| aaa | ctt | gct | cct | gca | tac | gcc | gca | aca | caa | atg | ggg | cta | ata | tat | gta | 672 |
| Lys | Leu | Ala | Pro | Ala | Tyr | Ala | Ala | Thr | Gln | Met | Gly | Leu | Ile | Tyr | Val |     |
| 210 |     |     |     | 215 |     |     |     | 220 |     |     |     |     |     |     |     |     |
| aat | cca | gaa | ggt | cct | gat | ggt | aaa | cct | gat | atc | aaa | ggt | gca | gct | agt | 720 |
| Asn | Pro | Glu | Gly | Pro | Asp | Gly | Lys | Pro | Asp | Ile | Lys | Gly | Ala | Ala | Ser |     |
| 225 |     |     |     | 230 |     |     |     | 235 |     |     |     | 240 |     |     |     |     |
| gaa | att | cgt | cag | gcc | ttc | cga | gct | atg | ggg | atg | aca | gat | aaa | gaa | act | 768 |
| Glu | Ile | Arg | Gln | Ala | Phe | Arg | Ala | Met | Gly | Met | Thr | Asp | Lys | Glu | Thr |     |
|     |     |     | 245 |     |     |     | 250 |     |     |     | 255 |     |     |     |     |     |
| gtc | gcc | cta | att | gca | ggc | ggt | cat | aca | ttt | ggt | aaa | act | cat | ggt | gca | 816 |
| Val | Ala | Leu | Ile | Ala | Gly | Gly | His | Thr | Phe | Gly | Lys | Thr | His | Gly | Ala |     |
|     |     | 260 |     |     |     | 265 |     |     |     | 270 |     |     |     |     |     |     |
| gtt | cca | gag | gat | aaa | gtc | aaa | caa | gca | att | gga | cct | gct | cct | gat | aag | 864 |
| Val | Pro | Glu | Asp | Lys | Val | Lys | Gln | Ala | Ile | Gly | Pro | Ala | Pro | Asp | Lys |     |
|     | 275 |     |     |     | 280 |     |     |     | 285 |     |     |     |     |     |     |     |
| gcg | cct | att | gag | cag | caa | ggt | cta | ggc | tgg | cac | aat | agt | tat | ggc | act | 912 |
| Ala | Pro | Ile | Glu | Gln | Gln | Gly | Leu | Gly | Trp | His | Asn | Ser | Tyr | Gly | Thr |     |
|     | 290 |     |     |     | 295 |     |     |     | 300 |     |     |     |     |     |     |     |
| gga | aat | ggt | gat | gat | act | atg | ggt | agc | ggt | ctt | gaa | ggc | tct | tgg | act | 960 |
| Gly | Asn | Gly | Asp | Asp | Thr | Met | Gly | Ser | Gly | Leu | Glu | Gly | Ser | Trp | Thr |     |
| 305 |     |     |     | 310 |     |     |     | 315 |     |     |     | 320 |     |     |     |     |
| tct | act | cca | act | ttt | tgg | aat | cat | gat | ttc | tta | cat | aac | ctt | tac | aac | 1008 |
| Ser | Thr | Pro | Thr | Phe | Trp | Asn | His | Asp | Phe | Leu | His | Asn | Leu | Tyr | Asn |     |
|     |     |     |     | 325 |     |     |     | 330 |     |     |     | 335 |     |     |     |     |
| tta | gac | tgg | aag | aaa | aca | ctt | agc | cct | gct | gga | gct | cac | caa | tgg | act | 1056 |
| Leu | Asp | Trp | Lys | Lys | Thr | Leu | Ser | Pro | Ala | Gly | Ala | His | Gln | Trp | Thr |     |

```
                    340             345             350
cct aca aat gct aag cca gaa aat atg gtt cct gat gct cac aag ccg    1104
Pro Thr Asn Ala Lys Pro Glu Asn Met Val Pro Asp Ala His Lys Pro
        355             360             365 ggt gta aaa cat aaa cct ata atg ttt aca aca gac tta gcg cta aaa    1152
Gly Val Lys His Lys Pro Ile Met Phe Thr Thr Asp Leu Ala Leu Lys
    370             375             380 gaa gat gat gga ttt aat aaa tat act caa gag ttc tac aat aat cct    1200
Glu Asp Asp Gly Phe Asn Lys Tyr Thr Gln Glu Phe Tyr Asn Asn Pro
385             390             395             400 gaa gaa ttt aaa gaa gag ttt gct aaa gca tgg ttt aaa tta aca cat    1248
Glu Glu Phe Lys Glu Glu Phe Ala Lys Ala Trp Phe Lys Leu Thr His
            405             410             415 aga gat atg gga cca aaa tct aga tat ata ggt cct tgg att cct gag    1296
Arg Asp Met Gly Pro Lys Ser Arg Tyr Ile Gly Pro Trp Ile Pro Glu
        420             425             430 caa aac ttt att tgg cag gat cct gtt cca gca gca gac tat aag caa    1344
Gln Asn Phe Ile Trp Gln Asp Pro Val Pro Ala Ala Asp Tyr Lys Gln
    435             440             445 gtg tct aca caa gat att gcc caa ctt gag caa gat att ata aac tct    1392
Val Ser Thr Gln Asp Ile Ala Gln Leu Glu Gln Asp Ile Ile Asn Ser
450             455             460 gga tta act aat cag caa ctt ata aaa act gct tgg gat tca gct tct    1440
Gly Leu Thr Asn Gln Gln Leu Ile Lys Thr Ala Trp Asp Ser Ala Ser
465             470             475             480 act tat cgt aaa acc gac tat aga ggt ggc tca aat ggt gca agg att    1488
Thr Tyr Arg Lys Thr Asp Tyr Arg Gly Gly Ser Asn Gly Ala Arg Ile
            485             490             495 gct tta gct cca gag aaa gat tgg caa atg aat gaa cca gct aaa ctt    1536
Ala Leu Ala Pro Glu Lys Asp Trp Gln Met Asn Glu Pro Ala Lys Leu
        500             505             510 gaa gtt gtt ctt act aag ctt aaa gag att caa acc aac ttt aac aat    1584
Glu Val Val Leu Thr Lys Leu Lys Glu Ile Gln Thr Asn Phe Asn Asn
    515             520             525 agc aaa act gat ggt aca aaa gta tca ttg gct gac tta ata gtg cta    1632
Ser Lys Thr Asp Gly Thr Lys Val Ser Leu Ala Asp Leu Ile Val Leu
530             535             540 ggt ggt aat gtg ggt gtt gag caa gca gct aaa caa gct ggt tat aat    1680
Gly Gly Asn Val Gly Val Glu Gln Ala Ala Lys Gln Ala Gly Tyr Asn
545             550             555             560 ata caa atg cct ttt gta cca ggt aga aca gat gct act caa gct caa    1728
Ile Gln Met Pro Phe Val Pro Gly Arg Thr Asp Ala Thr Gln Ala Gln
            565             570             575 act gac ata gag tct ttc aac tat cta aaa acc aaa tct gat ggt ttt    1776
Thr Asp Ile Glu Ser Phe Asn Tyr Leu Lys Thr Lys Ser Asp Gly Phe
        580             585             590 ata aac tat aca gat ggt agt gta agt gct gat aaa tta cca cag act    1824
Ile Asn Tyr Thr Asp Gly Ser Val Ser Ala Asp Lys Leu Pro Gln Thr
    595             600             605 tta gta gaa aaa gct agc atg ctt gac tta aat atc cca gaa atg aca    1872
Leu Val Glu Lys Ala Ser Met Leu Asp Leu Asn Ile Pro Glu Met Thr
610             615             620 gtg tta gtc ggt ggt atg cgt gct ctt gat gtc aat tat gat aac tca    1920
Val Leu Val Gly Gly Met Arg Ala Leu Asp Val Asn Tyr Asp Asn Ser
625             630             635             640 caa gaa ggt gta tta act act act cca ggt cag ctt aat aat agc ttc    1968
Gln Glu Gly Val Leu Thr Thr Thr Pro Gly Gln Leu Asn Asn Ser Phe
            645             650             655 ttt gtg aac ttg cta gat atg tct act caa tgg aaa aaa tct gat aaa    2016
Phe Val Asn Leu Leu Asp Met Ser Thr Gln Trp Lys Lys Ser Asp Lys
```

|                                                                 |      |
|-----------------------------------------------------------------|------|
| 660 665 670                                                     |      |
| aaa gat ggt gag tat att ggt ata gat aga aaa act ggt aag caa aag | 2064 |
| Lys Asp Gly Glu Tyr Ile Gly Ile Asp Arg Lys Thr Gly Lys Gln Lys |      |
| 675 680 685                                                     |      |
| tgg aca gca tcg cca gtt gat cta att ttt gga tca aac tca gag ctt | 2112 |
| Trp Thr Ala Ser Pro Val Asp Leu Ile Phe Gly Ser Asn Ser Glu Leu |      |
| 690 695 700                                                     |      |
| aaa gca gta gct caa gtt tat gct gaa aat ggt aat gag caa aaa ttt | 2160 |
| Lys Ala Val Ala Gln Val Tyr Ala Glu Asn Gly Asn Glu Gln Lys Phe |      |
| 705 710 715 720                                                 |      |
| gta aat gac ttt gca aaa gct tgg cat aaa gtt atg atg ctt ggc aga | 2208 |
| Val Asn Asp Phe Ala Lys Ala Trp His Lys Val Met Met Leu Gly Arg |      |
| 725 730 735                                                     |      |
| ttt gat gtt caa caa taa                                         | 2226 |
| Phe Asp Val Gln Gln                                             |      |
| 740                                                             |      |

<210> SEQ ID NO 14
<211> LENGTH: 741
<212> TYPE: PRT
<213> ORGANISM: Francisella tularensis

<400> SEQUENCE: 14

Met Leu Lys Lys Ile Val Thr Ala Leu Gly Met Ser Gly Met Leu Leu
1               5                   10                  15

Ala Ser Ser Asn Ala Ile Ala Glu Asp Thr Thr Thr Lys Asn Asp Asn
                20                  25                  30

Leu Ser Pro Gln Ser Val Asp Leu Ser Pro Leu Arg Asn Leu Asn Lys
            35                  40                  45

Leu Asp Ser Pro Met Asp Lys Asp Tyr Asn Tyr His Gln Ala Phe Lys
        50                  55                  60

Lys Leu Asp Thr Glu Gln Leu Lys Lys Asp Met Gln Asp Leu Leu Thr
65                  70                  75                  80

Gln Ser Gln Asp Trp Pro Ala Asp Phe Gly Asn Tyr Gly Pro Phe
                85                  90                  95

Phe Ile Arg Leu Ser Trp His Asp Ala Gly Thr Tyr Arg Ile Tyr Asp
            100                 105                 110

Gly Arg Gly Gly Ala Asn Arg Gly Gln Gln Arg Phe Ser Pro Leu Asn
        115                 120                 125

Ser Trp Pro Asp Asn Val Asn Leu Asp Lys Ala Arg Gln Leu Leu Trp
    130                 135                 140

Pro Ile Lys Gln Lys Tyr Gly Asp Ala Val Ser Trp Ser Asp Leu Ile
145                 150                 155                 160

Val Leu Ala Gly Thr Val Ser Leu Glu Ser Met Gly Met Lys Pro Ile
                165                 170                 175

Gly Phe Ala Phe Gly Arg Glu Asp Asp Trp Gln Gly Asp Thr Asn
            180                 185                 190

Trp Gly Leu Ser Pro Glu Glu Ile Met Ser Ser Asn Val Arg Asp Gly
        195                 200                 205

Lys Leu Ala Pro Ala Tyr Ala Ala Thr Gln Met Gly Leu Ile Tyr Val
    210                 215                 220

Asn Pro Glu Gly Pro Asp Gly Lys Pro Asp Ile Lys Gly Ala Ala Ser
225                 230                 235                 240

Glu Ile Arg Gln Ala Phe Arg Ala Met Gly Met Thr Asp Lys Glu Thr
                245                 250                 255

Val Ala Leu Ile Ala Gly Gly His Thr Phe Gly Lys Thr His Gly Ala
            260                 265                 270

```
Val Pro Glu Asp Lys Val Lys Gln Ala Ile Gly Pro Ala Pro Asp Lys
        275                 280                 285
Ala Pro Ile Glu Gln Gln Gly Leu Gly Trp His Asn Ser Tyr Gly Thr
        290                 295                 300
Gly Asn Gly Asp Asp Thr Met Gly Ser Gly Leu Glu Gly Ser Trp Thr
305                 310                 315                 320
Ser Thr Pro Thr Phe Trp Asn His Asp Phe Leu His Asn Leu Tyr Asn
                325                 330                 335
Leu Asp Trp Lys Lys Thr Leu Ser Pro Ala Gly Ala His Gln Trp Thr
            340                 345                 350
Pro Thr Asn Ala Lys Pro Glu Asn Met Val Pro Asp Ala His Lys Pro
        355                 360                 365
Gly Val Lys His Lys Pro Ile Met Phe Thr Thr Asp Leu Ala Leu Lys
370                 375                 380
Glu Asp Asp Gly Phe Asn Lys Tyr Thr Gln Glu Phe Tyr Asn Asn Pro
385                 390                 395                 400
Glu Glu Phe Lys Glu Glu Phe Ala Lys Ala Trp Phe Lys Leu Thr His
                405                 410                 415
Arg Asp Met Gly Pro Lys Ser Arg Tyr Ile Gly Pro Trp Ile Pro Glu
            420                 425                 430
Gln Asn Phe Ile Trp Gln Asp Pro Val Pro Ala Ala Asp Tyr Lys Gln
        435                 440                 445
Val Ser Thr Gln Asp Ile Ala Gln Leu Glu Gln Asp Ile Ile Asn Ser
        450                 455                 460
Gly Leu Thr Asn Gln Gln Leu Ile Lys Thr Ala Trp Asp Ser Ala Ser
465                 470                 475                 480
Thr Tyr Arg Lys Thr Asp Tyr Arg Gly Gly Ser Asn Gly Ala Arg Ile
                485                 490                 495
Ala Leu Ala Pro Glu Lys Asp Trp Gln Met Asn Glu Pro Ala Lys Leu
            500                 505                 510
Glu Val Val Leu Thr Lys Leu Lys Glu Ile Gln Thr Asn Phe Asn Asn
        515                 520                 525
Ser Lys Thr Asp Gly Thr Lys Val Ser Leu Ala Asp Leu Ile Val Leu
        530                 535                 540
Gly Gly Asn Val Gly Val Glu Gln Ala Ala Lys Gln Ala Gly Tyr Asn
545                 550                 555                 560
Ile Gln Met Pro Phe Val Pro Gly Arg Thr Asp Ala Thr Gln Ala Gln
                565                 570                 575
Thr Asp Ile Glu Ser Phe Asn Tyr Leu Lys Thr Lys Ser Asp Gly Phe
            580                 585                 590
Ile Asn Tyr Thr Asp Gly Ser Val Ser Ala Asp Lys Leu Pro Gln Thr
        595                 600                 605
Leu Val Glu Lys Ala Ser Met Leu Asp Leu Asn Ile Pro Glu Met Thr
        610                 615                 620
Val Leu Val Gly Gly Met Arg Ala Leu Asp Val Asn Tyr Asp Asn Ser
625                 630                 635                 640
Gln Glu Gly Val Leu Thr Thr Pro Gly Gln Leu Asn Asn Ser Phe
                645                 650                 655
Phe Val Asn Leu Leu Asp Met Ser Thr Gln Trp Lys Lys Ser Asp Lys
            660                 665                 670
Lys Asp Gly Glu Tyr Ile Gly Ile Asp Arg Lys Thr Gly Lys Gln Lys
        675                 680                 685
Trp Thr Ala Ser Pro Val Asp Leu Ile Phe Gly Ser Asn Ser Glu Leu
```

-continued

```
                          690                 695                  700
Lys Ala Val Ala Gln Val Tyr Ala Glu Asn Gly Asn Glu Gln Lys Phe
705                     710                 715                  720

Val Asn Asp Phe Ala Lys Ala Trp His Lys Val Met Met Leu Gly Arg
                    725                 730                  735

Phe Asp Val Gln Gln
            740

<210> SEQ ID NO 15
<211> LENGTH: 1218
<212> TYPE: DNA
<213> ORGANISM: Francisella tularensis
<220> FEATURE:
<221> NAME/KEY: CDS
<222> LOCATION: (1)..(1218)

<400> SEQUENCE: 15 atg aga att tta ttt aca att tta gct ttt ttt gga tac agt tat ggg      48
Met Arg Ile Leu Phe Thr Ile Leu Ala Phe Phe Gly Tyr Ser Tyr Gly
1               5                  10                  15 tta gca cat gga att act aaa aca ata gta cac aac tat cct gaa aac      96
Leu Ala His Gly Ile Thr Lys Thr Ile Val His Asn Tyr Pro Glu Asn
            20                  25                  30 ata tca aaa tca ttt caa att agt aac aac aat tat gct cct tta caa     144
Ile Ser Lys Ser Phe Gln Ile Ser Asn Asn Asn Tyr Ala Pro Leu Gln
        35                  40                  45 att agt aaa cta atc cag agt gca aag aaa aat att gat att gaa gta     192
Ile Ser Lys Leu Ile Gln Ser Ala Lys Lys Asn Ile Asp Ile Glu Val
    50                  55                  60 ttc tac ata gat ata aaa aaa gac agt gtt cta gat aag atg ata att     240
Phe Tyr Ile Asp Ile Lys Lys Asp Ser Val Leu Asp Lys Met Ile Ile
65                  70                  75                  80 caa cct tta gca gca aag gct aat caa gga att aaa gtt aga att ttg     288
Gln Pro Leu Ala Ala Lys Ala Asn Gln Gly Ile Lys Val Arg Ile Leu
                85                  90                  95 gtg gat gac aaa ttt tat agc caa tac agc aac aac aaa gct agc tgt     336
Val Asp Asp Lys Phe Tyr Ser Gln Tyr Ser Asn Asn Lys Ala Ser Cys
            100                 105                 110 gat tat tta aac tct att aag aat ata act tgt aaa ccg aca aaa gaa     384
Asp Tyr Leu Asn Ser Ile Lys Asn Ile Thr Cys Lys Pro Thr Lys Glu
        115                 120                 125 ttt caa gaa gct gta atg cac tct aaa atg ata agc att gat ggt aag     432
Phe Gln Glu Ala Val Met His Ser Lys Met Ile Ser Ile Asp Gly Lys
    130                 135                 140 tct ttt tac att ggt agt cat aat ttt gat tgg ata aca ttt gaa ctt     480
Ser Phe Tyr Ile Gly Ser His Asn Phe Asp Trp Ile Thr Phe Glu Leu
145                 150                 155                 160 aat cat gag cta gga gtt att gtt aaa aat gat aag att aat gct gct     528
Asn His Glu Leu Gly Val Ile Val Lys Asn Asp Lys Ile Asn Ala Ala
                165                 170                 175 aaa ctt gaa aaa tct ttt aat gat gat tgg aac ttt act aat aaa agt     576
Lys Leu Glu Lys Ser Phe Asn Asp Asp Trp Asn Phe Thr Asn Lys Ser
            180                 185                 190 aaa aag cta aca gat aat aac ttg aat aca tac tca ctt cat gac caa     624
Lys Lys Leu Thr Asp Asn Asn Leu Asn Thr Tyr Ser Leu His Asp Gln
        195                 200                 205 gga aat caa gcg att gtg act gtt aca cct gat ata gat aaa aaa ggt     672
Gly Asn Gln Ala Ile Val Thr Val Thr Pro Asp Ile Asp Lys Lys Gly
    210                 215                 220 tac cct aaa agt aat cta aaa act ttc ata tca tta att aaa tct gca     720
Tyr Pro Lys Ser Asn Leu Lys Thr Phe Ile Ser Leu Ile Lys Ser Ala
```

```
                225                 230                 235                 240
aaa tca agt ata gta atc caa gca atg att gta tct gga ata gat cca        768
Lys Ser Ser Ile Val Ile Gln Ala Met Ile Val Ser Gly Ile Asp Pro
                245                 250                 255 tac atg aat gat aaa aac tgg gat gaa ttt aca aaa gcc tta tca gac        816
Tyr Met Asn Asp Lys Asn Trp Asp Glu Phe Thr Lys Ala Leu Ser Asp
                260                 265                 270 gct aat aaa cga aat gtt tat gta aaa att atg ttc tca aat tgg atg        864
Ala Asn Lys Arg Asn Val Tyr Val Lys Ile Met Phe Ser Asn Trp Met
                275                 280                 285 ttt acc aaa tct tcg tat aaa gat agt aat gat tgg cta caa aaa ctg        912
Phe Thr Lys Ser Ser Tyr Lys Asp Ser Asn Asp Trp Leu Gln Lys Leu
                290                 295                 300 att cat caa tca aat caa aat cac tta aag atc aaa tac aca tca tta        960
Ile His Gln Ser Asn Gln Asn His Leu Lys Ile Lys Tyr Thr Ser Leu
305                 310                 315                 320 ccc cat aca aaa caa tgt gta cca ttc tct gaa gta gat cat gca aaa       1008
Pro His Thr Lys Gln Cys Val Pro Phe Ser Glu Val Asp His Ala Lys
                325                 330                 335 tat gct att ttt gat ggt acc ata gca tgg gtt tct act tct aat ata       1056
Tyr Ala Ile Phe Asp Gly Thr Ile Ala Trp Val Ser Thr Ser Asn Ile
                340                 345                 350 caa aaa tcc tac ttc tat gcg gca aaa aac tat tca tac att gct gac       1104
Gln Lys Ser Tyr Phe Tyr Ala Ala Lys Asn Tyr Ser Tyr Ile Ala Asp
                355                 360                 365 gat aaa gac cta tca cgg caa ctg aca gat gtt ttt gag cag ctt tgg       1152
Asp Lys Asp Leu Ser Arg Gln Leu Thr Asp Val Phe Glu Gln Leu Trp
                370                 375                 380 gat agt aaa tat gct cat aca tat tcg caa cct gtt ggt ata ata tca       1200
Asp Ser Lys Tyr Ala His Thr Tyr Ser Gln Pro Val Gly Ile Ile Ser
385                 390                 395                 400 act ccg tct tgt acc taa                                               1218
Thr Pro Ser Cys Thr
                405

<210> SEQ ID NO 16
<211> LENGTH: 405
<212> TYPE: PRT
<213> ORGANISM: Francisella tularensis

<400> SEQUENCE: 16

Met Arg Ile Leu Phe Thr Ile Leu Ala Phe Gly Tyr Ser Tyr Gly
1               5                   10                  15

Leu Ala His Gly Ile Thr Lys Thr Ile Val His Asn Tyr Pro Glu Asn
                20                  25                  30

Ile Ser Lys Ser Phe Gln Ile Ser Asn Asn Tyr Ala Pro Leu Gln
            35                  40                  45

Ile Ser Lys Leu Ile Gln Ser Ala Lys Lys Asn Ile Asp Ile Glu Val
        50                  55                  60

Phe Tyr Ile Asp Ile Lys Lys Asp Ser Val Leu Asp Lys Met Ile Ile
65                  70                  75                  80

Gln Pro Leu Ala Ala Lys Ala Asn Gln Gly Ile Lys Val Arg Ile Leu
                85                  90                  95

Val Asp Asp Lys Phe Tyr Ser Gln Tyr Ser Asn Asn Lys Ala Ser Cys
            100                 105                 110

Asp Tyr Leu Asn Ser Ile Lys Asn Ile Thr Cys Lys Pro Thr Lys Glu
        115                 120                 125

Phe Gln Glu Ala Val Met His Ser Lys Met Ile Ser Ile Asp Gly Lys
    130                 135                 140
```

```
Ser Phe Tyr Ile Gly Ser His Asn Phe Asp Trp Ile Thr Phe Glu Leu
145                 150                 155                 160

Asn His Glu Leu Gly Val Ile Val Lys Asn Asp Lys Ile Asn Ala Ala
            165                 170                 175

Lys Leu Glu Lys Ser Phe Asn Asp Asp Trp Asn Phe Thr Asn Lys Ser
        180                 185                 190

Lys Lys Leu Thr Asp Asn Asn Leu Asn Thr Tyr Ser Leu His Asp Gln
    195                 200                 205

Gly Asn Gln Ala Ile Val Thr Val Thr Pro Asp Ile Asp Lys Lys Gly
210                 215                 220

Tyr Pro Lys Ser Asn Leu Lys Thr Phe Ile Ser Leu Ile Lys Ser Ala
225                 230                 235                 240

Lys Ser Ser Ile Val Ile Gln Ala Met Ile Val Ser Gly Ile Asp Pro
                245                 250                 255

Tyr Met Asn Asp Lys Asn Trp Asp Glu Phe Thr Lys Ala Leu Ser Asp
            260                 265                 270

Ala Asn Lys Arg Asn Val Tyr Val Lys Ile Met Phe Ser Asn Trp Met
        275                 280                 285

Phe Thr Lys Ser Ser Tyr Lys Asp Ser Asn Asp Trp Leu Gln Lys Leu
    290                 295                 300

Ile His Gln Ser Asn Gln Asn His Leu Lys Ile Lys Tyr Thr Ser Leu
305                 310                 315                 320

Pro His Thr Lys Gln Cys Val Pro Phe Ser Glu Val Asp His Ala Lys
                325                 330                 335

Tyr Ala Ile Phe Asp Gly Thr Ile Ala Trp Val Ser Thr Ser Asn Ile
            340                 345                 350

Gln Lys Ser Tyr Phe Tyr Ala Ala Lys Asn Tyr Ser Tyr Ile Ala Asp
        355                 360                 365

Asp Lys Asp Leu Ser Arg Gln Leu Thr Asp Val Phe Glu Gln Leu Trp
    370                 375                 380

Asp Ser Lys Tyr Ala His Thr Tyr Ser Gln Pro Val Gly Ile Ile Ser
385                 390                 395                 400

Thr Pro Ser Cys Thr
                405

<210> SEQ ID NO 17
<211> LENGTH: 579
<212> TYPE: DNA
<213> ORGANISM: Francisella tularensis
<220> FEATURE:
<221> NAME/KEY: CDS
<222> LOCATION: (1)..(579)

<400> SEQUENCE: 17 atg aaa ttt gaa tta cca aaa cta cct tac gct gtt gat gca tta gag        48
Met Lys Phe Glu Leu Pro Lys Leu Pro Tyr Ala Val Asp Ala Leu Glu
1               5                   10                  15 tca aca ata tca aaa gaa aca ata gag tat cac tat ggt aaa cat cat        96
Ser Thr Ile Ser Lys Glu Thr Ile Glu Tyr His Tyr Gly Lys His His
            20                  25                  30 caa aca tat gta act aat cta aat aat tta gtt gag ggt aca gag cac       144
Gln Thr Tyr Val Thr Asn Leu Asn Asn Leu Val Glu Gly Thr Glu His
        35                  40                  45 gat ggc aga aac cta gaa gaa atc gta aaa act tct aat ggc gga ata       192
Asp Gly Arg Asn Leu Glu Glu Ile Val Lys Thr Ser Asn Gly Gly Ile
    50                  55                  60 ttt aat aac gct gct caa gtt ttt aat cat act ttt tac tgg aat tgt       240
```

| | | | | | | | | | | | | | | | |
|---|---|---|---|---|---|---|---|---|---|---|---|---|---|---|---|
|Phe|Asn|Asn|Ala|Ala|Gln|Val|Phe|Asn|His|Thr|Phe|Tyr|Trp|Asn|Cys|
|65| | | |70| | | |75| | | |80| | | |

```
tta act cca aac aaa aca gaa gct tca agt cag tta aaa gca gca ttg    288
Leu Thr Pro Asn Lys Thr Glu Ala Ser Ser Gln Leu Lys Ala Ala Leu
            85                  90                  95 atc gag aca ttt ggt tct gta gaa aat ttt aaa gaa caa ttc tct aag    336
Ile Glu Thr Phe Gly Ser Val Glu Asn Phe Lys Glu Gln Phe Ser Lys
            100                 105                 110 gca gct att gca aca ttt ggt tct ggt tgg gct tgg tta gta aaa aat    384
Ala Ala Ile Ala Thr Phe Gly Ser Gly Trp Ala Trp Leu Val Lys Asn
            115                 120                 125 act gaa ggt aaa ctt gaa ata gta act aca agt aac gct ggt tgc cca    432
Thr Glu Gly Lys Leu Glu Ile Val Thr Thr Ser Asn Ala Gly Cys Pro
130                 135                 140 tta aca gag aac aaa aag cca ttg cta act ttt gat gtt tgg gag cac    480
Leu Thr Glu Asn Lys Lys Pro Leu Leu Thr Phe Asp Val Trp Glu His
145                 150                 155                 160 gca tac tat att gat tat cgt aat gct aga cct aaa tat gtt gaa gca    528
Ala Tyr Tyr Ile Asp Tyr Arg Asn Ala Arg Pro Lys Tyr Val Glu Ala
                165                 170                 175 tta tgg gat atc gta aac tgg caa ttt gtt tct gag caa ttc gct gat    576
Leu Trp Asp Ile Val Asn Trp Gln Phe Val Ser Glu Gln Phe Ala Asp
            180                 185                 190 tag                                                                579
```

<210> SEQ ID NO 18
<211> LENGTH: 192
<212> TYPE: PRT
<213> ORGANISM: Francisella tularensis

<400> SEQUENCE: 18

```
Met Lys Phe Glu Leu Pro Lys Leu Pro Tyr Ala Val Asp Ala Leu Glu
1               5                   10                  15

Ser Thr Ile Ser Lys Glu Thr Ile Glu Tyr His Tyr Gly Lys His His
            20                  25                  30

Gln Thr Tyr Val Thr Asn Leu Asn Asn Leu Val Glu Gly Thr Glu His
        35                  40                  45

Asp Gly Arg Asn Leu Glu Glu Ile Val Lys Thr Ser Asn Gly Gly Ile
    50                  55                  60

Phe Asn Asn Ala Ala Gln Val Phe Asn His Thr Phe Tyr Trp Asn Cys
65                  70                  75                  80

Leu Thr Pro Asn Lys Thr Glu Ala Ser Ser Gln Leu Lys Ala Ala Leu
                85                  90                  95

Ile Glu Thr Phe Gly Ser Val Glu Asn Phe Lys Glu Gln Phe Ser Lys
            100                 105                 110

Ala Ala Ile Ala Thr Phe Gly Ser Gly Trp Ala Trp Leu Val Lys Asn
        115                 120                 125

Thr Glu Gly Lys Leu Glu Ile Val Thr Thr Ser Asn Ala Gly Cys Pro
    130                 135                 140

Leu Thr Glu Asn Lys Lys Pro Leu Leu Thr Phe Asp Val Trp Glu His
145                 150                 155                 160

Ala Tyr Tyr Ile Asp Tyr Arg Asn Ala Arg Pro Lys Tyr Val Glu Ala
                165                 170                 175

Leu Trp Asp Ile Val Asn Trp Gln Phe Val Ser Glu Gln Phe Ala Asp
            180                 185                 190
```

<210> SEQ ID NO 19
<211> LENGTH: 1209

```
<212> TYPE: DNA
<213> ORGANISM: Francisella tularensis
<220> FEATURE:
<221> NAME/KEY: CDS
<222> LOCATION: (1)..(1209)

<400> SEQUENCE: 19 ttg gat ttt tgg tta att gtc gtc gta ttt gtg att tta tgc gtt tat      48
Leu Asp Phe Trp Leu Ile Val Val Val Phe Val Ile Leu Cys Val Tyr
 1               5                  10                  15 cta ata ata gaa aat ata gtg cat aat aat agt att aaa agt att cct      96
Leu Ile Ile Glu Asn Ile Val His Asn Asn Ser Ile Lys Ser Ile Pro
             20                  25                  30 att agg att cat gtc aat ggt act cgt ggt aag tca agt gtt gcg aga     144
Ile Arg Ile His Val Asn Gly Thr Arg Gly Lys Ser Ser Val Ala Arg
         35                  40                  45 ctt att gca gct ggt gtt aga gct gga gga tat aga aca gta gct aag     192
Leu Ile Ala Ala Gly Val Arg Ala Gly Gly Tyr Arg Thr Val Ala Lys
     50                  55                  60 act act gga act tta gca aga tat att gat gtt gat ggt tca gaa aca     240
Thr Thr Gly Thr Leu Ala Arg Tyr Ile Asp Val Asp Gly Ser Glu Thr
 65                  70                  75                  80 cct gta ttt aga ata ggt ttt agt aat att gct gag caa gtt aag att     288
Pro Val Phe Arg Ile Gly Phe Ser Asn Ile Ala Glu Gln Val Lys Ile
                 85                  90                  95 atg ttt aag gca aga aga gca aaa gct gat gct atc gtt atc gag tgt     336
Met Phe Lys Ala Arg Arg Ala Lys Ala Asp Ala Ile Val Ile Glu Cys
            100                 105                 110 atg gct ttg cag cca ctt ttg caa tcg ctg tgt gag tta aag ctt att     384
Met Ala Leu Gln Pro Leu Leu Gln Ser Leu Cys Glu Leu Lys Leu Ile
        115                 120                 125 aaa gcg aca cat gga gtt ttg aca aat gct cgt cct gat cat tta gat     432
Lys Ala Thr His Gly Val Leu Thr Asn Ala Arg Pro Asp His Leu Asp
    130                 135                 140 gtt atg ggt cct aca gaa aga gat gtt gca aaa gca tta gca gct act     480
Val Met Gly Pro Thr Glu Arg Asp Val Ala Lys Ala Leu Ala Ala Thr
145                 150                 155                 160 atc cct gtt gga gct aag tat ttt act gcg gaa gat atc cat tta gat     528
Ile Pro Val Gly Ala Lys Tyr Phe Thr Ala Glu Asp Ile His Leu Asp
                165                 170                 175 ttt ttt gaa tat gct tgt aaa gac cga ggc tca gaa cta atc gca gct     576
Phe Phe Glu Tyr Ala Cys Lys Asp Arg Gly Ser Glu Leu Ile Ala Ala
            180                 185                 190 aca gca caa gat gct gag aaa ata tct gat gaa gaa ata aat aag ttt     624
Thr Ala Gln Asp Ala Glu Lys Ile Ser Asp Glu Glu Ile Asn Lys Phe
        195                 200                 205 gta tac tca gaa ttt aag ata aat gtt gct cta gca tta aaa gta aca     672
Val Tyr Ser Glu Phe Lys Ile Asn Val Ala Leu Ala Leu Lys Val Thr
    210                 215                 220 gat gat ttg ggt ata cct aga gag atc gct ctt aaa gga atg tgg gaa     720
Asp Asp Leu Gly Ile Pro Arg Glu Ile Ala Leu Lys Gly Met Trp Glu
225                 230                 235                 240 gcg acc cca gat cca ggt gcg atg acg gag tat aat ttt aat att aaa     768
Ala Thr Pro Asp Pro Gly Ala Met Thr Glu Tyr Asn Phe Asn Ile Lys
                245                 250                 255 aat gct gaa ata aat ttt gct aat gct ttt gct gct aat gat cct gta     816
Asn Ala Glu Ile Asn Phe Ala Asn Ala Phe Ala Ala Asn Asp Pro Val
            260                 265                 270 tca aca aaa atg ctt tgg gat aag ctt tgt gct aag tat tca ggc tgt     864
Ser Thr Lys Met Leu Trp Asp Lys Leu Cys Ala Lys Tyr Ser Gly Cys
        275                 280                 285
```

```
gat aag aaa gta ttg gtt gtt aac tgt aga gat gat aga gag gat cgc    912
Asp Lys Lys Val Leu Val Val Asn Cys Arg Asp Asp Arg Glu Asp Arg
    290                 295                 300 tca aaa caa atg gca gaa gca gct cta ggt tgg caa aaa caa gat tta    960
Ser Lys Gln Met Ala Glu Ala Ala Leu Gly Trp Gln Lys Gln Asp Leu
305                 310                 315                 320 att gtt cta ata ggt act ggt aca gag gtt ttt act tcg ttt tat aaa   1008
Ile Val Leu Ile Gly Thr Gly Thr Glu Val Phe Thr Ser Phe Tyr Lys
                325                 330                 335 aaa tat gca aaa tca ctt aat aaa cca atg act aaa gtc ata gtt tgt   1056
Lys Tyr Ala Lys Ser Leu Asn Lys Pro Met Thr Lys Val Ile Val Cys
            340                 345                 350 gaa gag atg aca cct ata caa ata ctt gaa aaa aca gtt gat tca aat   1104
Glu Glu Met Thr Pro Ile Gln Ile Leu Glu Lys Thr Val Asp Ser Asn
                355                 360                 365 cca gca aac tct tat att ctt gtt gga gtt ggt aat att aaa gat att   1152
Pro Ala Asn Ser Tyr Ile Leu Val Gly Val Gly Asn Ile Lys Asp Ile
370                 375                 380 ggt atg gaa tta gtt gat tac tgt gat act agc cat aaa aag aag cat   1200
Gly Met Glu Leu Val Asp Tyr Cys Asp Thr Ser His Lys Lys Lys His
385                 390                 395                 400 aat tta tag                                                        1209
Asn Leu

<210> SEQ ID NO 20
<211> LENGTH: 402
<212> TYPE: PRT
<213> ORGANISM: Francisella tularensis

<400> SEQUENCE: 20

Leu Asp Phe Trp Leu Ile Val Val Phe Val Ile Leu Cys Val Tyr
 1               5                   10                  15

Leu Ile Ile Glu Asn Ile Val His Asn Asn Ser Ile Lys Ser Ile Pro
                20                  25                  30

Ile Arg Ile His Val Asn Gly Thr Arg Gly Lys Ser Ser Val Ala Arg
            35                  40                  45

Leu Ile Ala Ala Gly Val Arg Ala Gly Gly Tyr Arg Thr Val Ala Lys
        50                  55                  60

Thr Thr Gly Thr Leu Ala Arg Tyr Ile Asp Val Asp Gly Ser Glu Thr
65                  70                  75                  80

Pro Val Phe Arg Ile Gly Phe Ser Asn Ile Ala Glu Gln Val Lys Ile
                85                  90                  95

Met Phe Lys Ala Arg Arg Ala Lys Ala Asp Ala Ile Val Ile Glu Cys
            100                 105                 110

Met Ala Leu Gln Pro Leu Leu Gln Ser Leu Cys Glu Leu Lys Leu Ile
        115                 120                 125

Lys Ala Thr His Gly Val Leu Thr Asn Ala Arg Pro Asp His Leu Asp
    130                 135                 140

Val Met Gly Pro Thr Glu Arg Asp Val Ala Lys Ala Leu Ala Ala Thr
145                 150                 155                 160

Ile Pro Val Gly Ala Lys Tyr Phe Thr Ala Glu Asp Ile His Leu Asp
                165                 170                 175

Phe Phe Glu Tyr Ala Cys Lys Asp Arg Gly Ser Glu Leu Ile Ala Ala
            180                 185                 190

Thr Ala Gln Asp Ala Glu Lys Ile Ser Asp Glu Glu Ile Asn Lys Phe
        195                 200                 205

Val Tyr Ser Glu Phe Lys Ile Asn Val Ala Leu Ala Leu Lys Val Thr
    210                 215                 220
```

```
Asp Asp Leu Gly Ile Pro Arg Glu Ile Ala Leu Lys Gly Met Trp Glu
225                 230                 235                 240

Ala Thr Pro Asp Pro Gly Ala Met Thr Glu Tyr Asn Phe Asn Ile Lys
            245                 250                 255

Asn Ala Glu Ile Asn Phe Ala Asn Ala Phe Ala Ala Asn Asp Pro Val
        260                 265                 270

Ser Thr Lys Met Leu Trp Asp Lys Leu Cys Ala Lys Tyr Ser Gly Cys
    275                 280                 285

Asp Lys Lys Val Leu Val Val Asn Cys Arg Asp Asp Arg Glu Asp Arg
290                 295                 300

Ser Lys Gln Met Ala Glu Ala Ala Leu Gly Trp Gln Lys Gln Asp Leu
305                 310                 315                 320

Ile Val Leu Ile Gly Thr Gly Thr Glu Val Phe Thr Ser Phe Tyr Lys
                325                 330                 335

Lys Tyr Ala Lys Ser Leu Asn Lys Pro Met Thr Lys Val Ile Val Cys
            340                 345                 350

Glu Glu Met Thr Pro Ile Gln Ile Leu Glu Lys Thr Val Asp Ser Asn
        355                 360                 365

Pro Ala Asn Ser Tyr Ile Leu Val Gly Val Gly Asn Ile Lys Asp Ile
    370                 375                 380

Gly Met Glu Leu Val Asp Tyr Cys Asp Thr Ser His Lys Lys Lys His
385                 390                 395                 400

Asn Leu

<210> SEQ ID NO 21
<211> LENGTH: 591
<212> TYPE: DNA
<213> ORGANISM: Francisella tularensis
<220> FEATURE:
<221> NAME/KEY: CDS
<222> LOCATION: (1)..(591)

<400> SEQUENCE: 21 ttg ctt ata agg tgt tgt gaa aaa aag gac aat aag atg gca aaa aat      48
Leu Leu Ile Arg Cys Cys Glu Lys Lys Asp Asn Lys Met Ala Lys Asn
1               5                   10                  15 aaa atc cca aat tca agg ttg atg ata aat tat gaa act aat gtt gat      96
Lys Ile Pro Asn Ser Arg Leu Met Ile Asn Tyr Glu Thr Asn Val Asp
            20                  25                  30 ggt gtc tta aag aaa aaa gag cta cct tac aga gtc cta gtt gtt ggc     144
Gly Val Leu Lys Lys Lys Glu Leu Pro Tyr Arg Val Leu Val Val Gly
        35                  40                  45 gat tta tca aaa gga aga tct gtg gat gca aaa aaa gag ttc gca gat     192
Asp Leu Ser Lys Gly Arg Ser Val Asp Ala Lys Lys Glu Phe Ala Asp
    50                  55                  60 aga gag gtc aga aga gta aat aat ggt gtt gat agg gtt tta gaa gag     240
Arg Glu Val Arg Arg Val Asn Asn Gly Val Asp Arg Val Leu Glu Glu
65                  70                  75                  80 atg aat ata tct ttt gat ttt gag gca cca aac ttt gtt tct aaa gat     288
Met Asn Ile Ser Phe Asp Phe Glu Ala Pro Asn Phe Val Ser Lys Asp
                85                  90                  95 cgt agt aat tta aaa gtt aat tat aga att gaa agt gtc aaa gat ttt     336
Arg Ser Asn Leu Lys Val Asn Tyr Arg Ile Glu Ser Val Lys Asp Phe
            100                 105                 110 aga cct gat gct gtt gct aaa aaa gtt cct gaa atc aga gcg ctg ctt     384
Arg Pro Asp Ala Val Ala Lys Lys Val Pro Glu Ile Arg Ala Leu Leu
        115                 120                 125 gaa atg aaa gag ata tta gca tcc ttt gct aag gac att gaa aat aat     432
```

```
Glu Met Lys Glu Ile Leu Ala Ser Phe Ala Lys Asp Ile Glu Asn Asn
        130                 135                 140 cgt aat ctc aag aaa acc ata gat atg att ttt tca gat agt aac gaa      480
Arg Asn Leu Lys Lys Thr Ile Asp Met Ile Phe Ser Asp Ser Asn Glu
145                 150                 155                 160 tta gaa tca tta aag agt aag att cct gct ttg aca aac tat acg att      528
Leu Glu Ser Leu Lys Ser Lys Ile Pro Ala Leu Thr Asn Tyr Thr Ile
                165                 170                 175 aaa gac tct tgt gat gct gct gag tct caa gac tta agt aat caa caa      576
Lys Asp Ser Cys Asp Ala Ala Glu Ser Gln Asp Leu Ser Asn Gln Gln
            180                 185                 190 gta gat ggt aag tag                                                   591
Val Asp Gly Lys
        195

<210> SEQ ID NO 22
<211> LENGTH: 196
<212> TYPE: PRT
<213> ORGANISM: Francisella tularensis

<400> SEQUENCE: 22

Leu Leu Ile Arg Cys Cys Glu Lys Lys Asp Asn Lys Met Ala Lys Asn
1               5                   10                  15

Lys Ile Pro Asn Ser Arg Leu Met Ile Asn Tyr Glu Thr Asn Val Asp
            20                  25                  30

Gly Val Leu Lys Lys Lys Glu Leu Pro Tyr Arg Val Leu Val Val Gly
        35                  40                  45

Asp Leu Ser Lys Gly Arg Ser Val Asp Ala Lys Lys Glu Phe Ala Asp
    50                  55                  60

Arg Glu Val Arg Arg Val Asn Asn Gly Val Asp Arg Val Leu Glu Glu
65                  70                  75                  80

Met Asn Ile Ser Phe Asp Phe Glu Ala Pro Asn Phe Val Ser Lys Asp
                85                  90                  95

Arg Ser Asn Leu Lys Val Asn Tyr Arg Ile Glu Ser Val Lys Asp Phe
            100                 105                 110

Arg Pro Asp Ala Val Ala Lys Lys Val Pro Glu Ile Arg Ala Leu Leu
        115                 120                 125

Glu Met Lys Glu Ile Leu Ala Ser Phe Ala Lys Asp Ile Glu Asn Asn
    130                 135                 140

Arg Asn Leu Lys Lys Thr Ile Asp Met Ile Phe Ser Asp Ser Asn Glu
145                 150                 155                 160

Leu Glu Ser Leu Lys Ser Lys Ile Pro Ala Leu Thr Asn Tyr Thr Ile
                165                 170                 175

Lys Asp Ser Cys Asp Ala Ala Glu Ser Gln Asp Leu Ser Asn Gln Gln
            180                 185                 190

Val Asp Gly Lys
        195

<210> SEQ ID NO 23
<211> LENGTH: 1545
<212> TYPE: DNA
<213> ORGANISM: Francisella tularensis
<220> FEATURE:
<221> NAME/KEY: CDS
<222> LOCATION: (1)..(1545)

<400> SEQUENCE: 23 atg gta agt agg gag gat ttt att atg aca ata aat aaa tta agt ctc       48
Met Val Ser Arg Glu Asp Phe Ile Met Thr Ile Asn Lys Leu Ser Leu
1               5                   10                  15
```

| | | |
|---|---|---|
| act gat gaa ctt tta aat aat ttt ggg gga tct aca gaa gtt gat agt<br>Thr Asp Glu Leu Leu Asn Asn Phe Gly Gly Ser Thr Glu Val Asp Ser<br>20 25 30 | 96 | |
| gta ctc aaa aat ata gat ttt gat gtt tca gat gat gct tct aaa gtt<br>Val Leu Lys Asn Ile Asp Phe Asp Val Ser Asp Asp Ala Ser Lys Val<br>35 40 45 | 144 | |
| tta tct tta tct act gac tac aat gct aga aac ctt atg gcg cta tct<br>Leu Ser Leu Ser Thr Asp Tyr Asn Ala Arg Asn Leu Met Ala Leu Ser<br>50 55 60 | 192 | |
| ttg gta tta gca aat aat gat aat ata aat tat aat caa aaa tat<br>Leu Val Leu Ala Asn Asn Asp Asn Ile Asn Asn Tyr Asn Gln Lys Tyr<br>65 70 75 80 | 240 | |
| atc cag aaa gtt att aca gtt att gat aag ctt att gat tta caa gtt<br>Ile Gln Lys Val Ile Thr Val Ile Asp Lys Leu Ile Asp Leu Gln Val<br>85 90 95 | 288 | |
| aat tct att ata tct aat gat gag ttt aga gca ctt gag caa gaa tgg<br>Asn Ser Ile Ile Ser Asn Asp Glu Phe Arg Ala Leu Glu Gln Glu Trp<br>100 105 110 | 336 | |
| cta aag gtg caa gag gtt tgt caa gaa gac tat gat aat gtt gaa gta<br>Leu Lys Val Gln Glu Val Cys Gln Glu Asp Tyr Asp Asn Val Glu Val<br>115 120 125 | 384 | |
| agt ata tta gat gta aaa aaa gaa gag cta caa tat gat ttc gag aga<br>Ser Ile Leu Asp Val Lys Lys Glu Glu Leu Gln Tyr Asp Phe Glu Arg<br>130 135 140 | 432 | |
| aat tta tat gat ata tct agt agt gac ttt ttc aaa aaa gtt tac gtt<br>Asn Leu Tyr Asp Ile Ser Ser Ser Asp Phe Phe Lys Lys Val Tyr Val<br>145 150 155 160 | 480 | |
| tca gaa ttt gat caa tat ggt ggc gaa cct tat ggc gca ata tta gga<br>Ser Glu Phe Asp Gln Tyr Gly Gly Glu Pro Tyr Gly Ala Ile Leu Gly<br>165 170 175 | 528 | |
| ttg tat aat ttt gaa aat acc aca aat gat ata att tgg ttg act gga<br>Leu Tyr Asn Phe Glu Asn Thr Thr Asn Asp Ile Ile Trp Leu Thr Gly<br>180 185 190 | 576 | |
| atg ggt atg gtg gca aag aat tct cat gca cca ttt att gca tca att<br>Met Gly Met Val Ala Lys Asn Ser His Ala Pro Phe Ile Ala Ser Ile<br>195 200 205 | 624 | |
| gat aag tca ttc ttt ggt gtt aag gat tta tca gaa atc act cat ata<br>Asp Lys Ser Phe Phe Gly Val Lys Asp Leu Ser Glu Ile Thr His Ile<br>210 215 220 | 672 | |
| aaa agt ttt gaa gct ttg ctt gag cat cct aga tat aaa gag tgg aat<br>Lys Ser Phe Glu Ala Leu Leu Glu His Pro Arg Tyr Lys Glu Trp Asn<br>225 230 235 240 | 720 | |
| gat ttt aga aac ctt gat gtt gct gca tat ata ggt ttg acc gta ggt<br>Asp Phe Arg Asn Leu Asp Val Ala Ala Tyr Ile Gly Leu Thr Val Gly<br>245 250 255 | 768 | |
| gat ttt atg ttg cgg caa cca tat aat cct gag aat aat cca gtt cag<br>Asp Phe Met Leu Arg Gln Pro Tyr Asn Pro Glu Asn Asn Pro Val Gln<br>260 265 270 | 816 | |
| tat aaa ctt atg gaa ggc ttt aat gag ttt gtt gat tat gat aag aat<br>Tyr Lys Leu Met Glu Gly Phe Asn Glu Phe Val Asp Tyr Asp Lys Asn<br>275 280 285 | 864 | |
| gaa agt tat cta tgg gga cct gct tca att cat cta gtt aag aat atg<br>Glu Ser Tyr Leu Trp Gly Pro Ala Ser Ile His Leu Val Lys Asn Met<br>290 295 300 | 912 | |
| atg aga tct tat gat aaa act aga tgg ttc caa tat ata aga gga gtt<br>Met Arg Ser Tyr Asp Lys Thr Arg Trp Phe Gln Tyr Ile Arg Gly Val<br>305 310 315 320 | 960 | |
| gag agt ggt ggt tat gta aag aac ttg gta gct tgc gta tat gat aat<br>Glu Ser Gly Gly Tyr Val Lys Asn Leu Val Ala Cys Val Tyr Asp Asn<br>325 330 335 | 1008 | |

| | | | | | | | | | | | | | | | | |
|---|---|---|---|---|---|---|---|---|---|---|---|---|---|---|---|---|
| aaa | ggc | att | cta | gaa | act | aag | tca | cct | tta | aat | gta | tta | ttc | gct | gat | 1056 |
| Lys | Gly | Ile | Leu | Glu | Thr | Lys | Ser | Pro | Leu | Asn | Val | Leu | Phe | Ala | Asp | |
| | | | 340 | | | | 345 | | | | | 350 | | | | |
| tat | atg | gag | tta | tca | ctt | gca | aat | att | ggt | tta | ata | cca | ttt | gta | agt | 1104 |
| Tyr | Met | Glu | Leu | Ser | Leu | Ala | Asn | Ile | Gly | Leu | Ile | Pro | Phe | Val | Ser | |
| | | 355 | | | | | 360 | | | | | 365 | | | | |
| gaa | aaa | ggt | act | agt | aac | gct | tgt | ttc | ttt | agt | gta | aat | tct | gct | aaa | 1152 |
| Glu | Lys | Gly | Thr | Ser | Asn | Ala | Cys | Phe | Phe | Ser | Val | Asn | Ser | Ala | Lys | |
| | 370 | | | | | 375 | | | | | 380 | | | | | |
| aaa | gtc | gaa | gaa | ttt | gta | gat | gga | ttt | gac | tca | gca | aac | tca | aga | tta | 1200 |
| Lys | Val | Glu | Glu | Phe | Val | Asp | Gly | Phe | Asp | Ser | Ala | Asn | Ser | Arg | Leu | |
| 385 | | | | | 390 | | | | | 395 | | | | | 400 | |
| att | gct | aac | ctt | tct | tac | act | atg | tgt | ata | tcg | aga | ata | tct | cat | tat | 1248 |
| Ile | Ala | Asn | Leu | Ser | Tyr | Thr | Met | Cys | Ile | Ser | Arg | Ile | Ser | His | Tyr | |
| | | | | 405 | | | | | 410 | | | | | 415 | | |
| att | aaa | tgt | gta | att | aga | gat | aag | att | ggt | agt | att | gtg | gat | gtc | gag | 1296 |
| Ile | Lys | Cys | Val | Ile | Arg | Asp | Lys | Ile | Gly | Ser | Ile | Val | Asp | Val | Glu | |
| | | | 420 | | | | | 425 | | | | | 430 | | | |
| tcg | att | caa | aaa | att | ctt | tct | gat | tgg | ata | tca | gaa | ttt | gtc | acc | aca | 1344 |
| Ser | Ile | Gln | Lys | Ile | Leu | Ser | Asp | Trp | Ile | Ser | Glu | Phe | Val | Thr | Thr | |
| | | | 435 | | | | | 440 | | | | | 445 | | | |
| gtc | tat | caa | cca | acc | cct | tta | gaa | atg | gcg | aga | tat | cct | ttc | aga | aac | 1392 |
| Val | Tyr | Gln | Pro | Thr | Pro | Leu | Glu | Met | Ala | Arg | Tyr | Pro | Phe | Arg | Asn | |
| | 450 | | | | | 455 | | | | | 460 | | | | | |
| gtt | tct | atc | gag | gtt | gaa | acc | ata | ccg | ggt | aag | cct | ggc | tgg | tat | tca | 1440 |
| Val | Ser | Ile | Glu | Val | Glu | Thr | Ile | Pro | Gly | Lys | Pro | Gly | Trp | Tyr | Ser | |
| 465 | | | | | 470 | | | | | 475 | | | | | 480 | |
| tgc | aaa | ata | aat | gta | att | ccc | cac | att | caa | ttt | gaa | gga | atg | aat | act | 1488 |
| Cys | Lys | Ile | Asn | Val | Ile | Pro | His | Ile | Gln | Phe | Glu | Gly | Met | Asn | Thr | |
| | | | | 485 | | | | | 490 | | | | | 495 | | |
| aca | atg | act | ata | gat | act | agg | ctt | gaa | cca | gaa | tta | ttc | ggt | aca | aat | 1536 |
| Thr | Met | Thr | Ile | Asp | Thr | Arg | Leu | Glu | Pro | Glu | Leu | Phe | Gly | Thr | Asn | |
| | | | | 500 | | | | | 505 | | | | | 510 | | |
| aat | aac | taa | | | | | | | | | | | | | | 1545 |
| Asn | Asn | | | | | | | | | | | | | | | |

<210> SEQ ID NO 24
<211> LENGTH: 514
<212> TYPE: PRT
<213> ORGANISM: Francisella tularensis

<400> SEQUENCE: 24

Met Val Ser Arg Glu Asp Phe Ile Met Thr Ile Asn Lys Leu Ser Leu
1               5                   10                  15

Thr Asp Glu Leu Leu Asn Asn Phe Gly Gly Ser Thr Glu Val Asp Ser
            20                  25                  30

Val Leu Lys Asn Ile Asp Phe Asp Val Ser Asp Ala Ser Lys Val
        35                  40                  45

Leu Ser Leu Ser Thr Asp Tyr Asn Ala Arg Asn Leu Met Ala Leu Ser
    50                  55                  60

Leu Val Leu Ala Asn Asn Asp Asn Ile Asn Asn Tyr Asn Gln Lys Tyr
65                  70                  75                  80

Ile Gln Lys Val Ile Thr Val Ile Asp Lys Leu Ile Asp Leu Gln Val
                85                  90                  95

Asn Ser Ile Ile Ser Asn Asp Glu Phe Arg Ala Leu Glu Gln Glu Trp
            100                 105                 110

Leu Lys Val Gln Glu Val Cys Gln Glu Asp Tyr Asp Asn Val Glu Val
        115                 120                 125

```
Ser Ile Leu Asp Val Lys Lys Glu Glu Leu Gln Tyr Asp Phe Glu Arg
130                 135                 140

Asn Leu Tyr Asp Ile Ser Ser Asp Phe Phe Lys Lys Val Tyr Val
145                 150                 155                 160

Ser Glu Phe Asp Gln Tyr Gly Gly Glu Pro Tyr Gly Ala Ile Leu Gly
                165                 170                 175

Leu Tyr Asn Phe Glu Asn Thr Thr Asn Asp Ile Ile Trp Leu Thr Gly
                180                 185                 190

Met Gly Met Val Ala Lys Asn Ser His Ala Pro Phe Ile Ala Ser Ile
        195                 200                 205

Asp Lys Ser Phe Phe Gly Val Lys Asp Leu Ser Glu Ile Thr His Ile
        210                 215                 220

Lys Ser Phe Glu Ala Leu Leu Glu His Pro Arg Tyr Lys Glu Trp Asn
225                 230                 235                 240

Asp Phe Arg Asn Leu Asp Val Ala Ala Tyr Ile Gly Leu Thr Val Gly
                245                 250                 255

Asp Phe Met Leu Arg Gln Pro Tyr Asn Pro Glu Asn Asn Pro Val Gln
                260                 265                 270

Tyr Lys Leu Met Glu Gly Phe Asn Glu Phe Val Asp Tyr Asp Lys Asn
        275                 280                 285

Glu Ser Tyr Leu Trp Gly Pro Ala Ser Ile His Leu Val Lys Asn Met
        290                 295                 300

Met Arg Ser Tyr Asp Lys Thr Arg Trp Phe Gln Tyr Ile Arg Gly Val
305                 310                 315                 320

Glu Ser Gly Gly Tyr Val Lys Asn Leu Val Ala Cys Val Tyr Asp Asn
                325                 330                 335

Lys Gly Ile Leu Glu Thr Lys Ser Pro Leu Asn Val Leu Phe Ala Asp
                340                 345                 350

Tyr Met Glu Leu Ser Leu Ala Asn Ile Gly Leu Ile Pro Phe Val Ser
        355                 360                 365

Glu Lys Gly Thr Ser Asn Ala Cys Phe Phe Ser Val Asn Ser Ala Lys
        370                 375                 380

Lys Val Glu Glu Phe Val Asp Gly Phe Asp Ser Ala Asn Ser Arg Leu
385                 390                 395                 400

Ile Ala Asn Leu Ser Tyr Thr Met Cys Ile Ser Arg Ile Ser His Tyr
                405                 410                 415

Ile Lys Cys Val Ile Arg Asp Lys Ile Gly Ser Ile Val Asp Val Glu
        420                 425                 430

Ser Ile Gln Lys Ile Leu Ser Asp Trp Ile Ser Glu Phe Val Thr Thr
        435                 440                 445

Val Tyr Gln Pro Thr Pro Leu Glu Met Ala Arg Tyr Pro Phe Arg Asn
450                 455                 460

Val Ser Ile Glu Val Glu Thr Ile Pro Gly Lys Pro Gly Trp Tyr Ser
465                 470                 475                 480

Cys Lys Ile Asn Val Ile Pro His Ile Gln Phe Glu Gly Met Asn Thr
                485                 490                 495

Thr Met Thr Ile Asp Thr Arg Leu Glu Pro Glu Leu Phe Gly Thr Asn
            500                 505                 510

Asn Asn
```

VACCINES AGAINST TULAREMIA

This application is a U.S. National Stage Application filed under 35 U.S.C. 371 and claims priority to International Application No. PCT/US10/33352, filed May 3, 2010, which application claims priority from U.S. Provisional Application Ser. No. 61/175,436, filed May 4, 2009, which are incorporated herein by reference.

STATEMENT REGARDING FEDERALLY SPONSORED RESEARCH

This invention was made with Government support of Grant No. DAMD17-03-1-0052, awarded by the United States Army. The Government has certain rights in this invention.

TECHNICAL FIELD

The invention relates generally to an antigenic composition useful for immunization against tularemia. The invention is a method for producing a vaccine for preventing tularemia in humans and animals, a new vaccine against tularemia in humans and animals, and a new approach to producing vaccines against tularemia.

BACKGROUND

The Gram-negative bacterium *Francisella tularensis* is the causative agent of the zoonotic disease tularemia. Humans acquire tularemia from contact with infected tissues or materials, insect bites, consumption of contaminated food or water, or inhalation of aerosols. *F. tularensis* consists of 3 subspecies—*tularensis, holarctica* and *mediasiatica*—which differ in their geographic distributions and in their virulence in humans. *F. tularensis* subspecies *tularensis*, found almost exclusively in North America is highly virulent for humans. As few as 10 organisms subcutaneously or 25 organisms by inhalation can lead to a severe infection. *F. tularensis* subspecies *holarctica* (found in North America and in Europe) and subspecies *mediasiatica* (found in Asia) are of lower virulence. Because of its high infectivity and capacity to cause severe morbidity and mortality, *F. tularensis* subspecies *tularensis* is considered a potential agent of bioterrorism.

A vaccine against *F. tularensis* was developed a half-century ago, but it has not been approved for general use. This vaccine, called Live Vaccine Strain, or LVS, is an attenuated form of *Francisella tularensis* subspecies *holarctica*, a much less virulent subspecies of *F. tularensis* than the highly virulent subspecies of concern as a bioterrorist agent, *F. tularensis* subspecies *tularensis*. The LVS vaccine is poorly characterized, unstable in that different colonial morphology types emerge on culture, and somewhat toxic to humans vaccinated with it. Moreover, it may not protect against the high doses of *F. tularensis* subspecies *tularensis* that might be released in an airborne bioterrorism attack.

SUMMARY

The invention provides methods and compositions useful for preventing infection caused by *Francisella tularensis*, the agent of tularemia, and a potential agent of bioterrorism.

The disclosure describes a novel vaccine and vaccine vector comprised of an unmarked attenuated deletional mutant of the LVS vaccine. The deletion comprises a knockout or disruption in a gene called capB or a polynucleotide encoding capB (SEQ ID NO:19). The LVSΔcapB mutant, like the previously evaluated LVSΔwbtDEF mutant, is highly attenuated compared with LVS. Surprisingly, however, the LVSΔcapB mutant induces protective immunity against *F. tularensis* intranasal challenge comparable to LVS.

In addition, the disclosure describes recombinant versions of LVSΔcapB expressing *F. tularensis* immunoprotective proteins. In addition, the disclosure envisions immunization utilizing a homologous or heterologous prime-boost vaccination strategy. The heterologous strategy may include priming with one vector, e.g. LVSΔcapB expressing one or more *F. tularensis* proteins, and boosting with another vector, e.g. *L. monocytogenes* expressing one or more *F. tularensis* proteins. Boosting may also include immunizing with the *F. tularensis* protein or proteins in adjuvant.

The disclosure provides a live vaccine comprising an *F. tularensis* lacking a polynucleotide encoding a functional CapB (LVSΔcapB). In one embodiment, the *F. tularensis* expresses or over-expresses an *F. tularensis* antigen. In a further embodiment, the LVSΔcapB expresses or overexpresses at least one polypeptide selected from the group consisting of AcpA, Bfr, DnaK, FabD, GroEL, IglA, IglB, IglC, VgrG, KatG, Pld, SodB and any combination thereof. In one embodiment, the LVSΔcapB expresses an immunogenic IglC. In another embodiment, the LVSΔcapB expresses an immunogenic IglA. In yet another embodiment, the LVSΔcapB expresses an immunogenic IglA and IglC. In yet another embodiment, the LVSΔcapB expresses an immunogenic IglA, IglC and VgrG.

The disclosure also provides an immunoprotective composition comprising an attenuated *F. tularensis* lacking a polynucleotide encoding a functional CapB and expressing or overexpressing an antigen useful for inducing an immunoprotective response against *Francisella tularensis*, said antigen comprising an extracellular or immunogenic polypeptide of *F. tularensis* or immunogenic fragment thereof linked to transcriptional promoter and termination signals. In one embodiment, the the *F. tularensis* polypeptide or fragment thereof is selected from the group consisting of AcpA, Bfr, DnaK, FabD, GroEL, IglA, IglB, IglC, VgrG, KatG, Pld, Tul4, SodB, and any combination thereof. In one embodiment, the polypeptide or fragment is IglA and/or IglC antigen of *F. tularensis*. In yet another embodiment, the composition further comprising a pharmaceutical diluent.

The disclosure also provides a prime-boost immunization method comprising a first immunoprotective composition comprising a LVSΔcapB and a second immunoprotective composition comprising an attenuated vector expressing AcpA, Bfr, DnaK, FabD, GroEL, IglA, IglB, IglC, VgrG, KatG, Pld, Tul4, SodB polypeptide, immunogenic fragement, and any combination thereof. In one embodiment, the second immunoprotective composition comprises an attenuated vector comprises an adenoviral vector or an attenuated *L. monocytogenes*.

The disclosure also provides a method of inducing protective immunity in a subject comprising administering a composition of the disclosure to the subject, the composition comprising a LVSΔcapB and may further comprise a LVSΔcapB expressing an *F. tularensis* antigen.

The disclosure also provides a method of protecting a susceptible host against an infection of *Francisella tularensis* (*F. tularensis*) comprising administering to said host an amount of the immunoprotective composition of the disclosure sufficient to invoke an immunoprotective response in the host.

The disclosure also provides a recombinant attenuated *F. tularensis* lacking a polynucleotide encoding CapB and comprising a polynucleotide encoding at least one extracellular or immunogenic protein, or fragment thereof, of *F. tularensis* that induces a protective immunity against *F. tularensis*. In one embodiment, the extracellular or immunogenic protein or fragment *F. tularensis* is selected from the group consisting of AcpA, Bfr, DnaK, FabD, GroEL, IglA, IglB, IglC, VgrG, KatG, Pld, Tul4, and SodB and any combination thereof.

The disclosure also provides a method of immunization comprising administering a prime-boost combination to a subject, wherein the prime vaccine comprises an *F. tularensis* lacking a polynuclotide encoding CapB (LVSΔcapB), and wherein the boost vaccine comprises at least one attenuated vector comprising at least one *F. tularensis* antigen selected from the group consisting of AcpA, Bfr, DnaK, FabD, GroEL, IglA, IglB, IglC, VgrG, KatG, Pld, Tul4 SodB, an immunogenic fragment of any of the foregoing and a combination thereof, or an immunogenic polypeptide selected from the group consisting of AcpA, Bfr, DnaK, FabD, GroEL, IglA, IglB, IglC, VgrG, KatG, Pld, Tul4, SodB, an immunogenic fragment of any of the foregoing and any combination thereof. In one embodiment, the the prime vaccine comprises a recombinant attenuated *F. tularensis* lacking a ploynucleotide encoding CapB and comprising a polynucleotide encoding at least one extracellular or immunogenic protein, or fragment thereof, of *F. tularensis* that induces a protective immunity against *F. tularensis*. In another embodiment, the prime vaccine comprises an antigen selected from the group consisting of IglA, IglC and a combination thereof and the boost vaccine comprises an antigen selected from the group consisting of IglA, IglC and a combination thereof. In yet another embodiment, the boost vaccine comprises *L. monocytogenes* or an adenovirus.

BRIEF DESCRIPTION OF THE FIGURES

FIG. 5 shows that immunization with LVSΔcapB induces potent protective immunity against *F. tularensis* i.n. challenge. BALB/c mice (4/group) were immunized i.n. (left panel) or i.d. (right panel) with LVSΔcapB with doses shown at the bottom of the figure. Mice immunized with saline (Sham, 8/group) or immunized with LVS (4/group) served as controls. Four weeks later, the mice were challenged i.n. with 4000 CFU LVS. At 5 days post-challenge, the spleen (upper panels), liver (middle panels) and lung (lower panels) were removed and assayed for bacterial burden. Symbols represent each animal in a group. CFUs were compared by one-way ANOVA (Prism 5) with bonferroni's post test. Dashed line, limit of detection. ***, P<0.001 vs. sham-immunized mice.

Figure 1:
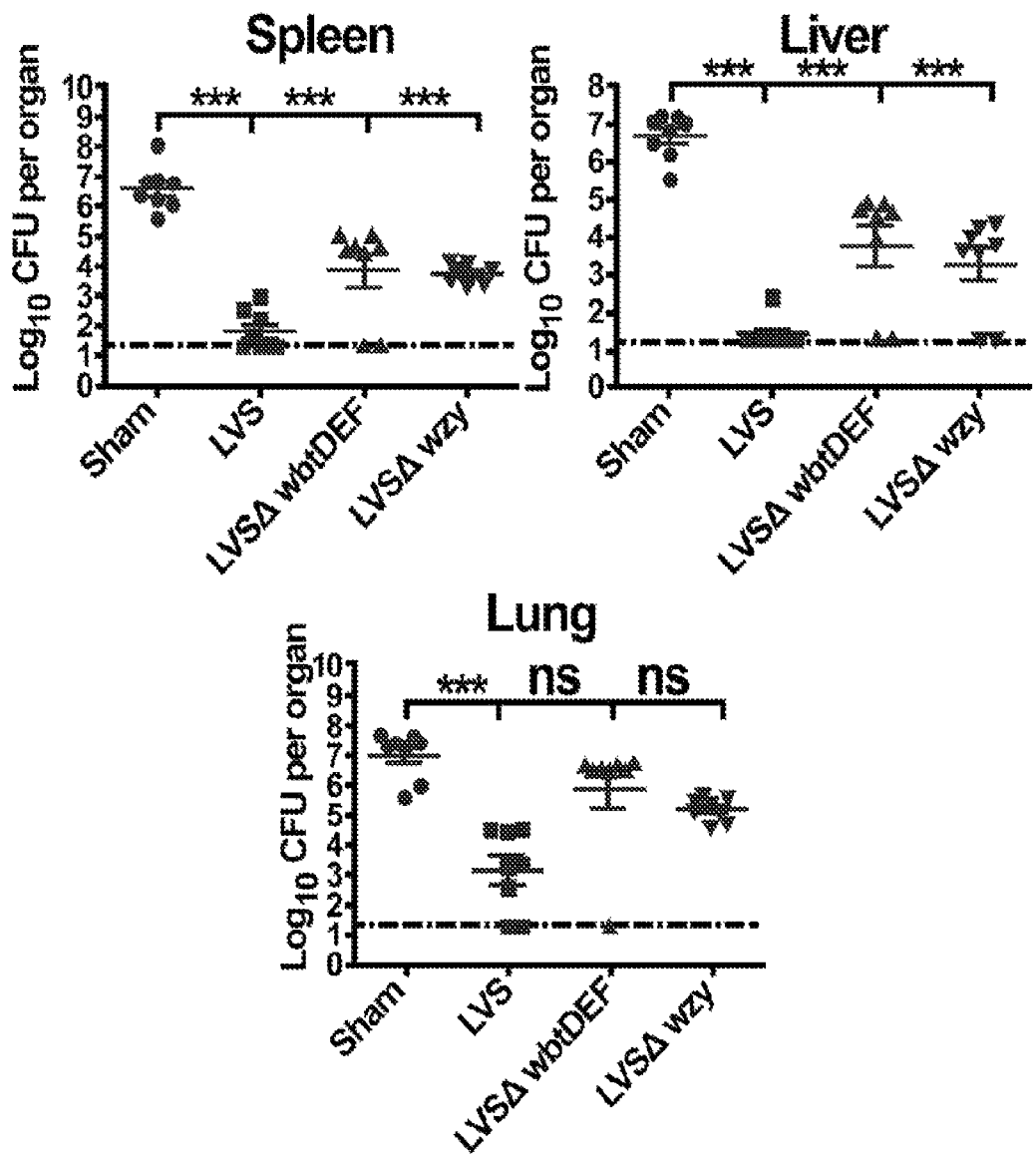
FIG. 1 shows immunization with LVSΔLPS induces modest protective immunity against *F. tularensis* i.n. challenge. Groups of eight BALB/c mice were immunized i.d. twice, 4 weeks apart, with $1 \times 10^8$ CFU LVSΔwbtDEF or LVSΔwzy. Mice immunized with saline (Sham) or immunized with LVS served as controls. Six weeks later, the mice were challenged i.n. with 4000 CFU LVS. At 5 days post-challenge, the spleen, liver and lung were removed and assayed for bacterial burden. Symbols represent each animal in a group. CFUs were compared by one-way ANOVA (Prism 5) with bonferroni's post-test. Dashed line, limit of detection. ***, P<0.001 vs. sham-immunized mice. ns, not significant.

test (Prism 5). ns, not statistically significant. (C) Weight change. Values represent mean±SE from groups of 8 mice.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the peptide" includes reference to one or more peptides, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

*F. tularensis* is a Category A bioterrorism agent that has previously been stock-piled as a germ-warfare agent and may have been used as such in World War II. Especially when spread by the air-borne route, *F. tularensis* can cause a highly fatal pneumonia.

*Francisella tularensis* is a nonmotile, nonsporulating, gram-negative coccobacillus that causes zoonotic disease in small animals such as rodents, rabbits, and beavers. Humans acquire tularemia by handling infected animals, by consumption of contaminated food or water, or by the bite of blood-sucking insects. *F. tularensis* consists of three main subspecies—*tularensis, holarctica*, and *mediasiatica*—which differ in their geographic distributions and in their virulence in humans. *F. tularensis* subspecies *tularensis*, found almost exclusively in North America, is highly virulent for humans. As few as 10 organisms delivered subcutaneously or 25 organisms delivered by inhalation can lead to a severe, potentially lethal, infection in humans. *F. tularensis* subspecies *holarctica* (found in North America and in Europe) and subspecies *mediasiatica* (found in Asia) are of lower virulence. Because of its high infectivity and capacity to cause severe morbidity and mortality, *F. tularensis* subspecies *tularensis* is classified as a category A potential agent of bioterrorism.

Although *F. tularensis* can be grown in the laboratory on enriched culture media, *F. tularensis* bacteria invade and grow productively in macrophages. It is thought that, in natural infections, the bacterium replicates intracellularly within host mononuclear phagocytes. After entry of the organism into the macrophages, *F. tularensis* initially resides in a phagosome. However, the bacterium arrests the maturation of its phagosome, which acquires some markers of early and late endosomes, but not cathepsin D, and it inhibits the acidification of its phagosome. A unique feature of the phagosome is that it is often surrounded by a dense fibrillar coat. With more time after infection, the phagosomal membrane is disrupted and the bacterium replicates freely in the cytoplasm of the macrophage. While these aspects of intracellular life after entry have been reported, the ultrastructure and mechanisms that mediate uptake of this highly infectious bacterium have not previously been reported.

The genomic sequences of certain strains of *F. tularensis* are known as set forth below (the sequences associated with these accession numbers are incorporated herein by reference): NC_010677, *Francisella tularensis* subsp. *mediasiatica* FSC147, complete genome DNA, circular, Length: 1,893,886 nt, Replicon Type: chromosome; NC_009749, *Francisella tularensis* subsp. *holarctica* FTNF002-00, complete genome, DNA, circular, Length: 1,890,909 nt, Replicon Type: chromosome; NC_008601, *Francisella tularensis* subsp. *novicida* U112, complete genome, DNA, circular, Length: 1,910,031 nt, Replicon Type: chromosome; NC_009257, *Francisella tularensis* subsp. *tularensis* WY96-3418, complete genome, DNA, circular, Length: 1,898,476 nt, Replicon Type: chromosome; NC_007880, *Francisella tularensis* subsp. *holarctica* LVS, complete genome, DNA, circular, Length: 1,895,994 nt, Replicon Type: chromosome. NC_006570, *Francisella tularensis* subsp. *tularensis* Schu 4, complete genome, DNA, circular, length: 1,892,819 nt, Replication Type: chromosome. NC_008245, *Francisella tularensis* subsp. *tularensis* FSC 198, complete genome, DNA, circular, length: 1,892,616 nt, Replication Type: chromosome.

The disclosure provides an attenuated recombinant *F. tularensis* useful as a vaccine or for the delivery of antigens for vaccine purposes.

A brief description of the immune system will assist in understanding the disclosure. There are two arms to the immune response: a humoral (antibody) response and a cell-mediated response. Protein antigens derived from pathogens that replicate intracellularly (viruses and some bacteria) are processed within the infected host cell releasing short peptides which are subsequently displayed on the infected cell surface in association with class I major histocompatability (MHC I) molecules. When this associated complex of MHC I and peptide is contacted by antigen-specific CD8+ T-cells the T-cell is activated, acquiring cytotoxic activity. These cytotoxic T-cells (CTLs) can lyse infected host cells, so limiting the replication and spread of the infecting pathogen. Another important arm of the immune response is controlled by CD4+ T-cells. When antigen derived from pathogens is released into the extracellular milieu they may be taken up by specialised antigen-presenting cells (APCs) and displayed upon the surface of these cells in association with MHC II molecules. Recognition of antigen in this complex stimulates CD4+ T-cells to secrete soluble factors (cytokines) which regulate the effector mechanisms of other T-cells. Antibody is produced by B-cells. Binding of antigen to secreted antibody may neutralise the infectivity of a pathogen and binding of antigen to membrane-bound antibody on the surface of B-cells stimulates division of the B-cell so amplifying the B-cell response. In general, good antibody responses are required to control bacterial infections and both antibody and cell-mediated immune responses (CD8+ and CD4+) are required to control infections by viruses.

"CD8+ T cells" represent a class of T lymphocytes characterized by the possession of the CD8 cell surface marker. CD8+ T cells are MHC Class I-restricted "CTLs" or "suppressor T cells."

"CD4+ T cells" represent a class of T lymphocytes characterized by the possession of the CD4 cell surface marker. CD4+ T cells are MHC Class 11-restricted T lymphocytes. There are two types of CD4+ T cells referred to as type 1 or type 2 "helper T cells."

The driving force behind the development of these two types of immune responses is cytokines, a number of identified protein messengers which serve to help the cells of the immune system and steer the eventual immune response to either a Th1 or Th2 response. Thus, high levels of Th1-type cytokines tend to favor the induction of cell mediated immune responses to the given antigen, while high levels of Th2-type cytokines tend to favor the induction of humoral immune responses to the antigen. It is important to remember that the distinction of Th1 and Th2-type immune responses is not absolute. In reality, an individual will support an immune response which is described as being predominantly Th1 or predominantly Th2. Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumour necrosis factor-β (TNF-β).

The disclosure comprises several types of vaccines. One vaccine is LVSΔcapB. Other vaccines comprise LVSΔcapB expressing one or more $F.$ tularensis antigens, e.g., IglC, IglA, IglB, and/or VgrG (PigB) as described below.

A vaccine of the disclosure can be administered intranasally, intradermally or by another route, e.g. subcutaneously, intramuscularly, inhaled, or even orally to a mammalian host. The vaccine can be administered as part of a homologous or heterologous prime-boost strategy.

The vaccine induces a strong cell-mediated immune response to pathogen antigens in the vaccine. Most importantly, the vaccine protects the mammalian hosts against infection with $F.$ tularensis.

In one embodiment, the vaccine is administered to humans or animals by inhalation including intranasally, injection intradermally or by another route, e.g. subcutaneously, intramuscularly, or orally.

As demonstrated herein, the vaccines of the disclosure are safer than prior vaccines. Remarkably, despite their attenuation, their efficacy is comparable and exceeds LVS vaccines.

The disclosure provides a live recombinant $F.$ tularensis (e.g., an attenuated $F.$ tularensis) lacking a polynucleotide encoding a CapB polypeptide (SEQ ID NO:20) or homologs or variants thereof (e.g., having at least 90-99% identity to SEQ ID NO:20), referred to herein as LVSΔcapB. The LVSΔcapB is recombinantly produced by knocking out or disrupting a polynucleotide encoding the CapB polypeptide.

The term "attenuated," when used with respect to a bacterium, means that the bacterium has lost some or all of its ability to proliferate and/or cause disease or other adverse effect when the bacterium infects an organism. For example, an "attenuated" bacterium can be unable to replicate at all, or be limited to one or a few rounds of replication, when present in an organism in which a wild-type or other pathogenic version of the attenuated bacteria can replicate. Alternatively or additionally, an "attenuated" bacterium might have one or more mutations in a gene or genes (e.g., encoding a functional O-antigen) that are involved in pathogenicity of the bacteria. Many genes, loci, or operons are known, mutations in which will result in an attenuated bacterium.

A "polynucleotide" generally refers to any polyribonucleotide (RNA) or polydeoxribonucleotide (DNA), which may be unmodified or modified RNA or DNA. Polynucleotides include, without limitation, single-stranded and double-stranded DNA, DNA that is a mixture of single-stranded and double-stranded regions, single-stranded and double-stranded RNA, and RNA that is a mixture of single-stranded and double-stranded regions. Polynucleotides also include hybrid molecules comprising DNA and RNA that may be single-stranded or, more typically, double-stranded or a mixture of single-stranded and double-stranded regions. In addition, "polynucleotide" refers to triple-stranded regions comprising RNA or DNA or both RNA and DNA. Polynucleotides also include DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. Oligonucleotides are relatively short polynucleotides. Examples of polynucleotides encoding $F.$ tularensis antigens are set forth in SEQ ID NOs: 1, 3, 5, 7, 9, 11, 13, 15, 17, 21, and 23 (or fragments thereof encoding antigenic epitopes).

A "polypeptide" refers to any polypeptide comprising two or more amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than those normally encoded by a codon.

Polypeptides include amino acid sequences modified either by natural processes, such as post-translational processing, or by chemical modification techniques that are well known in the art. Such modifications are well described in the literature and are known in the art. Modifications may occur anywhere in a polypeptide, including the peptide backbone, the amino acid side-chains and the amino or carboxyl termini. Such modifications may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Examples of polypeptides useful in the methods and compositions of the invention comprise the *F. tularensis* polypeptide comprising CapB and antigens set forth in SEQ ID Nos: 2, 4, 6, 8, 10, 12, 14, 16, and 18 and antigenic fragments thereof.

A "vaccine" as used herein refers to a composition of matter comprising an attenuated cell or microorganism that induces an immune response, a molecule that, when administered to a subject, induces an immune response, or a combination of an attenuated or live vector that express an antigen that induces an immune response. Vaccines can comprise polynucleotide molecules, polypeptide molecules, and carbohydrate molecules, as well as derivatives and combinations of each, such as glycoproteins, lipoproteins, carbohydrate-protein conjugates, fusions between two or more polypeptides or polynucleotides, and the like. A vaccine may further comprise a diluent, an adjuvant, a carrier, or combinations thereof, as would be readily understood by those in the art.

A vaccine may be comprised of separate components. As used herein, "separate components" refers to a situation wherein the term vaccine actually comprises two discrete vaccines to be administered separately to a subject. In that sense, a vaccine comprised of separate components may be viewed as a kit or a package comprising separate vaccine components. For example, in the context of the disclosure, a package may comprise a first immunogenic composition comprising an attenuated bacterial vector and a second antigenic composition comprising an attenuated viral vector comprising the same or different *F. tularensis* antigens (e.g., AcpA, Bfr, DnaK, FabD, GroEL, IglA, IglB, IglC, KatG, Pld and SodB).

A vaccine "induces" an immune response when the microorganism, antigen or antigens present in the vaccine cause the vaccinated subject to mount an immune response to that antigen or antigens. The vaccinated subject will generate an immune response, as evidenced by activation of the immune system, which includes the production of vaccine antigen-specific T cells, vaccine antigen-specific B cells, vaccine antigen-specific antibodies, and cytokines. The resulting immune response may be measured by several methods including ELISPOT, ELISA, chromium release assays, intracellular cytokine staining, FACS analysis, and MHC tetramer staining (to identify peptide-specific cells). A skilled artisan may also use these methods to measure a primary immune response or a secondary immune response.

An "antigen" is a substance capable of generating an immune response in a subject exposed to the antigen. Antigens are usually polypeptides and are the focus of the host's immune response. An "epitope" or "antigenic determinant" is that part of an antigen to which T cells and antibodies specifically bind. An antigen may contain multiple epitopes. Antigens of the disclosure comprise *F. tularensis* extracellular polypeptides. In specific aspect, the *F. tularensis* polypeptides comprise AcpA, Bfr, DnaK, FabD, GroEL, IglC, KatG, Pld, SodB, IglA and IglB (SEQ ID NOs: 2, 4, 6, 8, 10, 12, 14, 16, 18, 22 and 24, respectively).

A priming vaccine used in the method of the disclosure comprises an *F. tularensis* antigen (e.g., IglC as the prime vaccine). The priming vaccine may be an antigenic epitope of an *F. tularensis* antigen, the full length antigen, a vector comprising a polynucleotide encoding the antigen (e.g., a LVSΔcapB/$P_{gro}$-IglC) and the like. In one embodiment, the priming vaccine comprises a polynucleotide encoding an antigen under control of a foreign promoter within a bacterium or virus. The polynucleotide of the priming vaccine is present in a suitable delivery vector such as a plasmid or other vector such as a bacterial or viral vector. The polynucleotide may be under the control of a suitable promoter such as a promoter derived from the HCMV IE gene. In specific aspects, the rLVSΔcapB vaccines comprise polynucleotides encoding *F. tularensis* antigens IglC, IglA, VgrG, and/or IglB under the control of the *F. tularensis* LVS groE operon promoter. The recombinant *Listeria monocytogenes* vaccines comprise polynucleotides encoding *F. tularensis* antigens IglC, IglA, VgrG, and/or IglB under the control of the *L. monocytogenes* hly or actA promoter. The priming vaccine is administered in an amount effective for priming an immune response to the *F. tularensis* antigen. As used herein, "priming" of an immune response occurs when an antigen is presented to T cells or B cells. As a result, primed cells can respond to the same antigen again as memory cells in a second, subsequent immune response. Thus, priming generates both the primary immune response and establishes immunological memory. One skilled in this art appreciates that a primary immune response represents the adaptive immune response upon initial exposure to an antigen in a particular context such as in the pathogen or in a vaccine. However, it will also be appreciated that the disclosure is not limited to use of the priming vaccine in the context of immunologically naive individuals. Rather, priming may also occur in individuals who have been exposed to the antigen but who have not received the priming vaccine. In a specific embodiment, the priming vaccine comprises an attenuated *F. tularensis* vector.

The priming immunogenic (vaccine) composition may be administered once before administration of the boosting immunogenic (vaccine) composition. In another embodiment, the priming vaccine may be administered several times.

The boosting vaccine used in the method of the disclosure may comprise at least one *F. tularensis* antigen polypeptide. The boosting vaccine may comprise the same or a different antigen. The boosting vaccine may comprise the same or a different vector. In one embodiment, the boosting vaccine comprises an additional *F. tularensis* polypeptide antigen to enhance the immunogenicity of of the subject to *F. tularensis*. For example in one embodiment, the boosting vaccine comprises an *F. tularensis* antigen expressed in a viral vector. The *F. tularensis* antigen can be selected from the group consisting of AcpA, Bfr, DnaK, FabD, GroEL, IglC, KatG, Pld, SodB, IglA, IglB, and VgrG. In a specific embodiment, the boosting vaccine comprises IglC and/or KatG expressed in an adenovirus vector. In a specific embodiment, a vaccine combination of the disclosure comprises a prime vaccine of LVS-ΔcapB *F. tularensis* expressing an antigen from *F. tularensis* and a boosting vaccine of adenovirus expressing the same or a different *F. tularensis* antigen. In another specific embodiment, a vaccine combination of the disclosure comprises a prime vaccine of LVSΔcapB *F. tularensis* and a boosting vaccine of attenuated *L. monocytogenes* expressing an *F. tularensis* antigen. In another specific embodiment, a vaccine combination of the disclosure comprises a prime vaccine of LVSΔcapB *F. tularensis* expressing an antigen from *F. tularensis* and a boosting vaccine of attenuated *L. monocytogenes* expressing the same or a different *F. tularensis* antigen.

The boosting vaccine is administered in an amount effective for "boosting" a primed immune response to the *F. tularensis* antigen. As used herein, "boosting" an immune response means to induce a secondary immune response in a subject that has been primed (i.e., already exposed) by an initial exposure to an antigen. A secondary immune response is characterized by the activation and expansion of specific memory T cells and B cells. Thus, boosting a specific immune response augments the primed immune response by inducing immune cells to proliferate and differentiate upon subsequent exposure to that antigen. The boosting vaccine may achieve one or more of the following effects: induces CD4+ T cells, induces anti-*F. tularensis* antibodies, boosts the activity of the CD8+ T cells primed by the priming vaccine, and induces additional CD8+ T cells not originally identified in the initially primed immune response. The boosting vaccine may also induce CD4+ T cells and induce anti-*F. tularensis* antibodies.

Certain vaccine adjuvants are particularly suited to the stimulation of either Th1 or Th2-type cytokine responses. Traditionally, the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen specific antibody responses. Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype.

As noted herein, the vaccines of the disclosure comprising an attenuated *F. tularensis* (e.g., a LVSΔcapB) are safer, more stable, and more efficacious than the previously developed but never approved LVS vaccine.

Attenuated vaccines can be administered directly to the mammal. The immunogenic compositions and vaccines obtained using the methods of the disclosure can be formulated as pharmaceutical compositions for administration in any suitable manner. One route of administration is oral. Other routes of administration include rectal, intrathecal, buccal (e.g., sublingual) inhalation, intranasal, and transdermal and the like (see e.g. U.S. Pat. No. 6,126,938). Although more than one route can be used to administer a particular composition, a particular route can often provide a more immediate and more effective reaction than another route.

The disclosure provides an immunogenic composition and vaccine that utilize a live attenuated recombinant *F. tularensis* vector to deliver *F. tularensis* immunogenic antigens. The rationale for using live attenuated *F. tularensis* subspecies holarctica (LVS or LVSΔcapB) as a vector was that this bacterium would deliver antigens in host cells in a way that mimicked a wild-type *F. tularensis*. Like *F. tularensis* subspecies *tularensis*, LVS is an intracellular bacterium that resides in host mononuclear phagocytes. *F. tularensis* LVS escapes the phagosome and resides in the cytoplasm of the host cell. Thus, *F. tularensis* LVS releases potentially immunoprotective antigens into the host cell cytoplasm, after which they are processed and presented to the immune system. Such antigens are presented to the immune system via MHC class I molecules, resulting in the priming of CD8 T-cells. When *F. tularensis* is utilized as a vector for the release of *F. tularensis* immunogenic antigens, the antigens are processed and presented in a way that mimics their processing and presentation by natural infection and thereby stimulate a highly potent immunoprotective response.

In addition, the disclosure envisions immunization utilizing a homologous or heterologous prime-boost vaccination strategy. The heterologous strategy may include priming with one vector, e.g., an attenutated *F. tularensis* expressing one or more proteins, and boosting with another vector, e.g., adenovirus or attenuated *L. monocytogenes* expressing the same protein or proteins, or vice versa. Boosting may also include immunizing with an *F. tularensis* protein or proteins or fragments thereof in an adjuvant. The specific examples provided herein demonstrate the delivery of the antigens to an animal host utilizing various vaccination strategies and the resulting immunoprotection against *F. tularensis* challenge.

The disclosure comprises several types of vaccines. One group of vaccines consists of attenuated *F. tularensis* expressing one or more *F. tularensis* antigens. Each vaccine is administered intradermally or by another route, e.g. subcutaneously, intramuscularly, intranasally, inhaled, or even orally to a mammalian host. The vaccine can be administered as part of a homologous or heterologous prime-boost strategy. The vaccine induces a strong cell-mediated immune response to pathogen antigens in the vaccine. Most importantly, the vaccine protects the mammalian hosts against infection with *F. tularensis*.

The antigens can be delivered via an attenuated vector comprising a polynucleotide encoding an antigenic polypeptide of *F. tularensis* that results in presentation of the encoded polypeptide via MHC class I or MHC class II. Examples of attenuated vectors useful in the disclosure for combination prime-boost therapies include *L. monocytogenes*, *F. tularensis* lacking a functional O-Antigen, *F. tularensis* Live Vaccine Strain (LVS), or another attenuated bacterial vector such as *Mycobacterium bovis* BCG, *Shigella flexneri* and *Escherichia coli*. Examples of attenuated bacteria used as live vaccines include *S. typhi* carrying a mutation in its galE or htrA gene, and *V. cholerae* carrying mutations in its ctxA gene. For example, the recombinant *Listeria monocytogenes* strains expressing *F. tularensis* IglC and KatG (rLM/IglC or rLM/KatG) were demonstrated to protect against aerosol challenge with the highly virulent Type A *F. tularensis* subspecies *tularensis* SchuS4 Strain.

Microorganisms which are used to express an *F. tularensis* antigen for use in immunoprotective compositions include, without limitation, *Campylobacter* sp., *Yersinia* sp., *Helicobacter* sp., *Gastrospirillum* sp., *Bacteroides* sp., *Klebsiella* sp., *Lactobacillis* sp., *Streptococcus gordonii*, *Enterobacter* sp., *Salmonella* sp., *Shigella* sp., *Aeromonas* sp., *Vibrio* sp., *Clostridium* sp., *Enterococcus* sp. and *Escherichia coli* (see e.g. U.S. Pat. Nos. 5,858,352, and 6,051,416, and Levine et al., in "New Generation Vaccines Second Edition" ed. Levine et al., Marcel Dekker, Inc. pp 351-361 (1997), Levine et al., in "New Generation Vaccines Second Edition" ed. Levine et al., Marcel Dekker, Inc. pp 437-446 (1997), Butterton et al., in "New Generation Vaccines Second Edition" ed. Levine et al., Marcel Dekker, Inc. pp 379-385 (1997) and Fennelly et al., in "New Generation Vaccines Second Edition" ed. Levine et al., Marcel Dekker, Inc. pp 363-377 (1997)). For example, *Campylobacter jejuni*, *Campylobacter coli*, *Listeria monocytogenes*, *Yersinia enterocolitica*, *Yersinia pestis*, *Yersinia pseudotuberculosis*, *Escherichia coli*, *Shigella flexneri*, *Shigella sonnei*, *Shigella dysenteriae*, *Shigella boydii*, *Helicobacter pylori*, *Helicobacter felis*, *Gastrospirillum hominus*, *Vibrio cholerae*, *Vibrio parahaemolyticus*, *Vibrio vulnificus*, *Bacteroides fragilis*, *Clostridium difficile*, *Salmonella typhimurium*, *Salmonella typhi*, *Salmonella gallinarum*, *Salmonella pullorum*, *Salmonella choleraesuis*, *Salmonella enteritidis*, *Klebsiella pneumoniae*, *Enterobacter cloacae*, and *Enterococcus faecalis*. *Escherichia coli* include but are not limited to entero-toxic, entero-hemorrhagic, entero-invasive, entero-pathogenic or other strains can be used in the disclosure.

The disclosure also provides an immunogenic composition and vaccine that uses an antigen delivery method that deliveries *F. tularensis* immunogenic antigens in a manner that is similar to delivery in a natural infection. *F. tularensis* antigens are delivered in one or more vectors capable of inducing presentation via Major Histocompatability Complex (MHC) I.

In one aspect, the disclosure provides an immunogenic composition and vaccine that utilize a live attenuated recombinant *Listeria monocytogenes* vector to deliver *F. tularensis* immunogenic antigens. A rationale for using live attenuated *L. monocytogenes* as a vector is the similarity in the infective process between *L. monocytogenes* and *F. tularensis* (other attenuated bacterial vectors having a similar infective process can be used). Like *F. tularensis*, *L. monocytogenes* is an intracellular bacterium that resides in host mononuclear phagocytes. Importantly, *L. monocytogenes* escapes the phagosome in which it initially resides and subsequently inhabits the cytoplasm of the host cell. *F. tularensis* also escapes the phagosome and resides in the cytoplasm of the host cell. Thus, *F. tularensis* releases potentially immunoprotective antigens into the host cell cytoplasm, after which they are processed and presented to the immune system. Such antigens are presented to the immune system via MHC class I molecules, resulting in the priming of CD8 T-cells. When *L. monocytogenes* is utilized as a vector for the release of *F. tularensis* immunogenic antigens, the antigens are processed and presented in a way that mimics their processing and presentation by *F. tularensis* and thereby stimulate an immunoprotective response (see, e.g., PCT/US07/22418, filed Oct. 22, 2007, incorporated herein by reference for all purposes). In another aspect, an attenuated *F. tularensis* lacking a wild-type O-antigen is used. In another aspect, the attenuated *F. tularensis* LVS strain is used.

Alternatively, or in addition to, a non-bacterial attenuated vector such as a replication-deficient viral vectors may be used in the methods and compositions of the disclosure. Such viral vectors useful in the methods and compositions of the invention include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, and herpes viruses. Naked DNA vectors can also be used in addition to antigenic proteins alone or in combination with an adjuvant.

Examples of suitable viral vectors include herpes simplex viral vectors, vaccinia or alpha-virus vectors and retroviruses, including lentiviruses, adenoviruses and adeno-associated viruses. In one embodiment, these vectors are replication defective virus vectors. Gene transfer techniques using these viruses are known to those skilled in the art. Retrovirus vectors, for example, may be used to stably integrate the polynucleotide of the invention into the host genome, although such recombination may not be advisable. Replication-defective adenovirus vectors by contrast remain episomal and therefore allow transient expression.

In a specific embodiment, the adenovirus used as a live vector is a replication defective human or simian adenovirus. Typically these viruses contain an E1 deletion and may be grown on cell lines that are transformed with an E1 gene. Suitable Simian adenoviruses are, for example, viruses isolated from Chimpanzee. Examples of viruses suitable for use in the present invention include C68 (also known as Pan 9) (U.S. Pat. No. 6,083,716, incorporated herein by reference) and Pan 5, 6 and Pan 7 (WO 03/046124 incorporated herein by reference). Thus, these vectors can be manipulated to insert a heterologous polynucleotide coding for an antigen such that the product is expressed. The use formulation and manufacture of such recombinat adenoviral vectors is set forth in detail in WO 03/046142, which is incorporated by reference.

The disclosure provides an immunogenic composition and vaccine that uses an antigen delivery method that deliveries *F. tularensis* immunogenic antigens in a manner that is similar to delivery in a natural infection. *F. tularensis* antigens are delivered in one or more vectors capable of inducing presentation via Major Histocampatability Complex (MHC) I.

Exemplary prime-boost therapies are set forth in Table 1 (rLM=recombinant *L. monocytogenes*; rAdv=recombinant adenovirus):

TABLE 1

| Prime | Boost |
|---|---|
| LVSΔcapB | rLM/IglC and/or rLM/KatG and/or rLM/Tul4 and/or rLM/AcpA and/or rLM/Bfr and/or rLM/GroEL and/or rLM/Pld and/or rLM/DnaK and/or rLM/IglA and or rLM/IglB |
| LVSΔcapB | rAdv/IglC and/or rAdv/KatG or rAdv/IglC-KatG or rAdv/KatG-IglC |
| LVSΔcapB/IglC | rLM/IglC |
| LVSΔcapB/IglA | rLM/IglA |
| LVSΔcapB/IglB | rLM/IglB |
| LVSΔcapB/AcpA | rLM/AcpA |
| LVSΔcapB/Bfr | rLM/Bfr |
| LVSΔcapB/DnaK | rLM/DnaK |
| LVSΔcapB/GroEL | rLM/GroEL |
| LVSΔcapB/IglC | rAdv/IglC |
| LVSΔcapB/IglC and/or LVSΔcapB/IglB and or LVSΔcapB/KatG and/or LVSΔcapB/Tul4 and/or LVSΔcapB/AcpA and/or LVSΔcapB/Bfr and/or LVSΔcapB/GroEL and/or LVSΔcapB/Pld and/or LVSΔcapB/DnaK | The purified protein(s) expressed by the prime vaccine in a suitable carrier with a suitable adjuvant |
| LVSΔcapB/IglC | IglC in a suitable carrier with a suitable adjuvant |
| LVSΔcapB/IglA | IglA in a suitable carrier with a suitable adjuvant |
| LVSΔcapB/IglB | IglB in a suitable carrier with a suitable adjuvant |
| LVSΔcapB/AcpA and/or LVSΔcapB/Bfr and/or LVSΔcapB/DnaK and/or LVSΔcapB/GroEL | AcpA and/or Bfr and/or DnaK and/or GroEL a suitable carrier with a suitable adjuvant |

The immunoprotective compositions to be administered are provided in a pharmaceutically acceptable solution such as an aqueous solution, often a saline or buffered solution, or they can be provided in powder form. There is a wide variety of suitable formulations of pharmaceutical compositions of the invention. See, e.g., Lieberman, Pharmaceutical Dosage Forms, Marcel Dekker, Vols. 1-3 (1998); Remington's Pharmaceutical Science, 17th ed., Mack Publishing Company, Easton, Pa. (1985) and similar publications. The compositions may also include an adjuvant. Examples of known suitable adjuvants include alum, aluminum phosphate, aluminum hydroxide, and MF59 (4.3% w/v squalene, 0.5% w/v Tween 80, 0.5% w/v Span 85)—these are the only ones currently licensed for use in humans. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, or Bacille Calmette-Guerin (BCG). The effectiveness of an adjuvant may be determined by measuring the amount of antibodies directed against the immunogenic antigen.

The number of LVSΔcapB microorganisms (with or without an expressed antigenic peptide or polypeptide) and the concentration of immunogenic antigens of the disclosure in the pharmaceutical formulations can vary widely, e.g., from less than about 0.1%, usually at or at least about 2% to as much as 20% to 50% or more by weight, and will be selected primarily by fluid volumes, viscosities, and the like, in accordance with the particular mode of administration selected.

Formulations suitable for oral administration can comprise (a) liquid solutions, such as an effective amount of the recombinant bacteria suspended in diluents, such as buffered water, saline or PEG 400; (b) capsules, sachets or tablets, each containing a predetermined amount of the active ingredient, as lyophilized powder, liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the attenuated vaccines, when administered orally, must be protected from digestion. This is typically accomplished either by complexing the vaccines with a composition to render it resistant to acidic and enzymatic hydrolysis or by packaging the vaccines in an appropriately resistant carrier such as a liposome or enteric coated capsules. Means of protecting the attenuated bacteria from digestion are well known in the art. The pharmaceutical compositions can be encapsulated, e.g., in liposomes, or in a formulation that provides for slow release of the active ingredient.

The attenuated vaccines, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

The dose administered to a subject, in the context of the invention should be sufficient to effect a beneficial therapeutic and/or prophylactic response in the subject over time. The dose will be determined by the efficacy of the particular attenuated vaccine employed and the condition of the subject, as well as the body weight or vascular surface area of the subject to be treated. The size of the dose also will be determined by the existence, nature, and extent of any adverse side-effects that accompany the administration of a particular vaccine in a particular subject.

In determining the effective amount of the vaccine to be administered in the treatment or prophylaxis of an infection or other condition, the physician evaluates vaccine toxicities, progression of the disease, and the production of anti-vaccine vector antibodies, if any.

The compositions are administered to an animal that is at risk from acquiring an infection caused by $F.$ $tularensis$ or to prevent or at least partially arrest the development of the infection and its complications. An amount adequate to accomplish this is defined as a "therapeutically effective dose." Amounts effective for therapeutic use will depend on, e.g., the antigen composition, the manner of administration, the weight and general state of health of the subject, and the judgment of the prescribing physician. Single or multiple doses of the antigen compositions may be administered depending on the dosage and frequency required and tolerated by the subject, and route of administration. In addition, a booster may be administered in the same of different formulation. For example, the method contemplates administration of a first composition comprising an $F.$ $tularensis$ antigen in an attenuated bacterial vector and a second composition comprising an $F.$ $tularensis$ antigen in an attenuated non-bacterial vector. The second composition may be administered simultaneously or subsequent to administration of the first immunogenic composition.

In particular embodiments, a therapeutically effective dose of the immunoprotective composition is administered to a subject. Amounts of live attenutated bacteria or non-bacteria expressing the $F.$ $tularensis$ or other antigens present in the initial immunization generally range from about $1 \times 10^2$ to $1 \times 10^{11}$ organisms per subject, and more commonly from about $1 \times 10^3$ to $1 \times 10^9$ organisms per subject.

The existence of an immune response to the first dose of the immunoprotective composition may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) prior to administering a subsequent dose. The existence of an immune response to the first dose may also be assumed by waiting for a period of time after the first immunization that, based on previous experience, is a sufficient time for an immune response and/or priming to have taken place. Boosting dosages of an immunoprotective composition can be administered as needed.

The immunoprotective compositions are typically administered to an individual that is immunologically naive with respect to $F.$ $tularensis$. Usually, 2-4 doses of an immunological composition of the invention may be sufficient, however additional doses may be required to achieve a high level of immunity. Additional booster doses may be given every 1-5 years, as necessary, to maintain a high level of immunity.

In general, administration to any individual should begin prior to the first sign of disease, or possibly at the first sign of possible or actual exposure to $F.$ $tularensis$.

The toxicity and therapeutic efficacy of the attenuated vaccines provided by the invention are determined using standard pharmaceutical procedures in cell cultures or experimental animals. One can determine the $ED_{50}$ (the dose therapeutically effective in 50% of the population) using procedures presented herein and those otherwise known to those of skill in the art.

The attenuated vaccines of the invention can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, enteric disorder, or for preventing or treating other diseases or conditions that are mediated by, or potentially susceptible to, a mammalian immune response.

The phrase "pharmaceutically acceptable" refers to molecular entities and compositions that are physiologically tolerable and do not typically produce an allergic or similar undesirable reaction, such as gastric upset, dizziness, fever and the like, when administrated to a human. Preferably, as used herein, the term "pharmaceutically acceptable" means fulfilling the guidelines and approval criteria of a European Community country's Drug Registration Agency concerning products to be used as a drug, or means that the pharmaceutically acceptable compound, composition, method or use, is listed in the European Community country's Pharmacopoeia or other generally recognised pharmacopoeia for use in animals, and more particularly in humans.

The term "pharmaceutical carrier" refers to a diluent, adjuvant, excipient, or vehicle with which the compound is administered. Such pharmaceutical carriers include but are not limited to sterile liquids, such as water and oils, including those of petroleum, oil of animal-, vegetable-, or synthetic origin, such as whale oil, sesame oil, soybean oil, mineral oil and the like. Water or aqueous solutions, saline solutions, and aqueous dextrose and glycerol solutions are preferably employed as carriers, particularly for injectable solutions, droplet-dispensed solutions and aerosols.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

The primary purpose of an adjuvant is to enhance the immune response to a particular antigen of interest. In the context of antibody production for research purposes, adjuvants stimulate the rapid and sustained production of high titers of antibodies with high avidity. This permits ready recovery of antibody for further research in vitro. Adjuvants have the capability of influencing titer, response duration, isotype, avidity and some properties of cell-mediated immunity.

Adjuvants may act through three basic mechanisms. The first is to enhance long term release of the antigen by functioning as a depot. Long term exposure to the antigen should increase the length of time the immune system is presented with the antigen for processing as well as the duration of the antibody response. The second is the interaction the adjuvant has with immune cells. Adjuvants may act as non-specific mediators of immune cell function by stimulating or modulating immune cells. Adjuvants may also enhance macrophage phagocytosis after binding the antigen as a particulate (a carrier/vehicle function).

Selection of an adjuvant is based upon antigen characteristics (size, net charge and the presence or absence of polar groups). Adjuvant choice is also dependent upon selection of the species to be immunized. Adjuvant selection remains largely empirical. Antigens that are easily purified or available in large quantities may be good choices for starting with the least inflammatory adjuvants for immunization. Should antibody response not be suitable, a gradual increase in the inflammatory level of the adjuvant would then be warranted. Antigens which are difficult to come by (e.g., very small quantities are available) may be better choices for complexing with the more inflammatory adjuvants such as CFA. In addition, small molecular weight compounds and others known to be weakly immunogenetic, may need to be complexed with CFA to obtain good antibody titers. Exemplary adjuvants include:

Complete Freund's Adjuvant (CFA) is a mineral oil adjuvant that uses a water-in-oil emulsion which is primarily oil. It generally contains paraffin oil, killed mycobacteria and mannide monoosleate. The paraffin oil is generally not metabolized; it is either expressed through the skin (via a granuloma or abscess) or phagocytized by macrophages.

Incomplete Freund's Adjuvant (IFA) is a mineral oil adjuvant with a composition similar to CFA but lacking killed mycobacteria.

Montanide ISA (incomplete seppic adjuvant) is mineral oil adjuvant that uses mannide oleate as the major surfactant component.

Ribi Adjuvant System (RAS) is an oil-in-water emulsion that contains detoxified endotoxin and mycobacterial cell wall components in 2% squalene.

TiterMax is a water-in-oil emulsion that combines a synthetic adjuvant and microparticulate silica with the metabolizable oil squalene. The copolymer is the immunomodulator component of the adjuvant. Antigen is bound to the copolymer and presented to the immune cells in a highly concentrated form.

Syntex Adjuvant Formulation (SAF) is a preformed oil-in-water emulsion that uses a block copolymer for a surfactant. A muramyl dipeptide derivative is the immunostimulatory component. The components are subsequently included in in squalene, a metabolizable oil.

Aluminum Salt Adjuvants are most frequently used as adjuvants for vaccine antigen delivery and are generally weaker adjuvants than emulsion adjuvants.

Nitrocellulose-adsorbed antigen provides the slow degradation of nitrocellulose paper and prolonged release of antigen.

Encapsulated or entrapped antigens permit prolonged release of antigen over time and may also include immunostimulators in preparation for prolonged release.

Immune-stimulating complexes (ISCOMs) are antigen modified saponin/cholesterol micelles. They generally form stable structures that rapidly migrate to draining lymph nodes. Both cell-mediated and humoral immune responses are achieved. Quil A and QS-21 are examples of ISCOMS.

GerbuR is an aqueous phase adjuvant and uses immunostimulators in combination with zinc proline.

The following examples are provided to further illustrate the invention and are not intended to limit the invention. Those of skill in the art will recognize that specific materials used in the methods and compositions may be substituted with equivalent materials.

EXAMPLES

Example 1

Cell lines, bacteria, and mice. Human macrophage-like THP-1 cells (ATCC TIB-202) were cultured in RPMI 1640 containing penicillin (100 µg/ml) and streptomycin (100 U/ml) and supplemented with 10% FBS. *F. tularensis* LVS and SchuS4 were obtained from the Centers for Disease Control and Prevention (At saged once on monolayers of THP-1 cells, followed by amplification on chocolate II agar (BD BBL, Sparks, Md.) for 3 days. The bacteria were then scraped from colonies on plates, suspended in sterile saline in the presence of 20% glycerol, and stored at −80° C. Before each use in animals, one vial of LVS or SchuS4 was thawed immediately at 37° C., diluted in sterile saline and kept on ice until use.

Six to eight week old specific-pathogen-free female BALB/c mice were purchased from Charles River Laboratory (Wilmington, Mass.).

Intranasal Challenge.

Two LPS mutants, LVSΔwbtDEF and LVSΔwzy, were constructed as vaccine vectors. These vectors were highly attenuated in mice. They protected mice against challenge with intranasal LVS; however, the level of protection was orders of magnitude less than that of LVS, as assessed by assaying the burden of Ft LVS in the lung, spleen, and liver after challenge (FIG. 1). Thus, another deletional mutant was designed. A putative capsule-deficient mutant of LVS was used.

Construction of a Live Attenuated Recombinant LVS Putatively Deficient in Capsule Production (LVSΔcapB).

The LVSΔcapB mutant was obtained by allelic exchange. Briefly, 1-kb upstream and downstream genomic DNA fragments flanking the capB gene of LVS were amplified and ligated via the EcoRI site to form an in-frame capB gene deletion cassette. The deletion cassette was cloned into the suicide plasmid pMP590, bearing a kanamycin resistance gene and a sacB gene and delivered into LVS by electroporation. LVS transformants were subjected to sequential selection on chocolate agar containing kanamycin and 5% sucrose. The resulting LVSΔcapB mutant does not carry any antibiotic-resistance gene. The capB deletion was confirmed by chromosomal sequencing.

Figure 5:
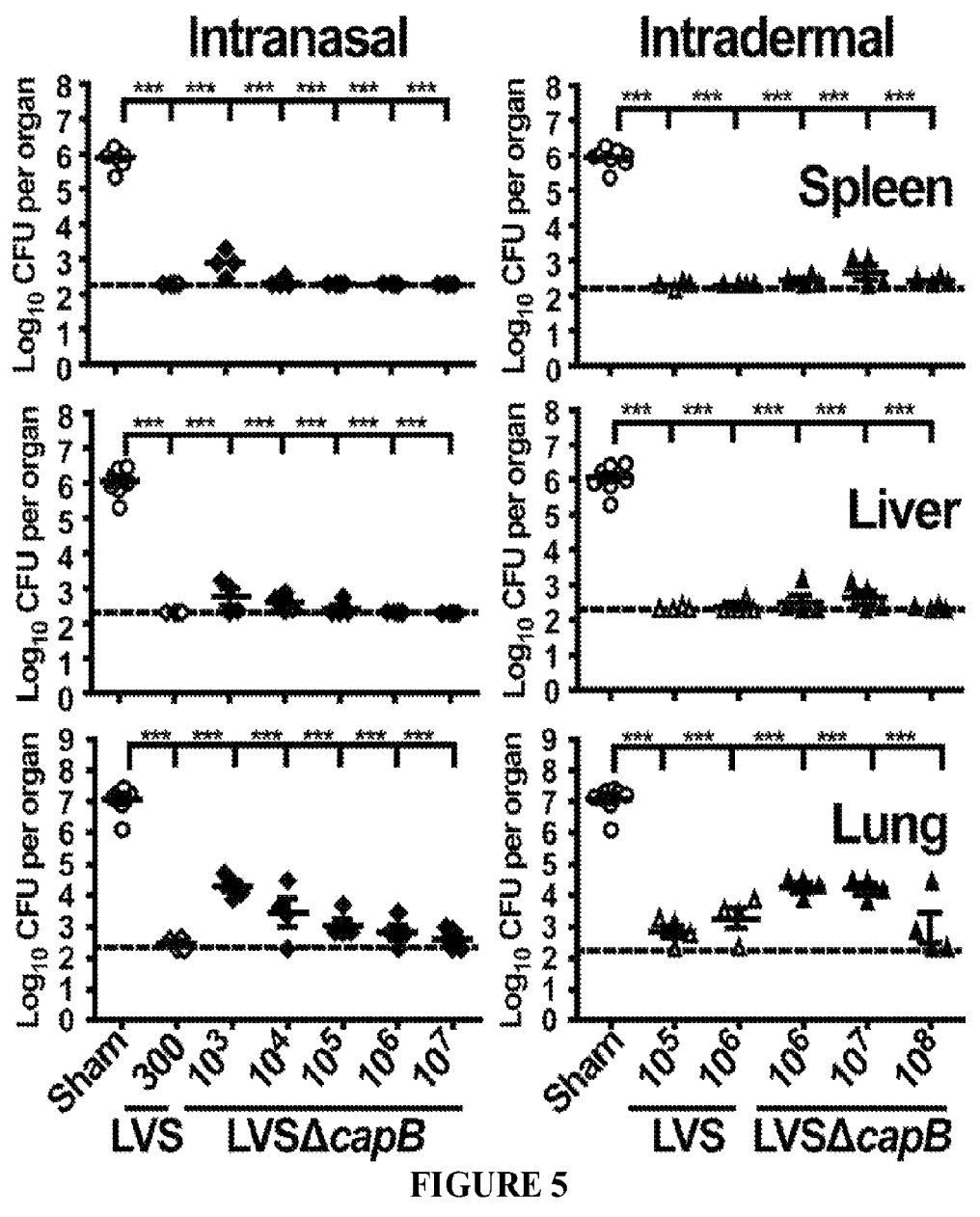

Surprisingly, in view of its marked attenuation, LVSΔcapB induces protective immunity comparable to LVS against lethal i.n. challenge with F. tularensis. To examine the capacity of LVSΔcapB to induce protective immunity against lethal challenge with F. tularensis, mice were immunized with well-tolerated doses of LVSΔcapB i.n. or i.d., and 4 weeks later challenged with 4000 CFU of LVS i.n., a route chosen to mimic respiratory exposure. Sham-immunized mice and mice immunized with moderately well-tolerated doses of LVS (150 CFU i.n. and $1 \times 10^5$ or $1 \times 10^6$ CFU i.d.) served as controls. Five days after challenge, the peak time of bacterial growth in the host, mice were euthanized; the spleen, liver and lung removed and homogenized in sterile saline; the homogenate serially diluted and plated on CHA-HB plates; the plates incubated at 37° C. for 3 days; and CFU enumerated. As shown in FIG. 5, in mice immunized with LVSΔcapB i.n. or i.d., the bacterial burden in the spleen and liver was nearly 4 logs lower and the bacterial burden in the lung was 3-4 logs lower than in sham-vaccinated animals and comparable to the bacterial burden in mice immunized with LVS. This indicated that both local replication in the lung and systemic dissemination of F. tularensis was strongly inhibited by LVSΔcapB immunization.

This result was in marked contrast to the results obtained with the LVSΔwbtDEF mutant (FIG. 1). In animals immunized with LVS or the LVSΔwbtDEF mutant and then challenged with intranasal LVS, the bacterial burden in the lungs, liver, and spleen was markedly reduced in LVS-immunized animals, but not in LVSΔwbtDEF immunized animals (FIG. 1). Whereas LVS-immunized animals showed a reduction in CFU in the lung, liver, and spleen of 3-5 logs compared with sham-immunized animals, LVSΔwbtDEF—immunized animals showed a reduction of only ~1 log in the lung and 2-3 logs in the spleen and liver (FIG. 1). In marked contrast, the reduction in organ bacterial burden in animals immunized with LVSΔcapB was comparable to that in animals immunized with LVS (FIG. 5).

Construction of Recombinant LVSΔcapB Expressing F. tularensis Proteins.

Using LVSΔcapB as a parental strain, the following LVSΔcapB mutants over-expressing the virulent F. tularensis antigens including IglC were generated. LVSΔcapB/Pgro-IglC: To construct plasmids that can replicate in both E. coli and F. tularensis strains, the pFNLTP6/gro-gfp plasmid was used as a delivery vector, which contains a kanamycin resistant gene and is engineered to grow in F. tularensis LVS, F. novicida 112, and E. coli. The coding sequence for F. tularensis SchuS4 IglC was amplified by PCR from the genomic DNA of an F. tularensis subspecies tularensis RCI (recent clinical isolate) and cloned into pZErO. The inserted sequence was confirmed by nucleotide sequencing before it was subcloned into the NdeI-BamHI sites of the pFNLTP6/gro-gfp vector. The resultant plasmid with the insertion of an expression cassette for virulent F. tularensis IglC, pFNLTP6/gro-iglC, was then electroporated into the LVSΔcapB mutant. The bacteria mixture was selected on chocolate agar containing kanamycin (10 μg/ml). The parental capB-deficient LVS mutant is sensitive to kanamycin and therefore cannot grow in the presence of kanamycin. Under the selective pressure of kanamycin, only LVS mutants carrying the transfer vector pFNLTP6/gro-IglC were able to grow on the chocolate agar containing kanamycin (10 μg/ml). After 3 days incubation, the colonies were screened by PCR amplification using two pairs of primers. The first pair was designed to anneal to the 3'end of the groE promoter and the 5'end of IglC coding sequence, which would amplify a PCR product of approximately 670 bp from the LVS mutant carrying the transfer vector. As expected, a 670-bp PCR product was amplified from the selected LVS mutants, but was missing from the parental LVS strain. The second pair of primers was designed to anneal specifically to the 5' and 3' ends of the groE promoter, which would generate a 421-bp PCR product from the parental transfer vector pFNLTP6/gro-gfp and 1035 bp PCR product from the transfer vector with the IglC expression cassette. As expected, the selected LVS strains generated a PCR product of 1035 bp. These results indicated that the selected capB deficient LVS strain contained the transfer vector pFNLTP6/Pgro-IglC. The selected strain was named Ft LVSΔcapB/Pgro-IglC. The confirmed LVSΔcapB mutants were then amplified on chocolate agar plates containing kanamycin (10 μg/ml).

The LVSΔcapB/Pgro-IglC strain amplified from chocolate agar was washed once with sterile saline, resuspended in 20% glycerol/saline solution, and then stored at −80° C. until use. Upon each use, the stock was thawed immediately at 37° C. and diluted in sterile saline.

LVSΔcapB/Pgro-AcpASS-IglC:

An F. tularensis protein fused to a signal peptide was designed to be expressed and secreted into the cytoplasm, such that the F. tularensis protein would be presented to MHC class I molecules and induce immune responses specific to the F. tularensis antigen. To construct such a fusion protein, IglC was fused with the signal sequence of F. tularensis AcpA. The coding sequence for IglC was fused with that for the N-terminal 28 amino acids (signal sequence plus 5 extra peptides) of AcpA by PCR, cloned the DNA fragment into the NdeI-BamHI sites of the pFNLTP6/gro-gfp plasmid downstream of the groE promoter, and engineered into the LVSΔcapB mutant as described above for the LVSΔcapB/Pgro-IglC strain. The resultant strain, LVSΔcapB/Pgro-AcpASS- IglC, was confirmed by colony PCR and amplified on chocolate agar plates containing kanamycin (10 µg/ml).

LVSΔcapB/Pgro-IglA:

The LVSΔcapB/Pgro-IglA strain was constructed as described above for LVSΔcapB/Pgro-IglC.

LVSΔcapB/PiglA-IglA:

Although it has no predicted signal sequence in the N-terminus, IglA is a cytoplasmic protein of *F. tularensis* under in vitro growth conditions. To examine whether the endogenous promoter of IglA would enhance the expression and secretion of IglA, the promoter and coding sequence for IglA was amplified by PCR and cloned into pZErO. The inserted sequence was confirmed by nucleotide sequencing and subcloned into the KpnI-BamHI sites of pFNLTP6/gro-gfp plasmid in place of the DNA sequence for the groE promoter and gfp. The resultant plasmid, pFNLTP6/PiglA-iglA, was introduced into LVSΔcapB to generate LVSΔcapB/PiglA-IglA as described above for LVSΔcapB/Pgro-IglC.

LVSΔcapB/Pgro-VgrG: The LVSΔcapB/Pgro-VgrG strain was constructed as described above for LVSΔcapB/Pgro-IglC.

LVSΔcapB/Pgro-IglB: The LVSΔcapB/Pgro-IglB strain is being constructed as described above for LVSΔcapB/Pgro-IglC.

Results:

(i) LVSΔcapB, which retains the O-Antigen, was serum resistant. (ii) In a competition experiment, LVSΔcapB was outgrown by parental LVS in THP-1 cells. (iii) LVSΔcapB was significantly attenuated in mice and caused no weight loss, obvious signs of illness, or deaths at any dose tested; hence the $LD_{50}$ i.n. was $>10^7$ CFU vs. $1.8 \times 10^3$ CFU for LVS and the $LD_{50}$ i.d. was $>10^8$ CFU vs. $3.2 \times 10^7$ CFU for LVS. (iv) Mice immunized with LVSΔcapB i.n. or i.d. and then challenged 4 weeks later with a lethal dose of LVS i.n. were 100% protected from illness and death. In mice immunized with LVSΔcapB, the bacterial burden in the lung was 3-5 logs lower than in sham-immunized animals, and the bacterial burden in the spleen and liver was 3-4 logs lower than in sham-immunized animals, comparable to that in mice immunized with LVS. This indicated that both local replication in the lung and systemic dissemination of *F. tularensis* was strongly inhibited by immunization with LVSΔcapB.

Example 2

Competition Assay for Growth in Human Macrophages.

To compare the growth of LVSΔcapB with its parental LVS strain in human macrophages, a pair of LVS strains carrying a kanamycin-resistance gene (LVS-kan) or a hygromycin-resistance gene (LVS-hyg) were constructed and a comparable pair of LVSΔcapB strains each carrying one of the same antibiotic resistance genes (LVSΔcapB-kan and LVSΔcapB-hyg). THP-1 cells were co-infected with LVSΔcapB-hyg and LVS-kan or co-infected with the same two strains carrying the opposite resistance markers (LVSΔcapB-kan and LVS-hyg). At various times post infection, the cell monolayer was lysed, serially diluted, and plated on chocolate agar supplemented with either kanamycin or hygromycin. Colony Forming Units (CFU) were enumerated and the ratio between the number of LVSΔcapB and LVS was calculated at each time point.

Analysis of Bacterial Lipopolysaccharide (LPS) and Protein Expression by Coomassie Blue Staining and Western Blotting.

LPS expression by the LVSΔcapB mutant was analyzed by Western blotting using the monoclonal antibody FB11 (Abcam Inc. MA), at a dilution of 1:5,000 and subsequently horseradish peroxidase-conjugated goat anti-mouse immunoglobulin G (Bio-Rad) at a dilution of 1:25,000. The blots were incubated with chemiluminescent substrate (Pierce) and the proteins were detected by exposing film to the blot. Protein expression by LVSΔcapB mutant was analyzed by Coomassie blue staining.

Vaccination and Challenge of Mice.

Mice were vaccinated by the i.d. or intranasal (i.n.) route. For i.d. vaccination, mice were shaved, decontaminated with 70% ethanol at the base of the tail and injected using 27G ½ cc Tuberculin syringes (Becton Dickson, N.J.) with 50 µL sterile phosphate buffered saline (PBS, Negative control), or with various doses of LVS (Positive Control) or LVSΔcapB diluted in 50 µl PBS. For i.n. vaccination, mice were anesthetized by intraperitoneal (i.p.) injection with Ketamine (80 mg/kg) and Xylazine (10 mg/kg), and vaccines were administered into the nostrils in a total volume of 20 µl sterile saline. At various times after vaccination, mice were either euthanized for immunology studies or challenged by the i.n. route at UCLA with 4000 CFU LVS ($>5 \times LD_{50}$), administered in the same way as i.n. vaccination, or by the aerosol route with $10 \times LD_{50}$ of the Type A *F. tularensis* SchuS4 strain. The aerosol challenge was conducted in a chamber of 5 cubic feet with the mice conscious and active, using a Glas-Col Inhalation Exposure System (Glas-Col, LLC, Terre Haute, Ind.). Challenged mice were weighed and monitored for illness and death for 3 weeks. Mice that met pre-determined humane endpoints for euthanasia were euthanized and counted as a death. Mean Survival Time (MST) was calculated by dividing the sum of the surviving days of all mice by the total number of mice examined, with animals surviving until the end of the experiment given a survival time of 21 days, when the experiment was terminated.

To quantitate bacterial burden in host tissues, mice were euthanized at 5 days post-infection. Liver, spleen, lung, and in the case of i.d. immunization, a 1-$cm^2$ area of local skin at the injection site were removed aseptically and immediately weighed, immersed in 2 ml sterile PBS and kept on ice until homogenization. The homogenization was performed using a Pro200 Homogenizer (PRO Scientific Inc. Oxford, Conn.). Serial 10-fold dilutions of the homogenates were plated onto Chocolate agar plates containing sulfamethoxazole (40 µg/ml), trimethoprim (8 µg/ml) and erythromycin (50 µg/ml), and incubated in a 5% $CO_2$ atmosphere at 37° C. for three days before colonies were enumerated.

Assay for Lymphocyte Proliferation.

Groups of four BALB/c mice were sham-immunized or immunized i.d. with $1 \times 10^5$ CFU LVS or $1 \times 10^6$ CFU LVSΔcapB or immunized i.n. with 200 CFU LVS or $1 \times 10^5$ CFU LVSΔcapB. At four weeks post immunization, mice were anesthetized by i.p. injection of Ketamine and Xylazine, bled and then euthanized. Sera were collected for serum antibody measurement as described below. Spleens were removed and a single cell suspension of splenocytes was prepared. Lymphocyte proliferation in response to heat-inactivated LVS antigen was assayed. Splenocytes from each animal were cultured in triplicate and stimulated with heat-inactivated LVS for 48 hours. Two hours before harvesting, the stimulated splenocytes were pulsed with methyl-[$^3$H]thymidine and harvested with a cell harvester (Skatron). The amount of incorporated [$^3$H]thymidine was determined by counting in a liquid scintillation counter.

Heat-inactivated LVS antigen was prepared for this assay by growing LVS on Chocolate II agar for 2 days, scraping the bacteria into PBS, and incubating at 80° C. for 1 hour. Loss of viability was confirmed by plating the antigen onto Chocolate II agar plates and incubating at 37° C. for 2 days. No colonies were detected on the plates, indicating that no viable bacteria survived heat-inactivation.

Serum Antibody Detection by Enzyme-Linked Immunosorbent Assay (ELISA).

Sera collected from sham-immunized mice or mice immunized with LVS or LVSΔcapB were analyzed for levels of IgM, IgA, IgG, IgG1 and IgG2a antibodies specific for LVS. The heat-inactivated LVS antigen was diluted in carbonate/bicarbonate buffer (50 mM $NaHCO_3$, 50 mM $Na_2CO_3$) to an optical density of 0.025 at 540 nm (equivalent to $5 \times 10^6$ CFU/0.1 ml) and 0.1 ml was used to coat 96-well high-binding capacity plates (Corning, N.Y.). Excess antigen was removed by washing three times with PBS. Sera at a starting dilution of 1:32 were diluted further through a two-fold series with PBS containing 1% bovine serum albumin. The diluted sera were incubated with the heat-inactivated LVS coated on 96-well plates at ambient temperature for 3 hours. The plates were subsequently incubated for 90 min at ambient temperature with alkaline phosphatase-conjugated goat anti-mouse IgA (Sigma, St. Louis, Mo.), IgM, IgG1 or IgG2a (Invitrogen, Camarillo, Calif.) at a dilution of 1:1000. The plates then were washed three times with PBS and 0.05% Tween-20. One hundred μl of p-nitrophenylphosphate substrate in diethanolamine buffer (Phosphatase Substrate kit, BioRad, Hercules, Calif.) was added to each well. The yellow color that developed was read at 414 nm for absorbance using a multiscan microplate reader (TiterTek, Huntsville, Ala.). The endpoint antibody titer was calculated as the reciprocal of the highest serum dilution that was a minimum of 0.05 optical density units above the sham-immunized control serum.

Statistical Analysis.

Two-way ANOVA with Bonferroni's post test was performed using GraphPad Prism version 5.01 (San Diego, Calif.) to determine significance in comparisons of mean SIs for lymphocyte proliferative responses, mean antibody titers, and mean Log CFU organ counts among mice in vaccinated and control groups. A log-rank analysis (Mantel-Cox test) using GraphPad Prism version 5.01 was used to determine significance of survival curves among mice in immunized and in sham-immunized control groups.

Construction and In Vitro Characterization of LVSΔcapB, an LVS Mutant Deficient in a Putative Capsule Synthesis Gene.

Figure 6:
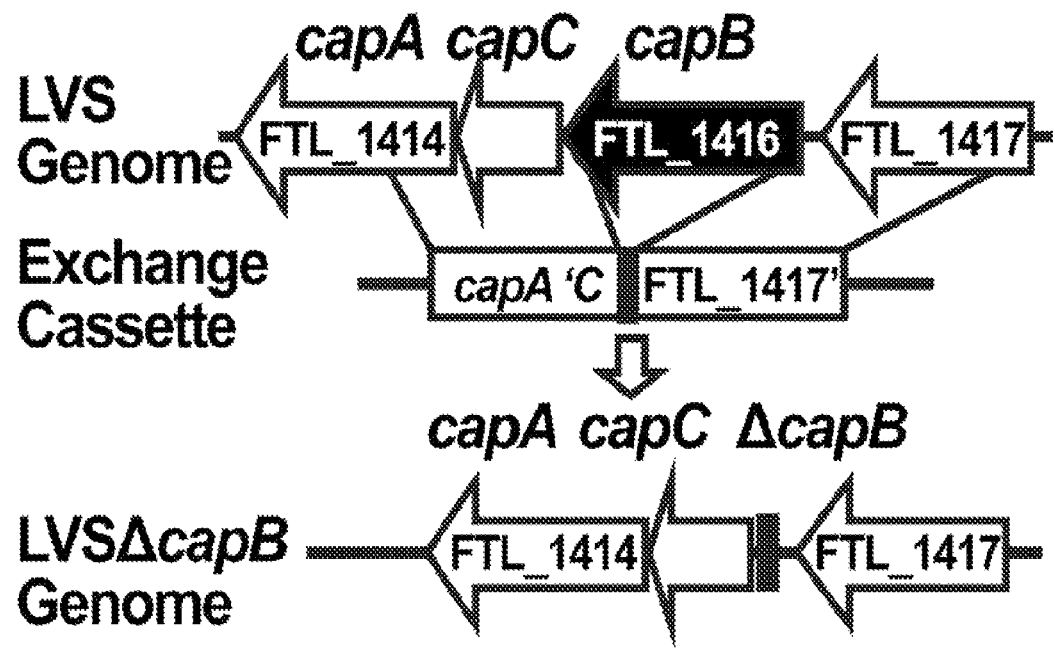
FIG. 6 shows construction of LVSΔcapB. LVSΔcapB was constructed by allelic exchange between LVS (top panel) and a plasmid carrying an exchange cassette containing flanking sequences to capB (FTL_1416/FTT0805), including the coding sequences for the C-terminal portion of capA and the full length capC (capA'C) on one side and the non-coding sequence between capB and FTL_1417 and the coding sequence for FTL_1417 (middle panel) on the other side. The resultant LVSΔcapB strain (bottom panel) retains 6 amino acids from the N-terminus and 4 amino acids from the C-terminus of CapB and contains no antibiotic resistance marker (unmarked).

The resultant LVSΔcapB mutant is free of the antibiotic resistance marker and the truncated capB contains 30 nucleotides encoding 6 amino acids from the N-terminus and 4 amino acids from the C-terminus of CapB (FIG. 6).

The LVSΔcapB Mutant Retains the O-Antigen.

Figure 2:
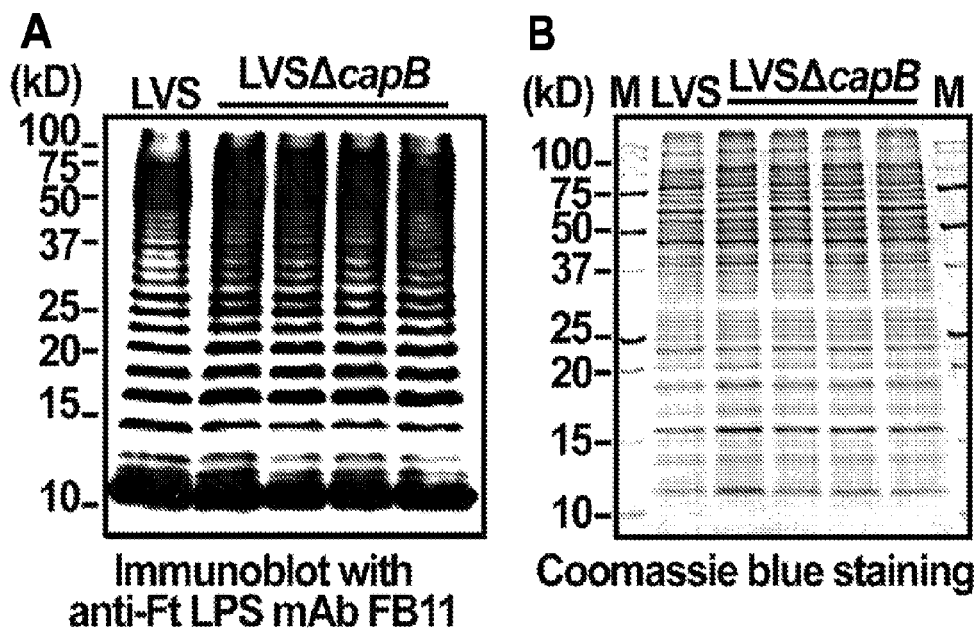
FIG. 2 shows that LVSΔcapB expresses the O-antigen. The bacteria lysate of LVS or four different clones of LVSΔcapB were anlalyzed by Western blotting (A) using anti-Ft LPS monoclonal antibody FB11 or by Coomassie blue staining for assessment of protein (B). Panel A shows the characteristic ladder pattern of LPS expressed by both strains. Panel B shows the protein pattern of each sample and that comparable amounts of each sample were loaded.

To determine whether LVSΔcapB produces LPS, bacterial lysates of LVS and LVSΔcapB were analyzed by Coomassie blue staining and Western blotting. Similar profiles of protein expression (FIG. 2B) and similar ladder-like patterns of LPS immunoreactivity (FIG. 2A) were observed for LVS and LVSΔcapB, confirming that the deletion of the capB gene did not affect retention of the LPS molecule.

the LVSΔcapB Mutant is not Sensitive to Serum-Killing.

Figure 3:
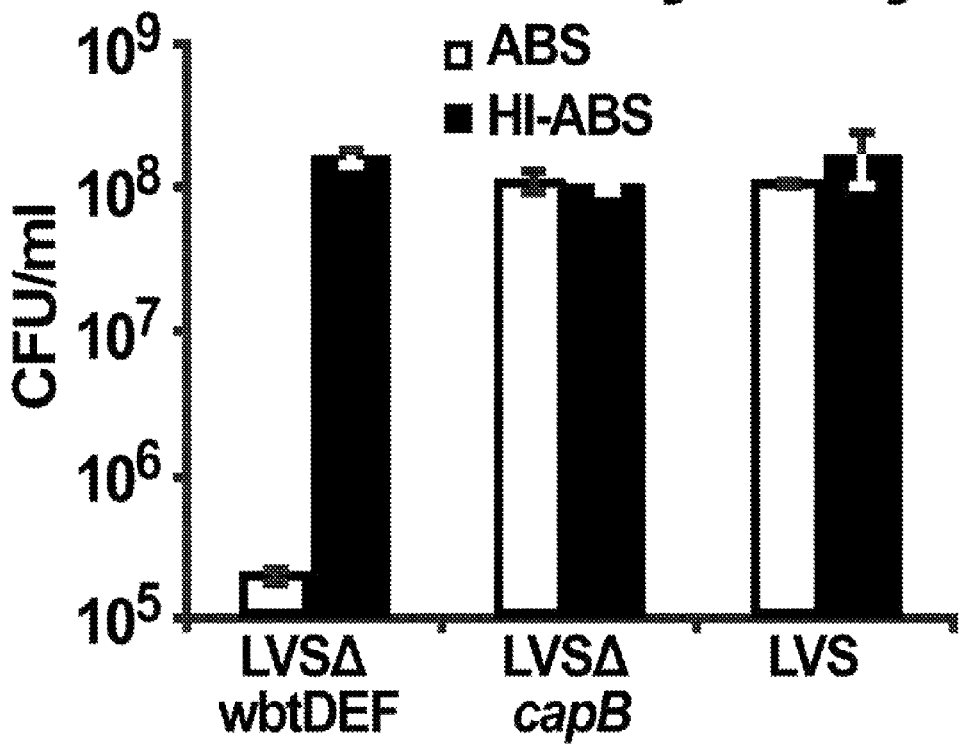
FIG. 3 shows that the LVSΔcapB mutant is not sensitive to serum killing. Each bacterial strain was incubated with either fresh AB serum (ABS) or heat-inactivated AB serum (HI-ABS) for 10 min and assayed for CFU on chocolate agar. Values represent means±standard errors.

To determine if the LVSΔcapB mutant is sensitive to serum, the strain was incubated with fresh serum and survival assessed by plating on agar (FIG. 3). Unlike the LVSΔwbt-DEF mutant, but similar to the parental LVS, the LVSΔcapB mutant was resistant to serum killing.

the LVSΔcapB Mutant is Attenuated for Growth in Macrophages.

Figure 4:
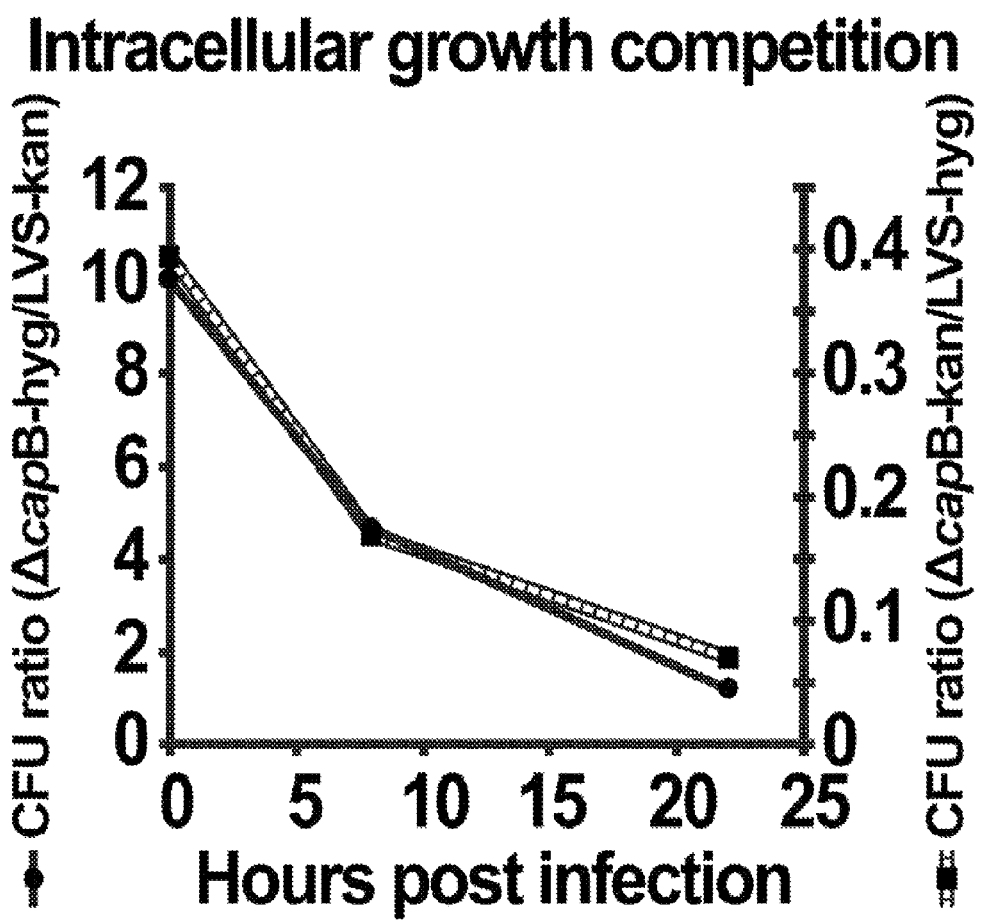
FIG. 4 shows that the LVSΔcapB mutant is attenuated for growth in human macrophages. THP-1 cells were co-infected with either LVSΔcapB carrying a hygromycin-resistance gene (ΔcapB-hyg) and LVS carrying a kanamycin-resistance gene (LVS-kan) (solid circle, left vertical axes) or vise versa i.e. with the same two strains carrying the opposite antibiotic resistance marker (solid square, right vertical axes). At the indicated hours post infection, the cell monolayer was lysed and serial dilutions of the lysate were plated on chocolate agar supplemented with either kan or hyg. CFU were counted and the ratio between the number of LVSΔcapB and LVS was calculated at each time point. The decrease in ratio over time indicates that LVS out-competed the LVSΔcapB strain.

To evaluate the attenuation of LVSΔcapB in vitro, the intramacrophage growth of LVSΔcapB was compared with that of LVS in human macrophages in a growth competition assay. The LVSΔcapB mutant carrying either a hygromycin- or kanamycin-resistance marker grew slower than the parental LVS strain carrying the opposite antibiotic resistance marker (kanamycin or hygromycin, respectively) (FIG. 4). This result indicated that the LVSΔcapB mutant is more attenuated than the parental LVS strain in human macrophages.

LVSΔcapB is More Attenuated than Parental LVS in Mice.

Figure 7:
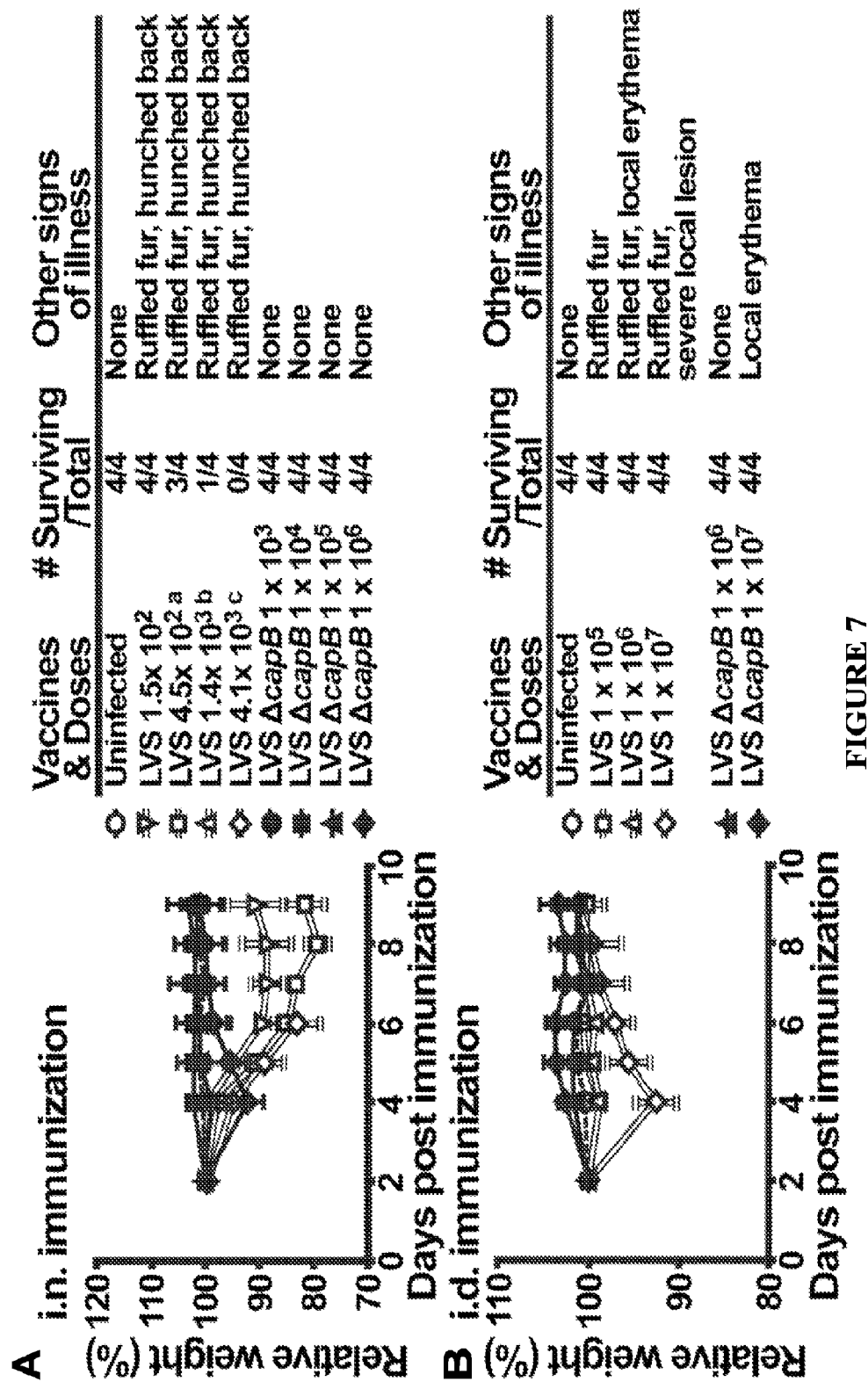
FIG. 7A-B shows LVSΔcapB is more attenuated than parental LVS in mice. Groups of 4 BALB/c mice were immunized i.n. (A) or i.d. (B) with LVS or LVSΔcapB at the indicated doses (CFU) and monitored for survival, weight change, local lesions (after i.d. immunization) and other signs of illness for 3 weeks. Relative weight at each time point was calculated as the percentage of the weight at day 2 post-immunization. Values are mean±SE. (A) the relative weight of surviving mice only is shown; (B) weight graphed only through day 6 post immunization at which time only 1 mouse survived; (C) all the mice in this group died by day 6 post immunization.

As described above, and consistent with the data above, to compare the virulence of LVSΔcapB with the parental LVS in vivo, BALB/c mice were immunized with a) LVSΔcapB at doses ranging from $1 \times 10^3$ to $1 \times 10^7$ CFU i.n. and $1 \times 10^8$ to $1 \times 10^8$ CFU i.d. or b) LVS at doses ranging from $1.5 \times 10^2$ to $4.1 \times 10^4$ CFU i.n. and $1 \times 10^5$ to $1 \times 10^7$ CFU i.d. Control mice were uninfected. The mice were observed for signs of illness, weight loss, death, and, in mice immunized i.d., the extent of a local lesion for three weeks. As shown in FIG. 7A, in mice administered LVS i.n., deaths occurred and at relatively low doses such that the $LD_{50}$ i.n. was 700 CFU (vs. $>10^7$ for LVSΔcapB). All mice immunized i.n. with LVS at each dose tested showed signs of illness (ruffled fur and hunched back) and they had significant weight loss between days 4 and 9 after immunization (FIG. 7A). In contrast, in mice immunized i.n. with LVSΔcapB, 100% of mice survived after immunization at all tested doses, and only transient weight loss occurred at around day 4 post-immunization, at a dose of $1 \times 10^6$ CFU (FIG. 7A) and in a separate experiment at a dose of $1 \times 10^7$ CFU/mouse.

In mice administered LVS i.d., 100% of mice survived after immunization at the doses tested in this experiment (FIG. 7B). However, in a separate experiment, 100% of mice died after i.d. immunization with $1 \times 10^8$ CFU LVS. In addition, mice immunized i.d. with $1 \times 10^7$ LVS developed severe local lesions. In contrast, in mice administered LVSΔcapB i.d., 100% of mice survived $10^6$-$10^8$ CFU doses (vs. 0% survival at a dose of $10^8$ CFU for LVS). Although mice immunized with LVSΔcapB i.d. at doses of $10^7$ (FIG. 7B) or $10^8$ CFU had transient weight loss, these mice had no other signs of illness and showed only mild local inflammation at the injection site.

In subsequent experiments evaluating the immunogenicity and efficacy of the i.d. route of immunization, doses of $10^6$ CFU of LVSΔcapB and $10^5$ CFU of LVS were generally used. At these doses, LVSΔcapB was non-toxic in mice and caused no apparent inflammation at the site of injection. In contrast, LVS retained significant toxicity, e.g. causing ruffled fur. In subsequent experiments evaluating the i.n. route of immunization, doses of $10^5$ CFU LVSΔcapB and 200 CFU LVS were generally used. Again, at these doses, LVSΔcapB was completely non-toxic, whereas LVS retained significant toxicity resulting in ruffled fur and hunched backs in immunized animals; moreover, in two experiments even this low dose of LVS proved lethal to 25% of immunized animals.

These results demonstrated that LVSΔcapB is at least 10,000-fold more attenuated than LVS after i.n. immunization and substantially more attenuated after i.d. immunization.

LVSΔcapB is Cleared Faster than LVS after Intranasal Infection.

Figure 8:
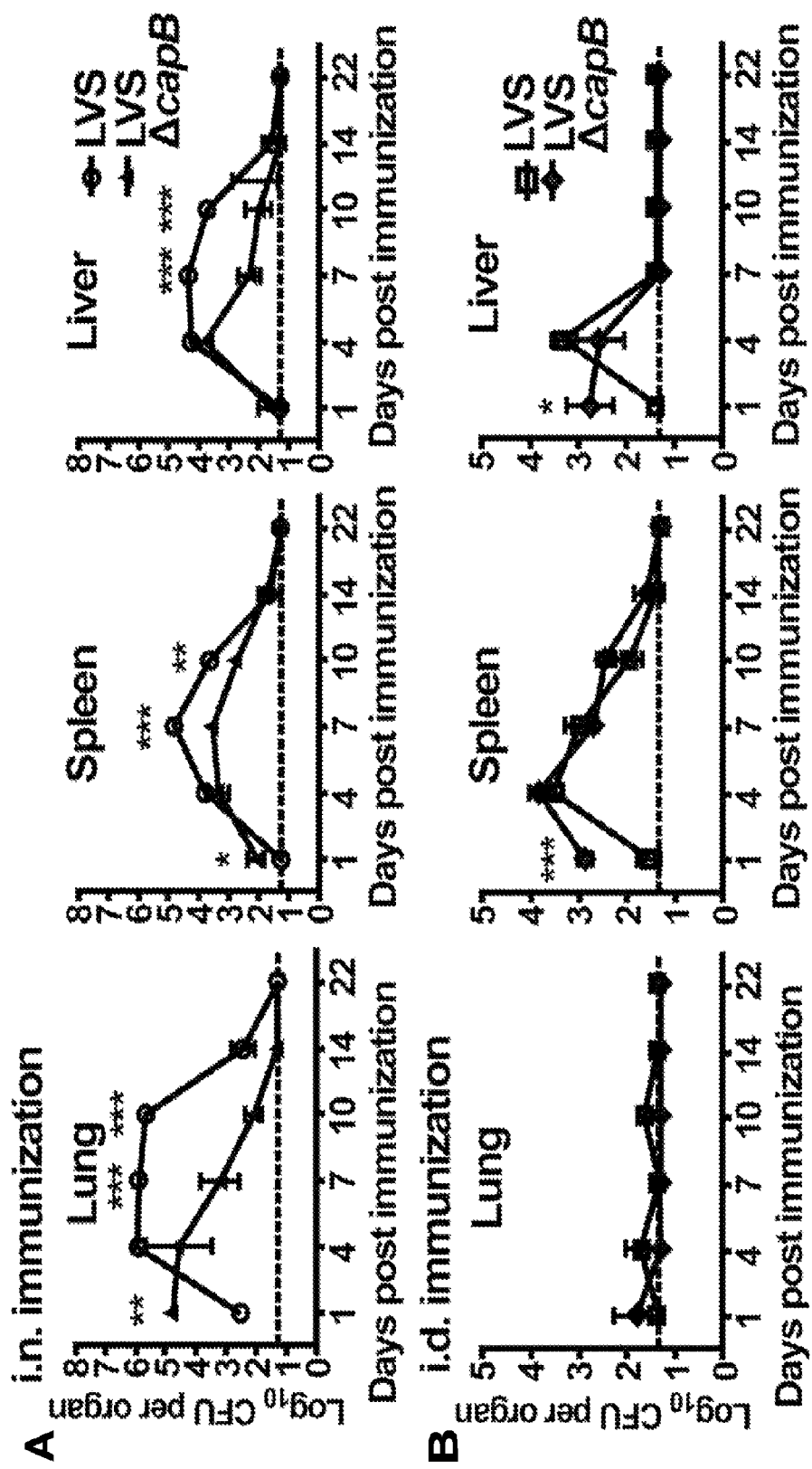
FIG. 8A-B shows dissemination and clearance of LVSΔcapB in mice. Groups of 4 BALB/c mice were immunized i.n. with 112 CFU LVS or $1 \times 10^5$ CFU LVSΔcapB or i.d. with $1 \times 10^5$ LVS or $1 \times 10^6$ LVSΔcapB. At the indicated times post-immunization, mice were euthanized and CFU in the spleen, liver, lung and skin at the site of injection (after i.d. immunization) assayed. LVSΔcapB is cleared faster than LVS in spleen, liver, and lung after i.n. immunization and at the site of injection in the skin after i.d. immunization. *, P<0.05; , P<0.01; *, P<0.001 by ANOVA.
Figure 8:
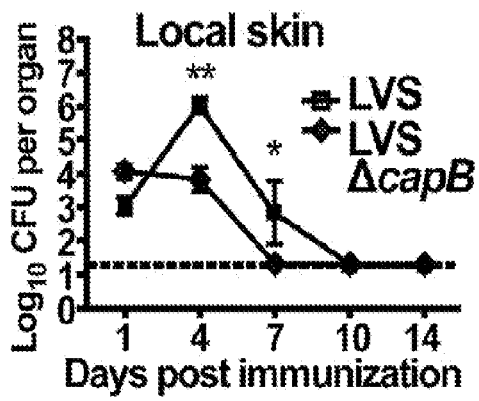

To assess dissemination and clearance of LVSΔcapB, groups of 4 BALB/c mice were immunized i.n. with 112 CFU LVS or $1 \times 10^5$ CFU LVSΔcapB or i.d. with $1 \times 10^5$ CFU LVS or $1 \times 10^6$ CFU LVSΔcapB. At various times post-immunization, mice were euthanized and spleen, liver, lung and skin at the injection site (in the case of i.d. immunization) were assayed for bacterial burden. As shown in FIG. 8A, following i.n. immunization, LVS replication peaked at day 4 in the lung and at day 7 in the spleen and liver; the LVS was cleared by day 22 post-immunization in all three organs examined. In contrast, although the LVSΔcapB mutant was administered at a much higher dose i.n. ($10^5$ CFU vs. 112 CFU for LVS), LVSΔcapB replicated at levels significantly lower than LVS at the peak of infection, and it was cleared faster than LVS in all three organs. Following i.d. immunization (FIG. 8B), the LVSΔcapB strain replicated less efficiently in the local injection area than the parental LVS strain. However, LVSΔcapB spread systemically to the liver and spleen, where it was cleared at a similar or greater rate than parental LVS strain. The replication of both LVSΔcapB and its parental LVS in the lung was limited (FIG. 8B).

These results demonstrated that LVSΔcapB is cleared much faster than LVS in mice after i.n. inoculation, and at least as fast as LVS after i.d. inoculation.

Immunization with LVSΔcapB Induces Strong Cell-Mediated and Humoral Immune Responses.

Figure 10:
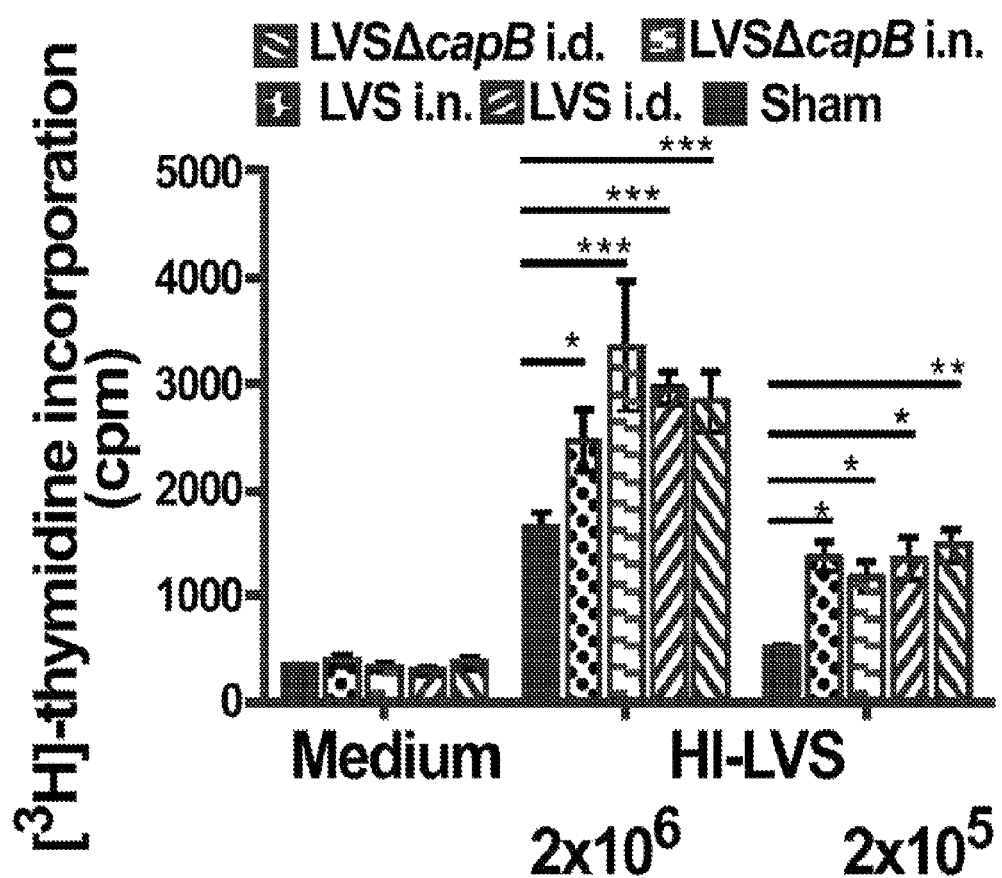
FIG. 10 shows immunization with LVSΔcapB induces cell-mediated immune responses comparable to those induced by LVS. Groups of 4 mice were immunized with LVS or LVSΔcapB by the i.n. or i.d. route. At 4 weeks post immunization, mice were euthanized and splenic lymphocyte proliferation assayed after incubation of splenocytes with heat-inactivated (HI) LVS for 48 hours. *p<0.05; p<0.01; and *p<0.001 by 2-way ANOVA.
Figure 11:
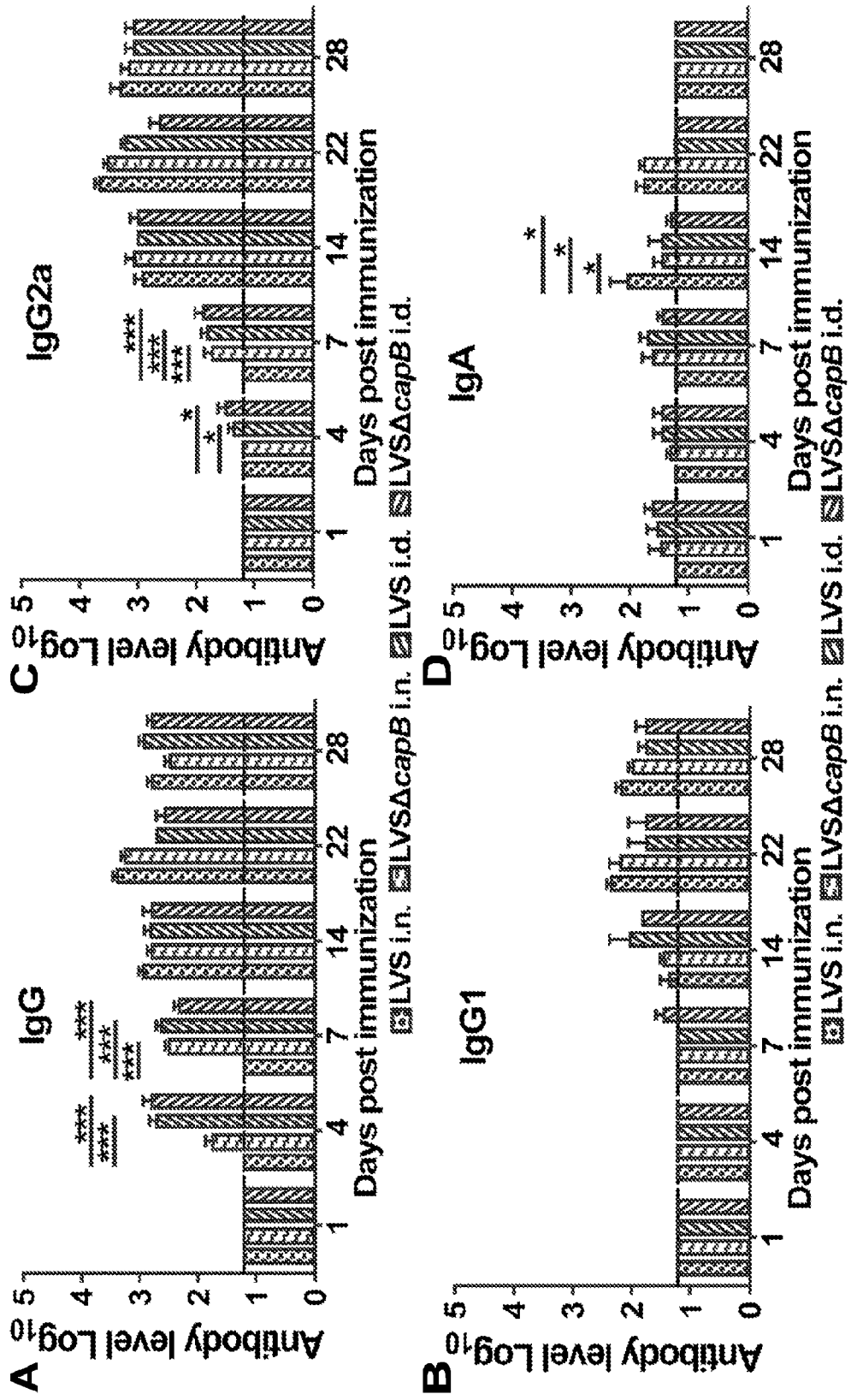
FIG. 11A-E shows immunization with LVSΔcapB induces potent antibody responses. The antibody level was calculated as $Log_{10}$ of the reciprocal of the endpoint dilution of the test serum. Data represent mean±SE. *, p<0.05; ***, p<0.001 by 2-way ANOVA.
Figure 11:
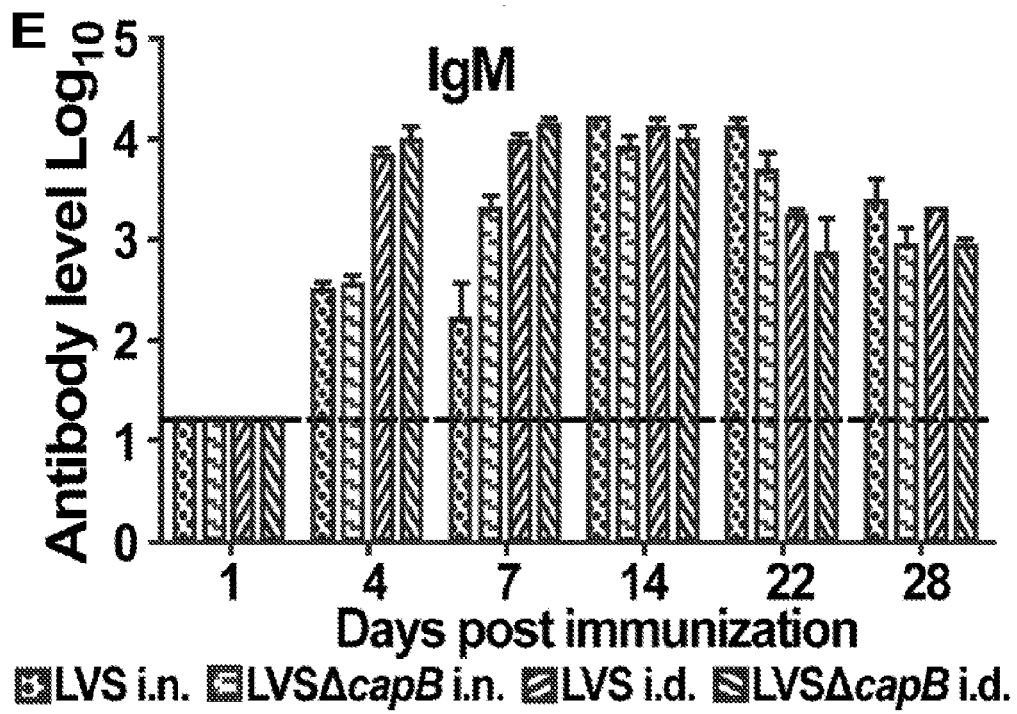

To examine whether immunization with LVSΔcapB induces cell-mediated and humoral immune responses, groups of 4 mice were immunized with LVSΔcapB at doses of $1 \times 10^5$ CFU by the i.n. route or $1 \times 10^6$ CFU by the i.d. route, doses that were non-toxic (FIG. 7) and that provided excellent protection against LVS i.n. challenge (see below). At 4 weeks post immunization, mice were anesthetized, bled and euthanized (FIG. 9A) and cell mediated and humoral immune responses assayed. With respect to cell-mediated immunity, immunization with LVSΔcapB i.n. or i.d. induced LVS-specific splenic lymphocyte proliferative responses that were significantly higher than those in sham-immunized mice and comparable to those in LVS-immunized mice (FIG. 10). With respect to humoral immune responses, following i.n. immunization, LVSΔcapB induced significantly higher levels of IgG antibody than LVS, predominantly IgG2a, within 7 days post immunization. IgG1 and IgG2a antibodies were detected in all mice immunized i.n. or i.d. with LVS or LVSΔcapB 14 days after immunization (FIG. 11A, B, C). Following i.n. or i.d. immunization, there were no significant differences in IgA and IgM antibody levels between mice immunized with LVS and those immunized with LVSΔcapB except that mice immunized i.n. with LVS had a transiently elevated IgA antibody level at 14 days post-immunization (FIGS. 11D and E).

Thus, LVSΔcapB, while highly attenuated, induces cellular and humoral immune responses comparable to those induced by LVS.

Immunization with LVSΔcapB Protects Mice from Lethal Intranasal Challenge with LVS.

Figure 9:
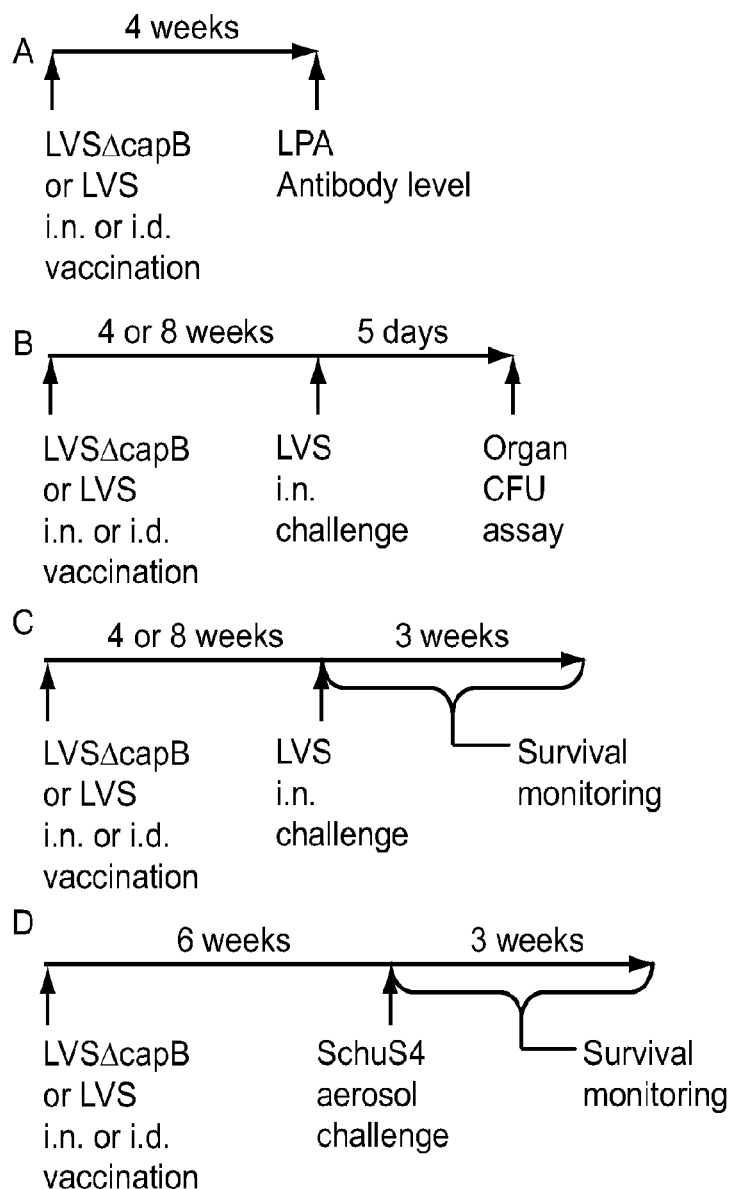
FIG. 9A-D shows immunization and challenge protocols. Groups of BALB/c mice were immunized i.n. or i.d. with LVSΔcapB or LVS. Mice immunized with PBS (Sham) or LVS served as controls. At the indicated times post immunization, mice were either euthanized for assaying lymphocyte proliferation (LPA) or serum antibody level(A) or challenged with approximately 4000 CFU LVS ($>5 \times LD_{50}$) by the i.n. route (B and C) or challenged with $10 \times LD_{50}$ of the Type A *F. tularensis* SchuS4 strain by the aerosol route (D). For assessment of organ bacterial burden, 4 or 8 mice per group challenged with LVS i.n. were euthanized at 5 days post-challenge and the organs were homogenized and assayed for CFU of LVS (B). For assessment of survival, 8 mice per group challenged with LVS i.n. or SchuS4 by aerosol were monitored for signs of illness and death for three weeks after challenge (C and D).

To examine the capacity of LVSΔcapB to induce protective immunity against lethal challenge with *F. tularensis*, mice were immunized i.n. or i.d with LVSΔcapB at various doses (FIGS. 9B, 9C, and 5). Sham-immunized mice and mice immunized with moderately well-tolerated doses of LVS (150 CFU i.n. and $1 \times 10^5$ or $1 \times 10^6$ CFU i.d.) served as controls. At 4 weeks post-immunization, mice were challenged i.n. with 4000 CFU LVS ($>5 \times LD_{50}$). Five days after challenge, approximately the peak time of bacterial growth in the host with an LVS i.n. challenge dose of 4000 CFU, mice were euthanized and the liver, spleen and lung were harvested and assayed for bacterial burden (FIG. 9B). As shown in FIG. 5, in mice immunized with LVSΔcapB i.n. or i.d., the bacterial burden in the spleen and liver was nearly 4 logs lower and the bacterial burden in the lung was 3-4 logs lower than in sham-immunized animals and comparable to the bacterial burden in mice immunized with LVS. The protection induced by immunization with LVSΔcapB was dose-dependent. Among all the doses of LVSΔcapB tested, $1 \times 10^5$ CFU i.n. and $1 \times 10^6$ CFU i.d. were both well-tolerated and induced protection in mice against *F. tularensis* challenge comparable to LVS. Therefore, in subsequent challenge experiments and the experiments described above in which immune responses were evaluated, these doses were used to immunize mice.

The above results indicated that both local replication in the lung and systemic dissemination of *F. tularensis* is strongly inhibited by immunization with LVSΔcapB.

Figure 12:
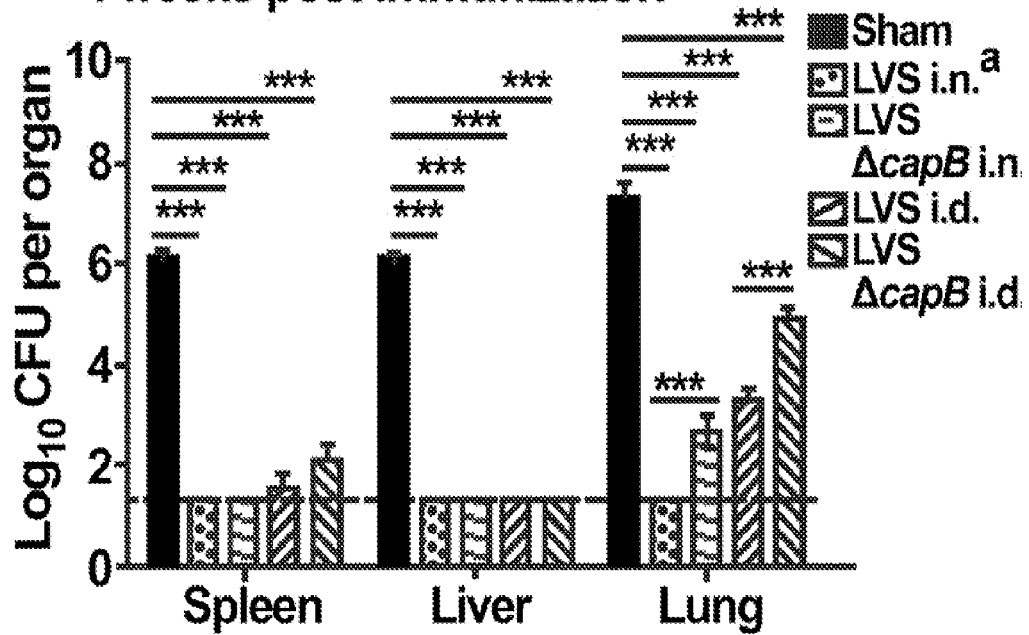
FIG. 12A-D shows immunization with LVSΔcapB induces protective immunity against i.n. LVS challenge comparable to that of the parental LVS. Groups of 12 mice were sham-immunized, immunized i.d. with $1 \times 10^5$ CFU LVS or $1 \times 10^6$ CFU LVSΔcapB, or immunized i.n. with 200 CFU LVS or $1 \times 10^5$ CFU LVSΔcapB. Four weeks (A and C) or eight weeks (B and D) later, mice were challenged i.n. with 4000 CFU LVS. A and B. At 5 days post-challenge, 4 mice per group were euthanized and the spleen, liver and lung assayed for bacterial burden. CFU values are shown as mean±SE. Dashed line, limit of detection. , P<0.01 and *, P<0.001 vs. sham-immunized mice by one-way ANOVA with bonferroni's post test (Prism 5). C and D. The remaining mice in each group were monitored for survival and signs of illness for 3 weeks. The difference in survival between the mice in the vaccinated groups and mice in the sham-vaccinated group were evaluated using a log-rank (Mantel-Cox) test (Prism 5.01). ***, P<0.0001 vs. Sham by log-rank (Mantel-Cox) test. $^a$, 3 of 12 mice (25%) died after i.n. immunization with LVS; of the remaining 9 mice, 4 were studied in Panel A and 5 in Panel C.
Figure 12:
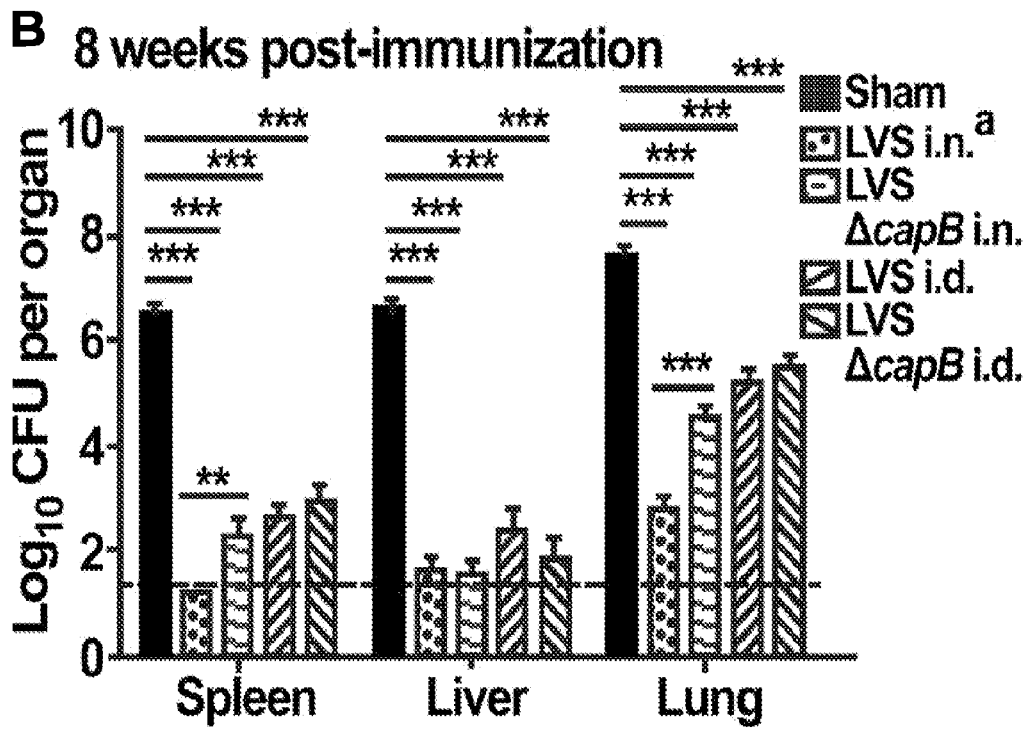
Figure 12:
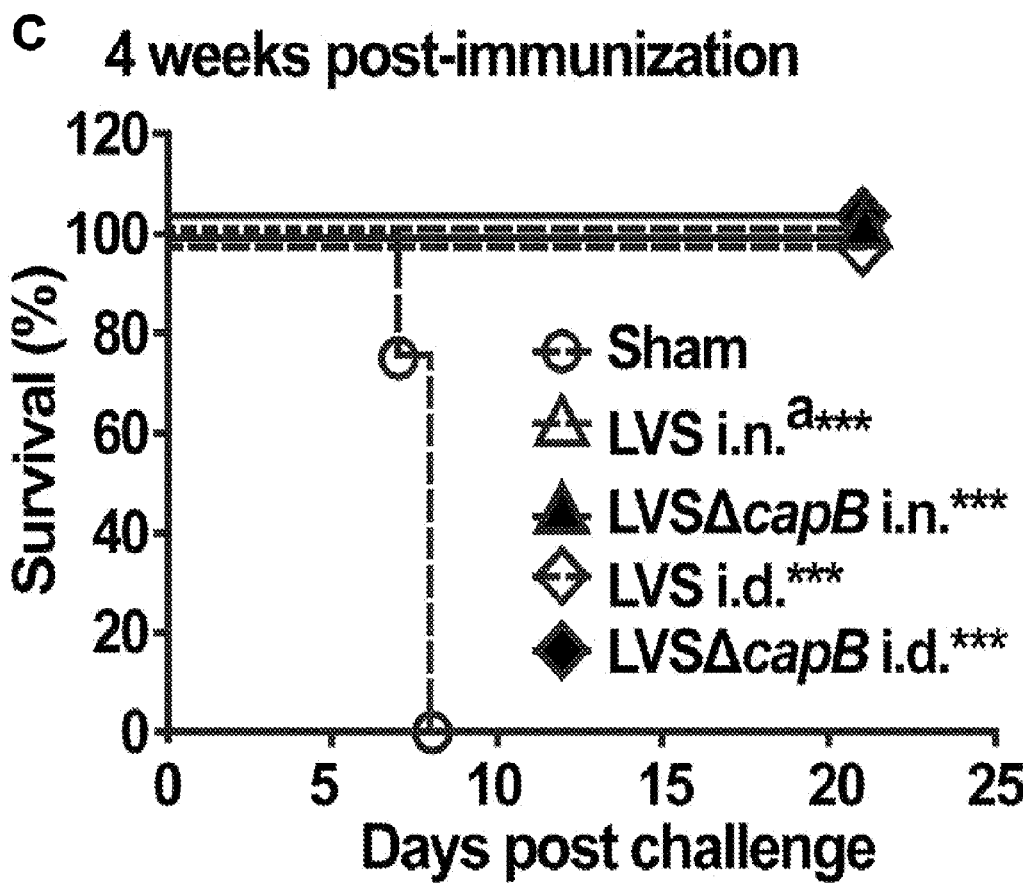
Figure 12:
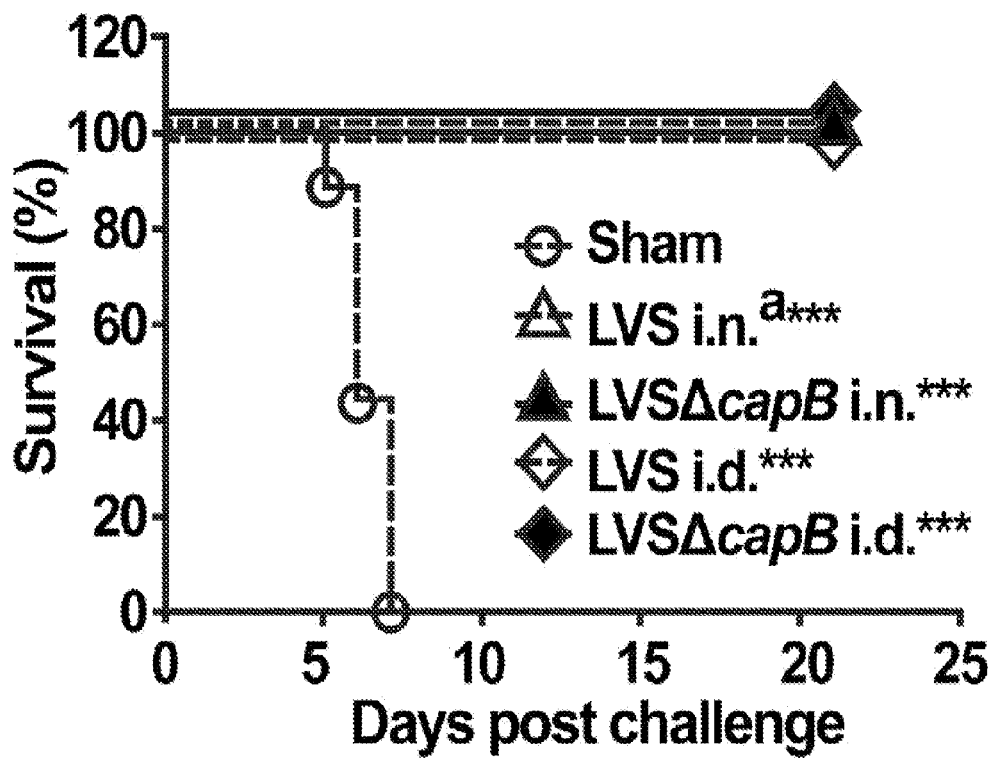

To further determine if immunization with LVSΔcapB can provide protection in mice against lethal LVS challenge, groups of 12 mice were immunized once i.n. with 200 CFU LVS (the maximum dose mice can usually survive) or $1 \times 10^5$ CFU LVSΔcapB, or once i.d. with $1 \times 10^5$ CFU LVS or $1 \times 10^6$ CFU LVSΔcapB. Notably, 25% (3/12) of mice immunized i.n. with just 200 CFU LVS died within 10 days of immunization, further underscoring the toxicity of LVS. In contrast, mice immunized with LVSΔcapB i.n. or i.d. did not shown any signs of illness. At 4 weeks post immunization, surviving mice were challenged i.n. with 4000 CFU LVS ($>5 \times LD_{50}$). Four of 12 mice in each group were euthanized at 5 days post challenge and lung, liver and spleen were removed for assay of bacterial burden. The remaining 8 mice in each group (except the LVS i.n. group, where only 5 mice remained) were monitored for signs of illness, weight loss and death for 3 weeks (FIG. 9C). Mice immunized i.n. or i.d. with LVSΔcapB and challenged 4 weeks later had lung bacterial burdens >4 logs lower after i.n. immunization and 2 logs lower after i.d. immunization than sham-immunized mice; CFU in the spleen was below the limit of detection after i.n. immunization and was 4 logs lower than sham-immunized mice, similar to mice immunized with LVS; and CFU in the liver were below the limit of detection after both i.d. and i.n. immunization, similar to mice immunized with LVS (FIG. 12A). Importantly, the bacterial burden in mice immunized with LVSΔcapB was 3 logs lower than in mice immunized with the LPS-deletion mutant LVSΔwbtDEF. Although mice immunized with LVSΔcapB had a somewhat higher bacterial burden in the lung than mice immunized with LVS, these mice showed no signs of illness after challenge. In the survival part of the study, 100% of mice immunized i.n. or i.d. with LVSΔcapB and challenged with LVS i.n. at 4 weeks post-immunization survived, the same as for mice immunized i.n. or i.d. with LVS (FIG. 12C).

To evaluate the protection provided by immunization with LVSΔcapB after a longer immunization-challenge interval, groups of 12 mice were immunized i.n. or i.d. with LVS or LVSΔcapB as described above and challenged i.n. with 4000 CFU LVS at 8 weeks post immunization. Again, 25% (3/12) of mice immunized i.n. with LVS died within 10 days of immunization, consistent with the results described above. At 5 days post challenge, mice immunized with LVSΔcapB i.n. or i.d. had significantly lower bacterial burdens than sham-immunized mice in all three organs examined (FIG. 12B). In animals immunized i.n., LVS-immunized animals had significantly fewer CFU in the spleen and lung than LVSΔcapB-immunized animals. In the liver, there was no significant difference in CFU between animals immunized with LVS and LVSΔcapB. In animals immunized i.d., there was no significant difference in CFU between LVSΔcapB- and LVS-immunized animals in any of the three organs assayed.

In the survival part of the study (FIG. 12D), all 8 sham-immunized animals died whereas all animals immunized with LVSΔcapB or LVS i.n. or i.d. survived (8 per group except the group immunized i.n. with LVS, where only 5 animals survived immunization).

Thus, LVSΔcapB, while much less virulent than LVS, induces potent protective immunity against lethal LVS i.n. challenge, comparable to that induced by LVS.

Figure 13:
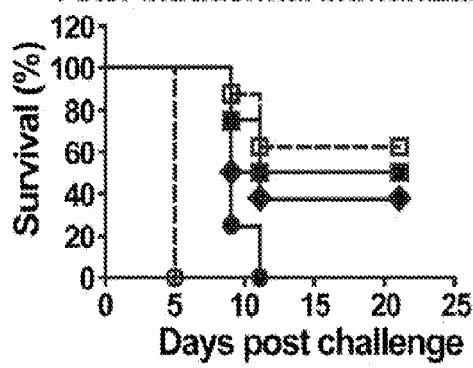
FIG. 13A-B shows immunizations with LVSΔcapB rLVSΔcapB/IglA and rLVSΔcapB/IglC induce protective immunity against F. tularensis SchuS4 aerosol challenge. Groups of 8 mice were sham-immunized, immunized i.d. (A) with $1 \times 10^5$ CFU LVS or $1 \times 10^6$ CFU LVSΔcapB, rLVSΔcapB/IglA, or rLVSΔcapB/IglC or immunized i.n. (B and D) with 200 CFU LVS or $1 \times 10^5$ CFU LVSΔcapB, rLVSΔcapB/IglA or rLVSΔcapB/IglC. Six weeks later, all mice were challenged by the aerosol route with $10 \times LD_{50}$ of the F. tularensis SchuS4 strain. Mice were monitored for survival for 3 weeks. Mean survival time was calculated by dividing the sum of the survival times of all mice in a group by the total number of mice challenged, with animals surviving until the end of the experiment given a survival time of 21 days, when the experiment was terminated. The difference in survival between the mice in the vaccinated groups and mice in the sham-vaccinated group were evaluated using a log-rank (Mantel-Cox) test (Prism 5).
Figure 13:
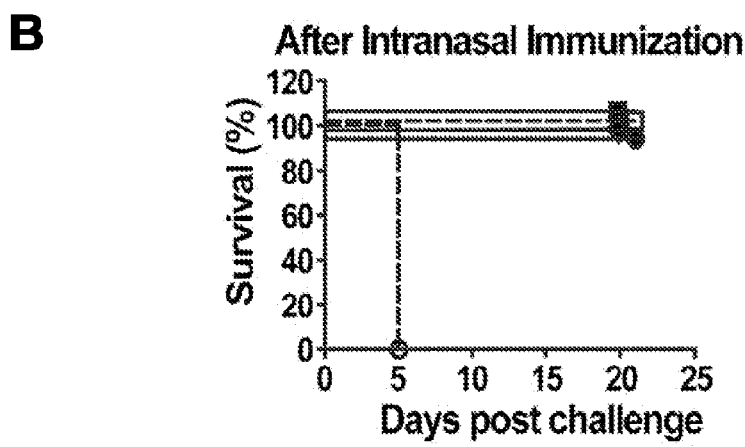

Immunization with LVSΔcapB protects mice from aerosol challenge with the virulent *F. tularensis* SchuS4 strain. To further define the protective immunity induced by immunization with LVSΔcapB, the capacity of the vaccine to protect against the highly virulent *F. tularensis* SchuS4 strain was analyzed. Groups of 8 mice were immunized once i.n. with $1\times10^5$ CFU LVSΔcapB or i.d. with $1\times10^6$ CFU LVSΔcapB, challenged the mice 6 weeks later by aerosol with $10\times LD_{50}$ *F. tularensis* SchuS4, and monitored the animals for weight change, signs of illness, and death for 3 weeks (FIG. 9D). Mice sham-immunized with PBS or immunized with LVS (200 CFU i.n. or $1\times10^5$ CFU i.d.) served as controls. Mice immunized with LVSΔcapB developed strong protective immunity to *F. tularensis* SchuS4 challenge (FIG. 13). In mice immunized i.d. (FIG. 13A), protection was incomplete. All LVSΔcapB and sham-immunized mice succumbed to challenge; however, LVSΔcapB-immunized mice survived twice as long (10 days) as sham-immunized mice (5 days, $P<0.0001$). LVS-immunized mice were better protected than LVSΔcapB-immunized mice (62.5% vs. 0% survival); however, all these mice showed substantial weight loss after challenge.

In mice immunized with LVSΔcapB i.n. (FIG. 13B), 100% of the mice survived challenge vs. 0% for sham-immunized animals ($p<0.0001$). Similarly, 100% of LVS-immunized animals survived. Notably, the LVSΔcapB and LVS-immunized animals showed no signs of illness after challenge, e.g. no weight loss.

Thus LVSΔcapB induces potent protective immunity to *F. tularensis* SchuS4 aerosol challenge, after both i.d. and i.n. immunization. Protection after i.n. immunization is stronger than after i.d. immunization and comparable to that induced by LVS.

Example 3

Figure 14A:
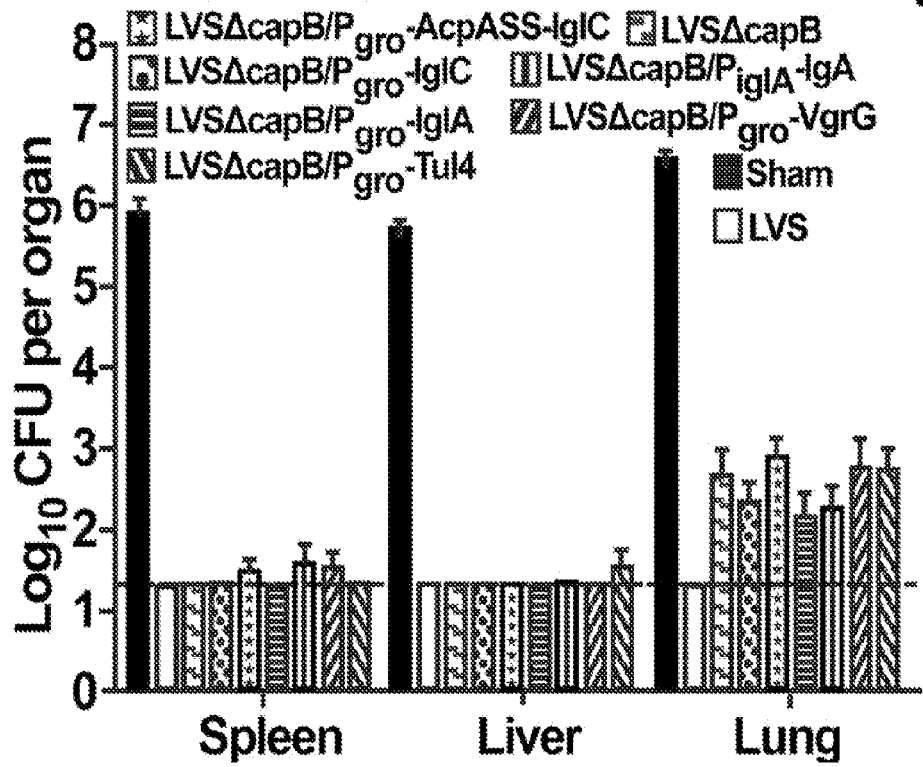
FIG. 14A-B shows protective immunity against i.n. challenge with F. tularensis 4 weeks after immunization with parental LVSΔcapB or rLVSΔcapB expressing F. tularensis proteins. BALB/c mice (4/group) were sham-immunized, or immunized i.n. (A) or i.d. (B) with LVS (200 CFU i.n. or $1 \times 10^5$ CFU i.d.), or with LVSΔcapB or LVSΔcapB expressing F. tularensis proteins ($1 \times 10^5$ CFU i.n. or $1 \times 10^6$ CFU i.d.). Four weeks later, the mice were challenged i.n. with 4000 CFU LVS. At 5 days post-challenge, the lung, spleen and liver were removed and assayed for bacterial burden. Values for each group are the mean±SE.
Figure 14B:
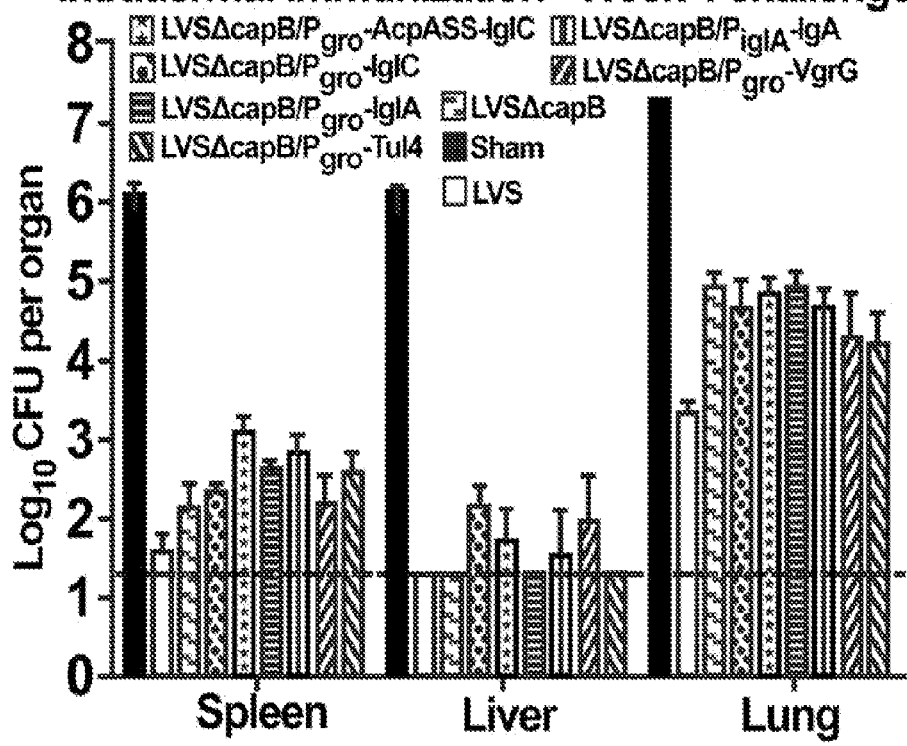
Figure 15A:
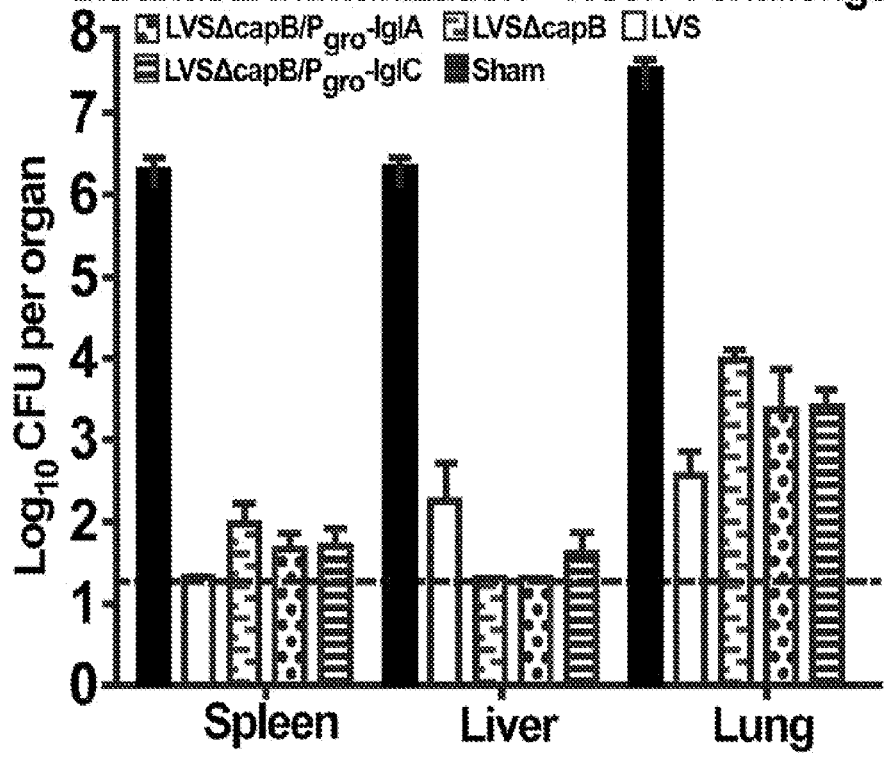
FIG. 15A-B shows protective immunity against i.n. challenge with F. tularensis 4 weeks after immunization with parental LVSΔcapB or rLVSΔcapB expressing F. tularensis IglA or IglC. BALB/c mice (4/group) were sham-immunized, or immunized i.n. (A) or i.d. (B) with LVS (200 CFU i.n. or $1 \times 10^5$ CFU i.d.), or with LVSΔcapB, LVSΔcapB/$P_{gro}$-IglA, or LVSΔcapB/$P_{gro}$-IglC ($1 \times 10^5$ CFU i.n. or $1 \times 10^6$ CFU i.d.). Four weeks later, the mice were challenged i.n. with 4000 CFU LVS. At 5 days post-challenge, the lung, spleen and liver were removed and assayed for bacterial burden. Values for each group are the mean±SE.

To examine the capacity of the attenuated rLVSΔcapB vaccines expressing *F. tularensis* proteins (IglA, IglC, VgrG, or Tul4) to induce protective immunity against lethal challenge with *F. tularensis*, mice were immunized with well-tolerated doses of LVSΔcapB, LVSΔcapB/$P_{gro}$-IglA, LVSΔcapB/$P_{iglA}$-IglA, LVSΔcapB/$P_{gro}$-IglC, LVSΔcapB/$P_{gro}$-AcpASS-IgC, LVSΔcapB/$P_{gro}$-VgrG, or LVSΔcapB/$P_{gro}$-Tul4 intranasally (i.n.) or intradermally (i.d.). Sham-immunized mice and mice immunized with LVS (200 CFU i.n. and $1\times10^5$ CFU i.d.) served as controls. Four weeks later, the mice were challenged with 4000 CFU of LVS i.n. (>5× $LD_{50}$). Five days after challenge, the peak time of bacterial growth in the host, mice were euthanized; the spleen, liver and lung removed and homogenized in sterile saline; the homogenate serially diluted and plated on CHA-HB plates; the plates incubated at 37° C. for 3 days; and CFU enumerated. As shown in FIG. 14, in mice immunized with LVSΔcapB i.n., the bacterial burdens in the spleen and liver were >4 logs lower and the bacterial burden in the lung was >3 logs lower than in sham-vaccinated animals. These results were consistent with the previous data, further demonstrating that both local replication in the lung and systemic dissemination of *F. tularensis* was strongly inhibited by immunization with the attenuated LVSΔcapB strain. Importantly, mice immunized i.n. with LVSΔcapB/$P_{gro}$-IgC, LVSΔcapB/$P_{gro}$-IglA, or LVSΔcapB/$P_{iglA}$-IglA had lower bacterial burdens in the lung than mice immunized with the parental LVSΔcapB strain, indicating that rLVSΔcapB vaccines expressing *F. tularensis* proteins induce greater protective immunity than the parental LVSΔcapB against lethal challenge with *F. tularensis* (FIG. 15A). Similarly, mice immunized i.d. with rLVSΔcapB vaccines, including LVSΔcapB/$P_{gro}$-IgC, LVSΔcapB/$P_{iglA}$-IglA, LVSΔcapB/$P_{gro}$-VgrG, LVSΔcapB/$P_{gro}$-Tul4, had lower bacterial burdens in the lung than mice immunized with the LVSΔcapB parental strain (FIG. 14B).

Example 4

Figure 15B:
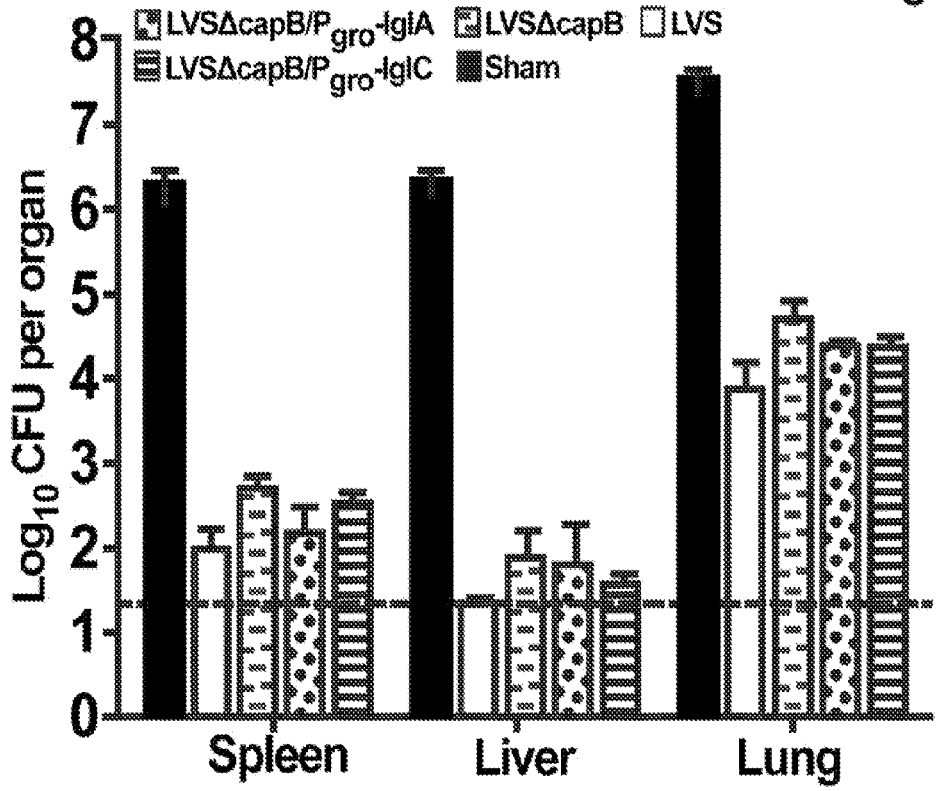

To confirm further the protective immunity induced by the rLVSΔcapB expressing IglA or IglC, the LVSΔcapB/$P_{gro}$-IgC and LVSΔcapB/$P_{gro}$-IglA vectors that induced greater protective immunity than the parental LVS LVSΔcapB strain were further analyzed. Groups of 4 mice were immunized i.n. or i.d. as described above in Example 3. 2 out 4 mice immunized i.n. with LVS died 7 days after immunization, confirming the toxicity of the LVS strain, even at the low dose used. However, mice immunized with LVSΔcapB, LVSΔcapB/$P_{gro}$-IgC or LVSΔcapB/$P_{gro}$-IglA did not show any signs of illness, confirming the safety of these vaccines. Four weeks after immunization, mice were challenged with 4000 CFU of LVS i.n. (>5× $LD_{50}$) and assayed for organ bacterial burden at 5 days post challenge. As shown in FIG. 15, in mice immunized i.n. with LVSΔcapB/$P_{gro}$-IgC or LVSΔcapB/$P_{gro}$-IglA, the bacterial burden in the lung and spleen was lower than in mice immunized with the parental LVSΔcapB strain. More importantly, in mice immunized with LVSΔcapB/$P_{gro}$-IgC or LVSΔcapB/$P_{gro}$-IglA via the i.d. route, a route that is safer than the i.n. route but also one by which it is more difficult to induce protective immunity, the bacterial burdens in the lung, spleen and liver were also lower than in mice immunized with the parental LVSΔcapB strain.

Example 5

Figure 16A:
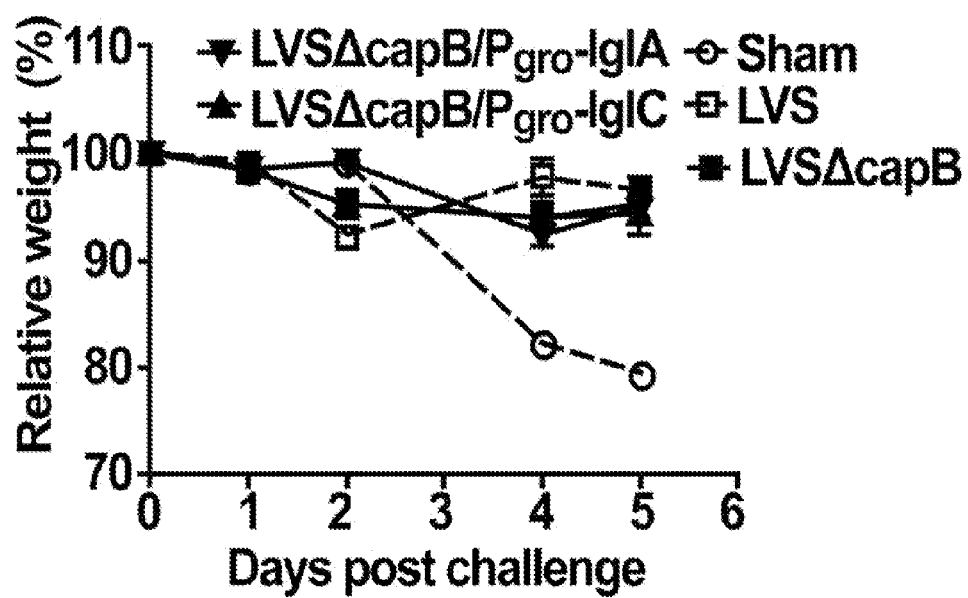
FIG. 16A-B shows protective immunity against i.n. challenge with F. tularensis 8 weeks after immunization with parental LVSΔcapB or rLVSΔcapB expressing F. tularensis IglA or IglC, as assessed by assay of weight loss after challenge. BALB/c mice (4/group) were sham-immunized, or immunized i.n. (A) or i.d. (B) with LVS (200 CFU i.n. or $1 \times 10^5$ CFU i.d.), or with LVSΔcapB, LVSΔcapB/$P_{gro}$-IglA, or LVSΔcapB/$P_{gro}$-IglC ($1 \times 10^5$ CFU i.n. or $1 \times 10^6$ CFU i.d.). Four weeks later, the mice were challenged i.n. with 4000 CFU LVS and monitored for relative weight change. Values for each group are the mean±SE of the weight at each time point as a percent of the weight at day 0 post challenge.
Figure 16B:
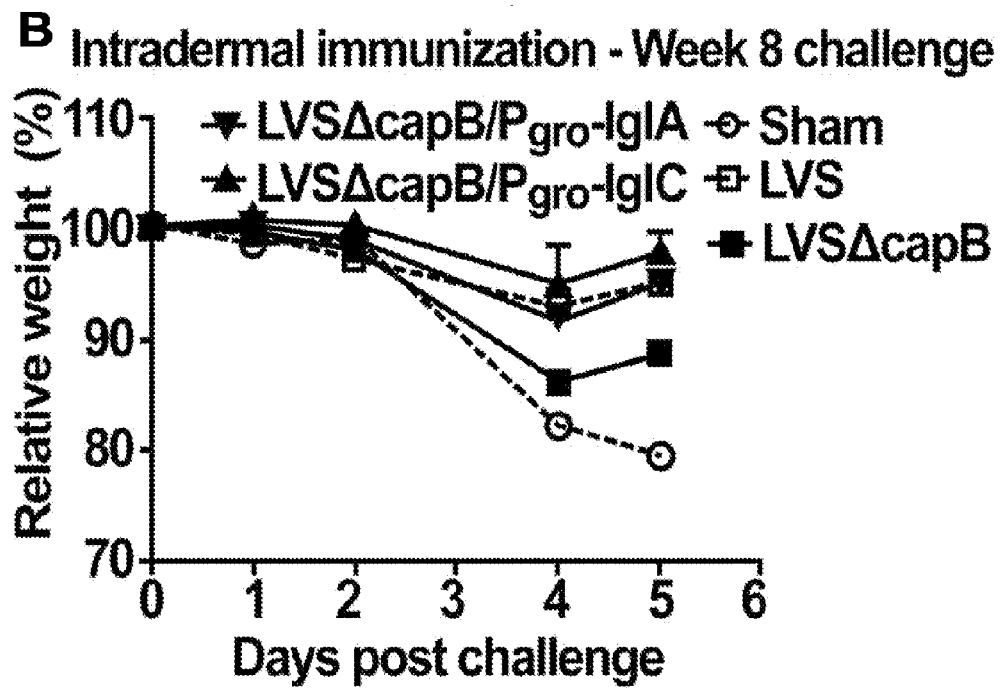
Figure 17A:
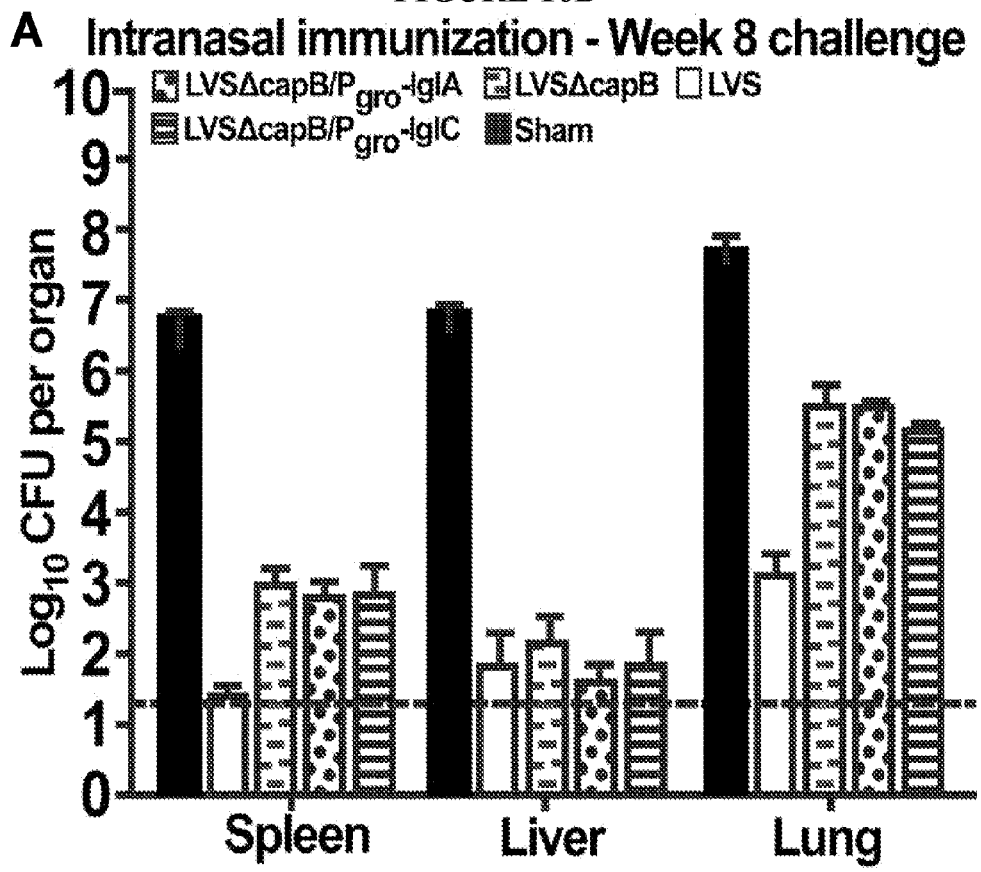
FIG. 17A-B shows protective immunity against i.n. challenge with F. tularensis 8 weeks after immunization with parental LVSΔcapB or rLVSΔcapB expressing F. tularensis IglA or IglC, as assessed by assay of organ burden after challenge. BALB/c mice (4/group) were sham-immunized, or immunized i.n. (A) or i.d. (B) with LVS (200 CFU i.n. or $1 \times 10^5$ CFU i.d.), or with LVSΔcapB, LVSΔcapB/$P_{gro}$-IglA, or LVSΔcapB/$P_{gro}$-IglC ($1 \times 10^5$ CFU i.n. or $1 \times 10^6$ CFU i.d.). Eight weeks later, the mice were challenged i.n. with 4000 CFU LVS. At 5 days post-challenge, the lung, spleen, and liver were removed and assayed for bacterial burden. Values in each group are the mean±SE.
Figure 17B:
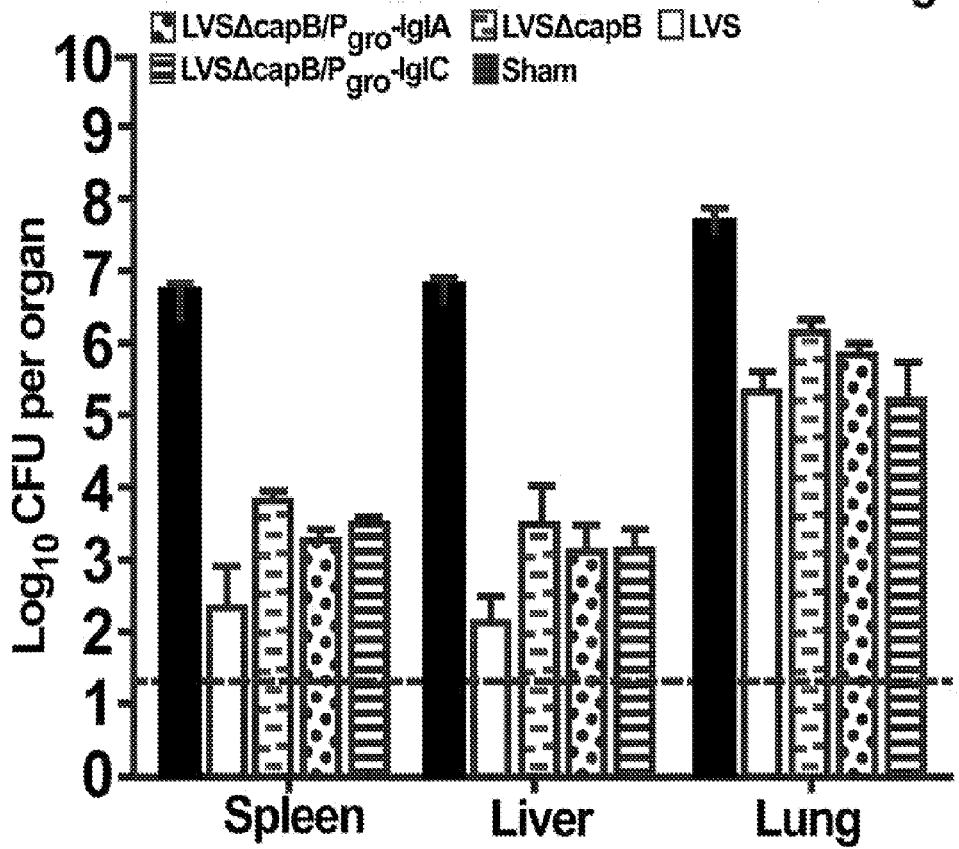

To evaluate whether rLVSΔcapB vaccines expressing *F. tularensis* proteins induce longer-term immunity against high dose *F. tularensis* challenge, groups of 4 mice were immunized i.n. or i.d. with LVS, LVSΔcapB, LVSΔcapB/$P_{gro}$-IgC or LVSΔcapB/$P_{gro}$-IglA as described above in Example 3 and 4. Again, 2 out of 4 mice died 7 days after i.n. immunization with LVS. Eight weeks later, mice were challenged with $6.3\times10^4$ CFU LVS i.n. (≈90× $LD_{50}$) and monitored for weight loss and other signs of illness daily. At 5 days post challenge, mice were euthanized and the bacterial burdens in lung, spleen, and liver were determined. As shown in FIGS. 17A and 17B, the sham-immunized mice had significant weight loss after challenge. In contrast, mice immunized i.n. with LVSΔcapB, LVSΔcapB/$P_{gro}$-IgC or LVSΔcapB/$P_{gro}$-IglA did not show signs of illness after challenge—nor did the two mice that survived i.n. immunization with LVS (FIG. 16A). Notably, mice immunized i.d. with the parental LVSΔcapB showed substantial weight loss after challenge, whereas mice immunized i.d. with LVSΔcapB/$P_{gro}$-IgC or LVSΔcapB/$P_{gro}$-IglA did not show weight loss or other signs of illness, comparable to mice immunized with LVS (FIG. 16B). Importantly, in mice immunized i.n. or i.d. with LVSΔcapB/$P_{gro}$-IgC or LVSΔcapB/$P_{gro}$-IglA, the bacterial burdens in the lung, spleen, and liver were consistently lower than in mice immunized with the parental LVSΔcapB strain, and comparable to the levels in mice immunized with LVS (FIG. 17). Thus, overexpressing *F. tularensis* proteins, especially IglA and IglC, in the parental LVSΔcapB vector yields vaccines that are of greater potency than the parental LVSΔcapB vector. These results further confirmed demonstrate that an attenuated homologous vector overexpressing immunogenic proteins of a specific intracellular pathogen induces greater protective immunity than the parental vector alone.

Example 6

Figure 18A:
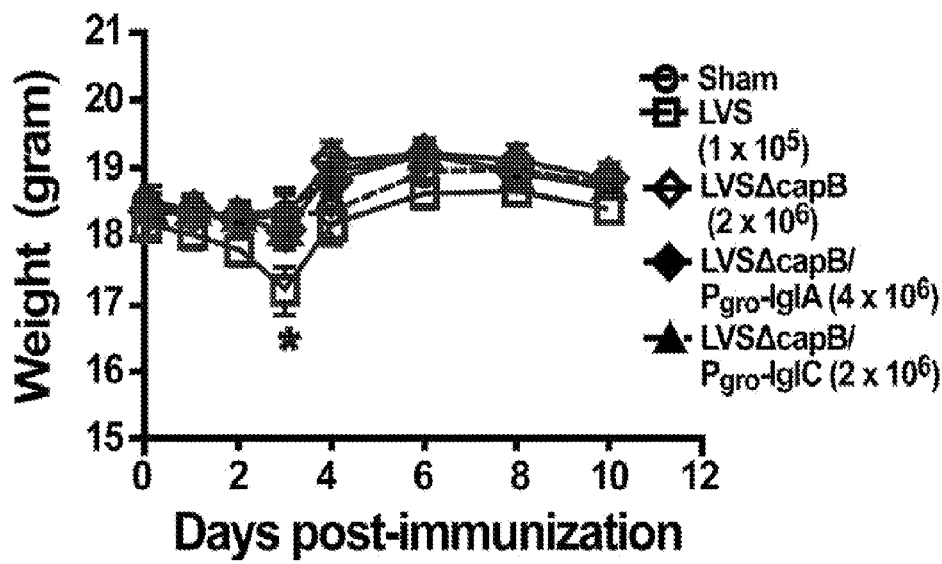
FIG. 18A-B shows safety of LVSΔcapB or rLVSΔcapB expressing F. tularensis IglA or IglC as assessed by weight loss after immunization. BALB/c mice were sham-immunized, or immunized i.d. (A, 24 mice/group) or i.n. (B, 8 mice/group) with LVS, LVSΔcapB, LVSΔcapB/$P_{gro}$-IglA, or LVSΔcapB/$P_{gro}$-IglC at doses (CFU) shown in parentheses to the right of the name of each vaccine. The immunized mice were monitored for signs of illness and weighed at the indicated times after immunization. Values in each group are the mean±SE. In Panel A, *, P<0.05, LVS versus the following: Sham, LVSΔcapB, LVSΔcapB/$P_{gro}$-IglA or LVSΔcapB/$P_{gro}$-IglC, by one-tailed t-test. In Panel B, ***, P<0.001, LVS versus each of the following at days 6, 8, and 10: Sham, LVSΔcapB, LVSΔcapB/$P_{gro}$-IglA or LVSΔcapB/$P_{gro}$-IglC by two-way ANOVA (GraphPad Prism 5) with Bonferroni post-tests. #, 1 mouse immunized i.n. with LVS died at the indicated time points; thus the result for LVS at day 10 (Panel B) is for the remaining 6 animals in the group.
Figure 18B:
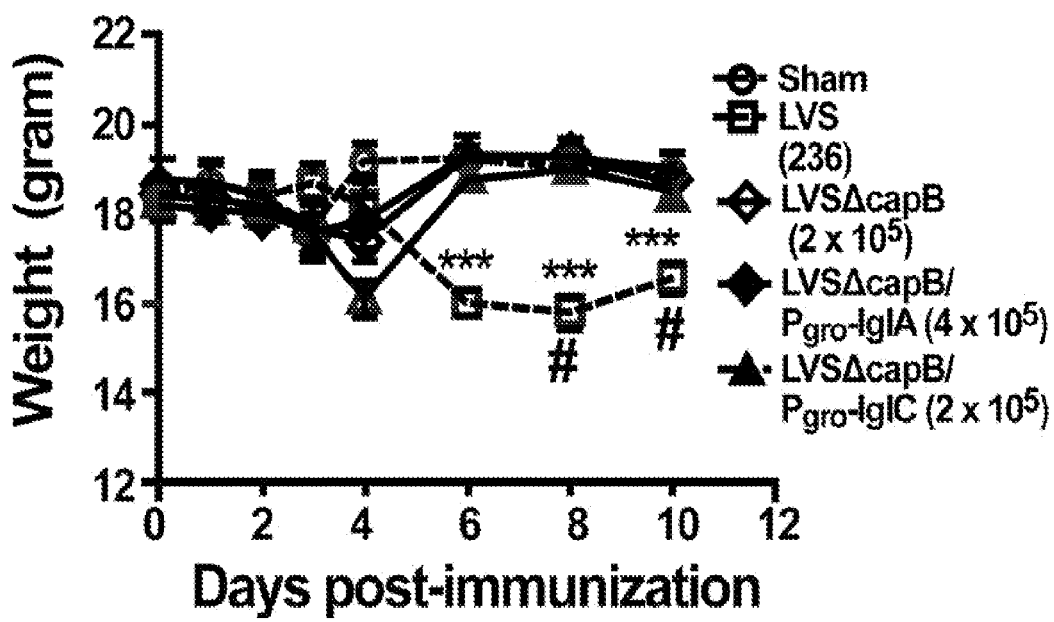

To further evaluate rLVSΔcapB vaccines expressing *F. tularensis* proteins, groups of 24 BALB/c mice were sham-immunized or immunized by the i.d. route with LVS (targeted dose 1×10$^5$ CFU/mouse), or with LVSΔcapB, LVSΔcapB/ P$_{gro}$-IgA or LVSΔcapB/P$_{gro}$-IglC (1×10$^5$ CFU/mouse). Groups of 8 BALB/c mice were also immunized by the i.n. route with LVS (targeted dose 200 CFU/mouse), or LVSΔ-capB, LVSΔcapB/P$_{gro}$-IgC or LVSΔcapB/P$_{gro}$-IglA (targeted dose 1×10$^5$ CFU/mouse). The immunization dose actually delivered for each vaccine was determined by plating serial dilutions of the inocula onto Chocolate agar. After immunization, mice were monitored for weight change and signs of illness. As shown in FIG. 18A, mice immunized with 2×10$^5$ CFU LVS had significant weight loss at day 3 post-immunization. In contrast, mice immunized with 2-4×10$^6$ CFU of LVSΔcapB, LVSΔcapB/P$_{gro}$-IgA or LVSΔcapB/P$_{gro}$-IglC did not show signs of illness, including weight loss, after immunization. As shown in FIG. 18B, mice immunized with 236 CFU LVS i.n. had significant weight loss between days 4 and 10 post-immunization and 2 out of 8 mice in this group died after immunization. Mice immunized with LVSΔcapB/ P$_{gro}$-IglC had transient weight loss around day 4 post-immunization. Mice immunized with LVSΔcapB or LVSΔcapB/ P$_{gro}$-IglA did not show significant weight loss after immunization. Although the rLVSΔcapB vaccines were administered i.d. at doses 20-40 times higher than LVS and administered i.n. at doses ~800-1600-fold higher than LVS, the rLVSΔcapB vaccines were significantly less toxic than LVS.

Example 7

Groups of 8 mice were sham-immunized, immunized i.d. (A) with 1×10$^5$ CFU LVS or 1×10$^6$ CFU LVSΔcapB, rLVS-ΔcapB/IglA, or rLVSΔcapB/IglC or immunized i.n. (B) with 200 CFU LVS or 1×10$^5$ CFU LVSΔcapB, rLVSΔcapB/IglA or rLVSΔcapB/IglC. Six weeks later, all mice were challenged by the aerosol route with 10×LD$_{50}$ of the *F. tularensis* SchuS4 strain. Mice were monitored for survival for 3 weeks. Mean survival time was calculated by dividing the sum of the survival times of all mice in a group by the total number of mice challenged, with animals surviving until the end of the experiment given a survival time of 21 days, when the experiment was terminated. The difference in survival between the mice in the vaccinated groups and mice in the sham-vaccinated group were evaluated using a log-rank (Mantel-Cox) test (Prism 5). As shown in FIG. 13A, mice immunized i.d. with rLVSΔcapB/IglA or rLVSΔcapB/IglC had a greater survival rate and survived longer (MST) than mice immunized with the parental LVSΔcapB (P=0.01 and 0.09, respectively); the survival rate for mice immunized with both vaccines was not significantly different from that of mice immunized with LVS. In mice immunized i.n. with rLVSΔcapB/IglC or rLVS-ΔcapB/IglA, 100% of mice survived, the same as for mice immunized i.n. with LVS and LVSΔcapB (FIG. 13B). These results show that LVSΔcapB overexpressing a single Ft protein (i.e. IglC or IglA—especially IglA) induces significantly enhanced protective immunity compared with parental LVS-ΔcapB and protective immunity is comparable to LVS by both the i.n. and more demanding i.d. route.

Example 8

Figure 19:
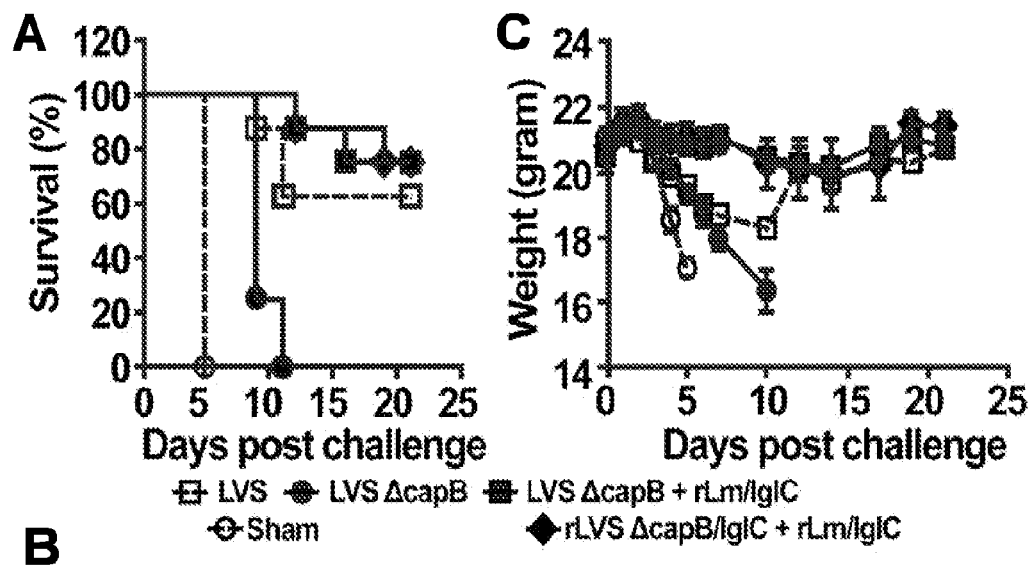
FIG. 19A-C shows that a heterologous prime-boost vaccination strategy using intradermally administered LVSΔcapB or rLVSΔcapB/$P_{gro}$-IglC as the prime and a recombinant attenuated Listeria monocytogenes vaccine expressing IglC as the boost induces strong protective immunity against aerosol challenge with the highly virulent F. tularensis SchuS4 strain. (A, B) Survival. Percent survival was computed at each time point. The difference in survival between the mice in each of the vaccinated groups and mice in the sham-vaccinated group was evaluated using a log-rank (Mantel-Cox) test (Prism 5). Similarly, the difference in survival between the mice in the LVS-vaccinated group and mice in each of the other groups was evaluated using a log-rank (Mantel-Cox)

To evaluate a prime-boost vaccination strategy, mice were immunized i.d. with LVSΔcapB or rLVSΔcapB/IglC, boosted them i.d. with rLm/iglC 3 weeks later, and challenged them 6 weeks later with aerosolized Ft SchuS4. Mice sham-immunized or primed i.d. with LVS or LVSΔcapB and not boosted served as controls (FIG. 19). Mice primed i.d. with rLVSΔ-capB or rLVSΔcapB/IglC and boosted with rLm/iglC had greater survival and survived longer (MST) than mice immunized i.d. with only parental LVSΔcapB (FIG. 19A, B). None of the surviving mice showed weight loss (FIG. 19C), indicating high level protection; importantly, the survival rate and MST for these mice were greater than for mice immunized i.d. with LVS, although the difference did not reach statistical significance (FIG. 19B). Moreover, in contrast to mice immunized with the prime-boost vaccine, mice immunized with LVS suffered significant weight loss (P<0.05 on Day 7 after challenge; FIG. 19C). These results indicate that heterologous boosting with rLm/iglC significantly enhances the protective immunity induced by i.d. immunization with the parental LVSΔcapB strain, and that the heterologous prime-boost vaccination strategy yields a vaccine that is both safer and more potent than LVS.

The disclosure demonstrates that (i) LVSΔcapB is serum resistant but significantly attenuated in both human macrophages and mice, providing a safer vaccine candidate than LVS. (ii) Immunization with LVSΔcapB by the i.d. or i.n. route induces strong protective immunity, comparable to that induced by LVS at maximum tolerated doses, against lethal i.n. challenge with *F. tularensis* LVS. (iii) Immunization with LVSΔcapB by the i.d. or i.n. route induces strong protective immunity against aerosol challenge with *F. tularensis* subspecies *tularensis*. By the i.n. route, LVSΔcapB induces protection comparable to LVS (100% protection). (iv) Immunization with rLVSΔcapB expressing *F. tularensis* antigens IglA or IglC by the i.d. or i.n. route induces strong protective immunity against aerosol challenge with *F. tularensis* subspecies *tularensis*, comparable to that induced by LVS at maximum tolerated doses. (v) Immunization intradermally with a heterologous prime-boost vaccine utilizing as a prime either LVSΔcapB or rLVSΔcapB/IglC and as a boost rLm/ IglC induces strong protective immunity against aerosol challenge with *F. tularensis* subspecies *tularensis*, and protection is greater than that induced by LVS at maximum tolerated doses.

```
                    Sequence Listing acpA                              (SEQ ID NO: 1 and 2)

bfr                               (SEQ ID NO: 3 and 4)

dnaK                              (SEQ ID NO: 5 and 6)
(70-kDa heat shock protein)

fabD                              (SEQ ID NO: 7 and 8)

groEL                             (SEQ ID NO: 9 and 10)

iglC                              (SEQ ID NO: 11 and 12)

katG                              (SEQ ID NO: 13 and 14)

pld                               (SEQ ID NO: 15 and 16)

sodB                              (SEQ ID NO: 17 and 18)

capB                              (SEQ ID NO: 19 and 20)

iglA                              (SEQ ID NO: 21 and 22)

iglB                              (SEQ ID NO: 23 and 24)
```

What is claimed is:

1. A live attenuated vaccine comprising an *F. tularensis* lacking a polynucleotide encoding CapB, (LVSΔcapB), and wherein the *F. tularensis* over-expresses an *F. tularensis* antigen selected from the group consisting of IglA, IglC and a combination thereof.

2. The live attenuated vaccine of claim 1, wherein the LVSΔcapB overexpresses an immunogenic IglC.

3. The live attenuated vaccine of claim 1, wherein the LVSΔcapB overexpresses an immunogenic IglA.

4. The live attenuated vaccine of claim 1, wherein the LVSΔcapB overexpresses an immunogenic IglA and IglC.

5. An immunogenic composition comprising a live attenuated vaccine of claim 1 useful for inducing an immune response against *Francisella tularensis*, said antigen comprising an extracellular or immunogenic polypeptide of *F. tularensis* IglA, IglC or a combination thereof linked to transcriptional promoter and termination signals.

6. The immunogenic composition of claim 5, further comprising a pharmaceutical diluent.

7. The immunogenic of claim 5, wherein the antigen comprises a sequence selected from the group consisting of SEQ ID NO: 12 and 22 and any combination of the foregoing.

8. A recombinant attenuated *F. tularensis* lacking a polynucleotide encoding CapB, LVSΔcapB and comprising a polynucleotide encoding at least one extracellular or immunogenic protein of *F. tularensis* selected from the group consisting of IglA, IglC and a combination thereof, wherein the polynucleotide encoding IglA, IglC and a combination thereof is overexpressed and that induces a immunity against *F. tularensis*.

9. A method of inducing immunity in a subject comprising administering the composition of claim 5 to the subject.

10. A method of immunizing a susceptible host against an infection of *Francisella tularensis* comprising administering to said host an amount of the immunogenic composition of claim 5 sufficient to invoke an immune response in the host.

11. The method of claim 10, wherein the composition is in a pharmaceutically acceptable carrier.

12. A method of inducing immunity in a subject comprising administering the live attenuated vaccine of claim 1.

* * * * *